(12) United States Patent
Paturel et al.

(10) Patent No.: US 11,970,535 B2
(45) Date of Patent: Apr. 30, 2024

(54) TREATMENT WITH ANTI-KIR3DL2 AGENTS

(71) Applicant: INNATE PHARMA, Marseilles (FR)

(72) Inventors: Carine Paturel, Marcy L'Etoile (FR); Helene Sicard, Marseilles (FR)

(73) Assignee: INNATE PHARMA, Marseilles (FR)

( * ) Notice: Subject to any disclaimer, the term of this patent is extended or adjusted under 35 U.S.C. 154(b) by 596 days.

(21) Appl. No.: 17/114,835

(22) Filed: Dec. 8, 2020

(65) Prior Publication Data

US 2021/0087270 A1    Mar. 25, 2021

Related U.S. Application Data

(63) Continuation of application No. 16/343,796, filed as application No. PCT/EP2017/076751 on Oct. 19, 2017, now abandoned.

(60) Provisional application No. 62/410,880, filed on Oct. 21, 2016.

(51) Int. Cl.
| | |
|---|---|
| *A61P 35/00* | (2006.01) |
| *C07K 16/28* | (2006.01) |
| *C07K 16/30* | (2006.01) |
| *A61K 39/00* | (2006.01) |

(52) U.S. Cl.
CPC .......... *C07K 16/2803* (2013.01); *A61P 35/00* (2018.01); *C07K 16/3061* (2013.01); *A61K 2039/505* (2013.01); *A61K 2039/545* (2013.01); *C07K 2317/24* (2013.01); *C07K 2317/34* (2013.01); *C07K 2317/732* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,399,595 B2 | 7/2008 | Bensussan et al. | |
| 7,732,131 B2 | 6/2010 | Moretta et al. | |
| 7,919,085 B2 | 4/2011 | Bensussan et al. | |
| 8,119,775 B2 | 2/2012 | Moretta et al. | |
| 8,268,308 B2 | 9/2012 | Bensussan et al. | |
| 8,388,970 B2 | 3/2013 | Padkaer et al. | |
| 8,465,931 B2 | 6/2013 | Moretta et al. | |
| 8,518,655 B2 | 8/2013 | Bensussan et al. | |
| 8,614,307 B2 | 12/2013 | Moretta et al. | |
| 8,637,258 B2 | 1/2014 | Padkjaer et al. | |
| 8,981,065 B2 | 3/2015 | Moretta et al. | |
| 9,018,366 B2 | 4/2015 | Padkaer et al. | |
| 9,181,341 B2 | 11/2015 | Anfossi et al. | |
| 9,708,403 B2 | 7/2017 | Padkaer et al. | |
| 9,828,427 B2 | 11/2017 | Anfossi et al. | |
| 9,902,936 B2 | 2/2018 | Moretta et al. | |
| 10,113,003 B2 | 10/2018 | Gauthier et al. | |
| 10,174,112 B2 | 1/2019 | Bonnafous et al. | |
| 10,246,510 B2 | 4/2019 | Gauthier et al. | |
| 10,253,095 B2 | 4/2019 | Romagne et al. | |
| 10,280,222 B2 | 5/2019 | Gauthier et al. | |
| 10,344,087 B2 | 7/2019 | Bonnafous et al. | |
| 10,577,419 B2 | 3/2020 | Gauthier et al. | |
| 10,676,523 B2 | 6/2020 | Andre et al. | |
| 2006/0263361 A1 | 11/2006 | Moretta et al. | |
| 2007/0178106 A1 | 8/2007 | Romagne | |
| 2008/0081346 A1 | 4/2008 | Moretta et al. | |
| 2008/0305117 A1 | 12/2008 | Padkaer et al. | |
| 2009/0075340 A1 | 3/2009 | Padkaer et al. | |
| 2009/0081240 A1 | 3/2009 | Moretta et al. | |
| 2009/0196850 A1 | 8/2009 | Romagne et al. | |
| 2010/0285531 A1 | 11/2010 | Moretta et al. | |
| 2010/0291110 A1 | 11/2010 | Padkjaer et al. | |
| 2011/0293561 A1 | 12/2011 | Romagne et al. | |
| 2012/0064081 A1 | 3/2012 | Anfossi et al. | |
| 2012/0208237 A1 | 8/2012 | Moretta et al. | |
| 2013/0143269 A1 | 6/2013 | Padkaer et al. | |
| 2014/0234342 A1 | 8/2014 | Narni-Mancinelli et al. | |
| 2015/0232556 A1 | 8/2015 | Gauthier et al. | |
| 2016/0002345 A1 | 1/2016 | Bonnafous et al. | |
| 2017/0158763 A1 | 6/2017 | Gauthier et al. | |
| 2017/0298131 A1 | 10/2017 | Andre et al. | |
| 2019/0127463 A1 | 5/2019 | Bonnafous et al. | |
| 2019/0276536 A1 | 9/2019 | Gauthier et al. | |
| 2019/0315857 A1 | 10/2019 | Bonnafous et al. | |
| 2020/0199228 A1 | 6/2020 | Gauthier et al. | |
| 2020/0299383 A1 | 9/2020 | Andre et al. | |

FOREIGN PATENT DOCUMENTS

| | | |
|---|---|---|
| WO | WO 2014/044686 | 3/2014 |
| WO | WO 2014/128221 | 8/2014 |
| WO | WO 2015/136052 | 9/2015 |
| WO | WO 2016/030488 | 3/2016 |

OTHER PUBLICATIONS

Battistella et al. (British Journal of Dermatology (2016) 175, pp. 325-333). (Year: 2016).*
Marie-Cardine et al. (Cancer Res (2014) 74 (19_Supplement): 651.). (Year: 2014).*
Marie-Cardine et al. (Journal for Immuno Therapy of Cancer 2013, 1(Suppl 1):p. 45). (Year: 2013).*
Marie-Cardine et al. (Hematol Oncol 2015; 33: 181-243, pp. 238-239 only). (Year: 2015).*
Chester et al. (Cancer Res (2015) 75 (15_Supplement): 2473). (Year: 2015).*
Bouaziz et al., J Invest Dermatol 125:1273-1278, 2005. (Year: 2005).*
"Guidance for Industry Estimating the Maximum Safe Starting Dose in Initial Clinical Trials for Therapeutics in Adult Healthy Volunteers," 2005, pp. 1-27. (Year: 2005).*
Lane et al. (Metabolomics. Jul. 2016; 12(7): pp. 1-27). (Year: 2016).*

(Continued)

*Primary Examiner* — Zachary S Skelding
(74) *Attorney, Agent, or Firm* — SALIWANCHIK, LLOYD & EISENSCHENK

(57) ABSTRACT

This invention relates to the use of KIR3DL2-targeting agents for the treatment of CTCL. The invention provides advantageous treatment regimens using anti-KIR3DL2 antibodies for the treatment of CTCL, notably in first-line CTCL.

19 Claims, 6 Drawing Sheets

Specification includes a Sequence Listing.

(56) References Cited

OTHER PUBLICATIONS

Wells et al. (Matrix Biol. (2016) 49, 25-36). (Year: 2016).*
John Carroll, "Scientist spotlights potential Achilles heel of therapeutic cancer vaccines," Fierce Pharma / Fierce Biotech, Mar. 8, 2013, 2 pages. (Year: 2013).*
Chan et al. (vol. 52, No. 11, Nov. 2005, pp. 3586-3595). (Year: 2005).*
Marie-Cardine, A. et al. "IPH4102, a Humanized KIR3DL2 Antibody with Potent Activity against Cutaneous T-cell Lymphoma" *Cancer Research*, Nov. 1, 2014, pp. 6060-6070, vol. 74, No. 21.
Schmitt, C. et al. "Therapeutic Antibodies to KIR3DL2 and Other Target Antigens on Cutaneous T-Cell Lymphomas" *Frontiers in Immunology*, Aug. 2017, pp. 1-8, vol. 8, Article 1010.
Sicard, H. et al. "A novel targeted immunotherapy for CTCL is on its way: Anti- KIR3DL2 mAb IPH4102 is potent and safe in non-clinical studies" *OncoImmunology*, Sep. 2015, pp. e1022306-1-e1022306-2, vol. 4, Issue 9.
Bagot, M. et al. "First-in-Human, Multicenter Phase I Study of IPH4102, First-in-Class Humanized Anti-KIR3DL2 Monoclonal Antibody, in Relapsed/Refractory Cutaneous T-Cell Lymphomas: Preliminary Safety, Exploratory and Clinical Activity Results" *Blood*, Dec. 2, 2016, p. 1-3, vol. 128.
Bagot, M. "New targeted treatments for cutaneous T-cell Lymphomas" *Indian Journal of Dermatology*, Jan. 1, 2017, pp. 1-5, vol. 62, No. 2.
New York: "Checkpoint antibodies in immuno-oncology", Mar. 16, 2016, Retrieved from the Internet: URL:http://innate-pharma.com/sites/default/files/ny_r_day_2016-v4.pdf, XP055383496, pp. 1-80, pp. 6, 46-49 and 80 cited in the ISR.
Written Opinion in International Application No. PCT/EP2017/076751, dated Jan. 12, 2018, pp. 1-10.
Duvic, M. et al. "Phase 1/2 study of mogamulizumab, a defucosylated anti-CCR4 antibody, in previously treated patients with cutaneous T-cell lymphoma" *Blood*, 2015, pp. 1883-1889, vol. 125, No. 12.
De Masson, A. et al. "Long-term efficacy and safety of alemtuzumab in advanced primary cutaneous T-cell lymphomas" *British Journal of Dermatology*, 2014, pp. 720-724, vol. 170.
Bagot, M. et al. "IPH4102, the first in class anti-KIR3DL2 mab is safe and clinically active in advanced cutaneous T-cell lymphoma patients: results from the dose escalation part of the IPH4102-101 phase I study" Oct. 15, 2017, pp. 1-12.
Bagot, M. et al., "First-in-Human, Multicenter Phase I Study of IPH4102, First-in-Class Humanized Anti-KIR3DL2 Monoclonal Antibody, in Relapsed/Refractory Cutaneous T-Cell Lymphomas: Preliminary Safety, Exploratory and Clinical Activity Results" Dec. 3, 2016, *American Society of Hematology Conference*, p. 1, Abstract ID 1826.

* cited by examiner

TREATMENT WITH ANTI-KIR3DL2 AGENTS

CROSS-REFERENCE TO RELATED APPLICATIONS

This application is a continuation of U.S. application Ser. No. 16/343,796, filed Apr. 22, 2019, now abandoned which is the U.S. national stage application of International Patent Application No. PCT/EP2017/076751, filed Oct. 19, 2017, which claims the benefit of U.S. Provisional Application No. U.S. 62/410,880, filed Oct. 21, 2016; the disclosures of which are hereby incorporated by reference in their entirety, including any drawings.

REFERENCE TO SEQUENCE LISTING

The present application is being filed along with a Sequence Listing in electronic format. The Sequence Listing is provided as a file entitled "KIR-7_5 T25", created 18 Oct. 2017, which is 53 KB in size. The information in the electronic format of the Sequence Listing is incorporated herein by reference in its entirety.

FIELD OF THE INVENTION

This invention relates to the use of KIR3DL2-targeting agents for the treatment of CTCL.

BACKGROUND OF THE INVENTION

A variety of T- and B-cell neoplasms can involve the skin, either primarily or secondarily. Primary cutaneous lymphomas present in the skin with no evidence of extracutaneous disease at the time of diagnosis. Primary cutaneous lymphomas often have a completely different clinical behavior and prognosis from histologically similar systemic lymphomas, which may involve the skin secondarily, and therefore require different types of treatment. Cutaneous T-cell lymphoma (CTCL) is a group of lymphoproliferative disorders characterized by localization of neoplastic T lymphocytes to the skin. Collectively, CTCL is classified as a type of non-Hodgkin lymphoma (NHL). Treatment selection for CTCL typically depends on the extent of skin involvement, the type of skin lesion, and whether the cancer has spread to the lymph nodes or other internal organs. For mycosis fungoides, treatment can be directed to the skin or to the entire body. Sézary syndrome is generally characterized by blood involvement and it is usually not treated with skin-directed therapies alone. Treatments may be prescribed alone or in combination to achieve the best long-term benefit. Skin-directed therapies in CTCL are useful for patch and limited plaque disease and include, inter alia, topical treatments such as corticosteroids, retinoids, or imiquimod, topical chemotherapy, local radiation, methotrexate, photopheresis, ultraviolet light (phototherapy).

More recently, several antibody therapeutics targeting proteins expressed at the surface of malignant cells have shown promise for the treatment of CTCL.

Alemtuzumab is a humanized IgG1 kappa monoclonal antibody specific for CD52, an antigen expressed by most T and B lymphocytes that has been used in treatment of CTCLs and PTCLs, with a usual protocol of administration is 30 mg three times/week. However, while several retrospective and prospective studies have shown a good efficacy in Sezary syndrome, alemtuzumab treatment causes a broad depletion of NK and T cells, and leads to cytopenia and immune depletion. Moreover, Clark et al., 2012 Sci. Trans. Med. 4(117): 117ra7 (DOI: 10.1126/scitranslmed.3003008) reported that alemtuzumab treatment nevertheless does not fully deplete T cells in skin. Alemtuzumab depleted all T cells in blood, but a diverse population of skin resident T effector memory cells remained in skin after therapy. T cell depletion with alemtuzumab required the presence of neutrophils, a cell type frequent in blood but rare in normal skin, suggesting that central memory T cells were depleted because they recirculate between the blood and the skin, whereas skin resident effector memory T cells were spared because they are sessile and non-recirculating.

Even more recently, mogamulizumab (KW-0761) has emerged as a treatment for relapsed/refractory CTCL and PTCL. Mogamulizumab is a humanized anti-CCR4 monoclonal antibody that depletes CCR4 and has been approved for use in Japan for the treatment of CCR4+ ATLL, PTCL or CTCL. Mogalizumab, however, also leads to depletion of healthy CCR4 expressing cells, resulting in a depletion of healthy regulatory T (TReg) cells. Depletion of healthy TReg cells has the consequence that it pre-excludes subsequent or combined hematopoietic stem cell transplants due to risk of Graft-versus-host disease, or other therapeutic agents that require a properly functioning immune system notably for their safety.

A further immunotherapeutic agent showing promising efficacy in treating CTCL is brentuximab vedotin, an antibody-drug conjugate that targets the CD30 antigen and depletes CD30-expressing cells. Adcetris™ (Brentuximab vedotin) is anti-CD30 monoclonal antibody (clone cAC10) attached by a protease-cleavable linker to a microtubule disrupting agent, monomethyl auristatin E (MMAE). Once bound to CD30, brentuximab vedotin is internalized and MMAE is released with the action of lysosomal enzymes on the linker, leading to cell death. While brentuximab vedotin has shown high efficacy with manageable toxicity, the treatment may also target healthy CD30-expressing immune cells, notably activated B- and T-cells. Some authors have also suggested that MMAE released in the tumor environment may contribute to the mechanism of action by depletion of regulatory T (TReg) cells.

Finally, KIR3DL2 has been proposed as a target for CTCL (see, e.g., Ortonne et al. (2006) Blood 107(10):4030-4038; and PCT publication no. WO02/50122). KIR3DL2/CD158k is a cell surface receptor expressed on healthy circulating NK and CD8+T lymphocytes. KIR3DL2 has also been found on the surface of CTCL cell lines and freshly isolated CD4+PBL from SS patients, and in circulating malignant tumor cells in CTCL patients (Nikolova et al. (2002) Leuk Lymphoma. 43(4):741-746). Poszepczynska-Guigné J Invest Dermatol. (2004) 122(3):820-3 report a strong positive correlation between the percentage of CD158k+ blood lymphocytes analyzed by flow cytometry and the percentage of atypical circulating cells (Sezary cells) determined by cytomorphology in a large group of patients with Sezary syndrome, and that circulating CD4+CD158k+ lymphocytes correspond to the malignant clonal cell population. KIR3DL2 has therefore been proposed as a marker for the evaluation of the circulating tumoral burden and the follow-up of patients with Sezary syndrome. PCT publication no. WO2014/044686 reports anti-KIR3DL2 antibodies, in particular antibodies efficient in mediating ADCC towards circulating KIR3DL2-expressing tumor cells or tumor cell lines.

While many treatments for CTCL are available, many or most of them have side effects that limit their use, including antibodies that target proteins expressed at the surface of tumor cells. Notably, both CD52 and CC4 respectively targeted by alemtuzumab and mogamulizumab are also expressed on healthy cells leading to side effects linked to depletion of healthy T and NK cells, and additionally limiting the range of subsequent or combined use of other available anti-CTCL treatments. Improved treatments for CTCL are therefore needed.

SUMMARY OF THE INVENTION

The present disclosure provides use of depleting anti-KIR3DL2 agents as immunomodulating agents, in an amount effective to induce immune responses at extravascular, notably cutaneous, sites of T cell proliferative disorders. The treatment is, in particular, capable of depleting malignant KIR3DL2-expressing cells without causing the depletion of healthy KIR3DL2-expressing NK and T cells. The agents can be used in treatment, notably, of cutaneous T cell lymphoma (CTCL) irrespective of presence of detectable malignant cells in circulation. The agents can advantageously be used in patients having overt or advanced disease yet lacking detectable malignant KIR3DL2-expressing cells in circulation. The agents can advantageously be used in treatment of patients having indolent or early stage T cell lymphomas (e.g., CTCL) characterized by having low or no significant malignant cells in circulation. In one embodiment, the agents can advantageously be used as first line treatment in a T cell lymphoma (e.g., a CTCL). Optionally the subject has not yet been treated with a chemotherapeutic agent. Optionally the subject has not yet been treated with an immunotherapeutic agent (e.g. mogamulizumab, alemtuzumab and/or brentuximab vedotin). Optionally the subject has not yet been treated with a bone marrow transplant or hematopoietic stem cell transplant. Optionally the subject has progressing disease. In one embodiment, the agents can advantageously be used to treat a patient prior to bone marrow transplantation or hematopoietic stem cell transplantation.

In a clinical trial of relapsed/refractory CTCL in human patients with an ADCC-inducing anti-KIR3DL2 antibody the inventors surprisingly observed a strong anti-tumor effect in skin lesions in patients who received very low amounts of anti-KIR3DL2 antibody—amounts sufficient to reach but a very small number of malignant cells in skin, and in certain dose levels, only a portion of malignant cells in blood (if any were present).

Furthermore, a strong anti-tumor effect in skin disease (erythroderma, plaque or patches in skin) was observed in a patient who lacked detectable malignant KIR3DL2-expressing cells in circulation.

Additionally, analysis from the clinical trials revealed more generally that patients experienced a strong amelioration of disease in skin, including restoration of normal skin structure and strong reduction of KIR3DL2-expressing cells at cutaneous sites of disease, upon treatment with a depleting anti-KIR3DL2 agent at doses administered so as to provide as little as partial/minimal NK lytic activity towards KIR3DL2+ cells in circulation, and far lower than the amount that would provide significant occupation of KIR3DL2 receptors on cells in skin tumors (e.g. including in patients' with high tumor burden).

The results suggest that KIR3DL2 binding agents, when administered so as to provide activity in circulation over a sufficiently long period (e.g. 10 weeks or more), can be effective in treating disease in tissues (e.g. skin) despite low amounts therapeutic agent expected to act at the disease sites in tissues. Moreover, the treatment advantageously can avoid depletion of healthy KIR3DL2-expressing NK and/or T cells in circulation, unlike that which is observed with other treatments. The KIR3DL2 binding agents can, accordingly, be particularly advantageously used in first-line treatment of CTCL, including but not limited to individuals having early and/or indolent disease. In one embodiment, the KIR3DL2 binding agent is used in combination with (e.g., prior to) hematopoietic stem cell or bone marrow transplantation, in both early and later stages of disease. In one embodiment, the KIR3DL2 binding agent is used to treat first-line CTCL In one embodiment, the KIR3DL2 binding agent is used to treat CTCL in a subject who is not eligible (e.g. due to high blood and/or skin tumor burden) for hematopoietic stem cell or bone marrow transplantation. In one embodiment, the KIR3DL2 binding agent achieves a decrease in blood and/or skin tumor burden without depletion of healthy NK and/or T cells, and renders the subject eligible for hematopoietic stem cell or bone marrow transplantation.

In our studies, we used a new paradigm for determining dosing of anti-KIR3DL2 antibodies. Rather than seek to maintain full KIR3DL2 occupancy on the malignant cells in solid tumors in skin which are believed to require particularly high blood concentrations in individuals with higher tumor burden associated with advanced disease, anti-KIR3DL2 antibodies dosed in an amount and frequency that were lower, but sufficient to maintain concentration in blood (e.g., blood serum) that provides for example of a NK % lytic capacity of at least 60%, 80%, 90% or 100%, led to remarkable anti-tumor responses while permitting a single dosing regimen for all patients. These treatment regimens can be used for an extended treatment period and/or several treatment cycles, optionally preceded by an induction or loading period in which higher administrations frequencies (or higher doses) are employed. In certain embodiments, a single treatment regimen (e.g. same dosage and same frequency of administration) can advantageously be employed in both individuals having low blood and/or cutaneous disease burden and in individuals having high blood and/or cutaneous disease burden.

In one embodiment, a common treatment regimen (e.g. same dosage and same frequency of administration) that does not result in healthy NK and/or T cell depletion can advantageously be employed in individuals irrespective of initial tumor burden and/or disease stage, wherein the common treatment regimen is preceded by an induction regimen or loading period in which anti-KIR3DL2 antibody is administered to an individual (e.g. an individual having a high tumor burden) at a higher administration frequency (optionally wherein the doses at each administration of antibody in the common treatment regimen and the induction regimen are the same.

In one aspect, the KIR3DL2 receptor, rather than being clonally expanded from circulating malignant and non-malignant CD4(+) T cell populations, may be arising from skin manifestations of disease. Accordingly, KIR3DL2 may actually be sufficiently expressed in skin T cell malignancies in cases where patients lack blood involvement (lacking detectable KIR3DL2-expressing malignant cells in circulation), including in indolent or early-stage CTCL, to permit therapeutic targeting by an anti-KIR3DL2 binding agent. Additionally or alternatively, tumor cells from skin lesions may enter (or re-enter) circulation, such that lysis of a small number of tumor cells in circulation helps to contribute to a broader anti-tumor response in skin.

In one aspect, provided is an agent that binds a KIR3DL2 polypeptide and is capable of causing effector cell-mediated lysis of a KIR3DL2-expressing cell, for use in treatment of a CTCL. In one embodiment, the CTCL has tissue manifestation of disease, e.g., pruritus, erythroderma and/or skin tumors. In one embodiment, the agent is used as first-line treatment. In one embodiment, provided is a method comprising administering to an individual a T cell malignancy (e.g. a CTCL) an agent that binds a KIR3DL2 polypeptide and is capable of causing effector cell-mediated lysis of a KIR3DL2-expressing cell. In one aspect, provided is an agent that binds a KIR3DL2 polypeptide and is capable of causing effector cell-mediated lysis of a KIR3DL2-expressing cell, for use preparing an individual having a T cell malignancy (e.g. a CTCL) for a subsequent bone marrow transplant or hematopoietic stem cell transplant. In one aspect, provided is an anti-KIR3DL2 binding agent for use in treatment of an individual having a T cell malignancy with tissue manifestation of disease (e.g., a CTCL with pruritus, erythroderma and/or skin tumors) but lacking detectable KIR3DL2-expressing malignant cells in circulation. In one aspect, provided is an anti-KIR3DL2 binding agent for use in treatment of an individual having an indolent or early-stage CTCL.

In one aspect, an anti-KIR3DL2 binding agent can be administered in an amount effective to achieve as little as the $EC_{10}$ for NK lytic capacity in circulation can suffice to induce a strong anti-tumor effect in patients having CTCL with skin manifestations of disease e.g., pruritus, erythroderma and/or skin tumors. Doses that maintained as little as $EC_{10}$ for NK lytic capacity in circulation reduced blood tumor burden and doses that maintained as little as the $EC_{60}$ for NK lytic capacity in circulation restored normal skin structure and reduces KIR3DL2-expressing cells at cutaneous sites of disease. Accordingly, in one embodiment, provided is an anti-KIR3DL2 binding agent for use in treatment of an individual having a skin manifestation of CTCL but no or low levels of detectable malignant cells in circulation, wherein an anti-KIR3DL2 binding agent is administered in an amount effective to maintain as little as the $EC_{10}$ for NK lytic capacity in circulation can suffice to induce a strong anti-tumor effect. In another embodiment, provided is an anti-KIR3DL2 binding agent for use in treatment of an individual having a skin manifestation of CTCL and detectable (e.g. higher levels of) malignant cells in circulation, wherein the treatment comprises a plurality of administrations of an anti-KIR3DL2 binding agent in an amount effective to maintain as little the $EC_{10}$ for NK lytic capacity.

Targeting KIR3DL2 by an anti-KIR3DL2 binding agent can therefore be advantageous in several therapeutic settings, moreover without requiring prior testing of KIR3DL2 expression on malignant cells in circulation and/or skin. Furthermore, use of an anti-KIR3DL2 binding agent does not require dosage that would maintain full receptor occupancy on tumor cells in skin disease (e.g. erythroderma, skin lesions) on all patients within a population having a diverse range of tumor burden, and can benefit from the ability of healthy immune cells (e.g. NK cells, CD8 T cells, gamma-delta T cells) to contribute to a broader anti-tumor response through depletion of a small number of KIR3DL2-expressing tumor cells in circulation (e.g., below the detection limit), for example tumor cells that enter circulation from skin lesions, and/or through the induction of antibody-dependent cellular phagocytosis (ADCP) in skin lesions.

In one aspect, provided are therapeutic regimens for administration of anti-KIR3DL2 agents capable of inducing such anti-tumor responses.

In one aspect, the therapeutic regimens disclosed herein have the advantage of being adapted to treating individuals with T cell lymphomas (e.g. CTCL) having detectable malignant cells in circulation (e.g. KIR3DL2-expressing malignant cells) as well as individuals with T cell lymphomas lacking such detectable malignant cells in circulation. Notably, a single administration dose and/or dosing regimen can be used to treat such patients, avoiding the need for different treatments as a function of levels (or lack of) malignant cells in circulation. Advantageously, the therapeutic regimens can be used to treat patients having high tumor burden, optionally by repeatedly and/or continuously over a period of time, to generate a broader response against skin manifestations.

In one embodiment, an advantageous treatment comprises administering to an individual an amount and frequency of anti-KIR3DL2 agent that provides a concentration in blood (e.g., blood serum) that corresponds to at least the $EC_{10}$, the $EC_{60}$, the $EC_{80}$, the $EC_{90}$, or the $EC_{100}$ for NK lytic capacity. Optionally, the amount and frequency of anti-KIR3DL2 agent is less than that which would maintain the $EC_{90}$, or the $EC_{100}$ for receptor saturation in skin (or within skin lesions or tumors, e.g. advanced disease stages, high tumor burden or erythema).

In one aspect of any embodiment herein, an advantageous treatment comprises a plurality of administrations of an amount and frequency of anti-KIR3DL2 agent that provides a concentration in blood (e.g., blood serum) that is at least the $EC_{10}$, the $EC_{60}$, the $EC_{80}$, the $EC_{90}$, or the $EC_{100}$ for NK lytic capacity. Optionally, the therapy is administered for a duration of at least 10 weeks, 12 weeks, 3 months, 4 months or 6 months. Optionally, the administrations are separated by a period of time between about one week and about two months. Optionally, the anti-KIR3DL2 agent is administered at least 4, 6, 8, 10 or 20 times. Optionally, the amount and frequency of anti-KIR3DL2 agent is less than that which would provide the $EC_{90}$, or the $EC_{100}$ for receptor saturation in skin (or within skin lesions or tumors, e.g. advanced disease stages, high tumor burden or erythema).

In one embodiment, an advantageous treatment comprises administering to an individual an amount of anti-KIR3DL2 agent that maintains, between two successive administrations, a concentration in blood (e.g., blood serum) that provides a NK % lytic capacity of at least 10%, optionally at least 60%, optionally at least 80%, optionally at least 90% or optionally 100%).

In one embodiment, an advantageous treatment comprises administering to an individual an amount of anti-KIR3DL2 agent that maintains, between two successive administrations, a concentration in blood (e.g., blood serum) that is at least the $EC_{10}$, the $EC_{60}$, the $EC_{80}$, the $EC_{90}$, or the $EC_{100}$ for NK lytic capacity. In one embodiment, the treatment maintains a trough concentration of at least the concentration in blood (e.g., blood serum) that is at least the $EC_{10}$, the $EC_{60}$, the $EC_{80}$, the $EC_{90}$, or the $EC_{100}$ for NK lytic capacity.

Optionally, the treatment is administered for a duration of at least 10 weeks, 12 weeks, 3 months, 4 months or 6 months.

Optionally, the administrations are separated by a period of time between about one week and about two months.

Optionally, the treatment comprises at least 4, 6, 8, 10 or 20 successive administrations of the anti-KIR3DL2 agent.

In one embodiment, the individual is (remains eligible or is made eligible) eligible for hematopoietic stem cell transplantation or bone marrow transplantation prior to treatment with the anti-KIR3DL2 agent.

In one embodiment, the individual is not eligible for hematopoietic stem cell transplantation or bone marrow transplantation prior to treatment with the anti-KIR3DL2 agent, and is made eligible for hematopoietic stem cell transplantation or bone marrow transplantation after treatment with the anti-KIR3DL2 agent.

Optionally, the treatment with the anti-KIR3DL2 agent is prior to hematopoietic stem cell transplant or bone marrow transplant. Optionally, the treatment is in combination with hematopoietic stem cell transplant or bone marrow transplant. In any embodiment, a treatment method further comprises administering to the individual a hematopoietic stem cell transplant or bone marrow transplant following treatment with the anti-KIR3DL2 agent.

In one embodiment, provided is an agent that binds a KIR3DL2 polypeptide and is capable of causing effector cell-mediated lysis of a KIR3DL2-expressing cell, for use in treating a T cell malignancy with tissue manifestations, wherein the treatment is effective in both individuals having blood involvement and in individuals lacking blood involvement.

In one embodiment, provided is a method comprising administering to an individual a T cell malignancy (e.g. a CTCL) an agent that binds a KIR3DL2 polypeptide and is capable of causing effector cell-mediated lysis of a KIR3DL2-expressing cell, for at least one administration cycle in which the agent is administered at least twice in an amount that maintains a % lytic capacity in circulation of at least 10%, optionally at least 60%, 80%, or 90%, or optionally 100%, between two successive administrations of the agent. E.g., the agent is administered in an amount that maintains a concentration in blood (e.g., blood serum) of at least the $EC_{10}$, the $EC_{60}$, the $EC_{80}$, the $EC_{90}$, or the $EC_{100}$ for NK lytic capacity. In one embodiment, the agent is administered intravenously. In one embodiment, the agent is administered at least 4, 6, 8 or 10 times, optionally wherein successive administrations are separated by a period of between one week and one month. In one embodiment, the agent that binds a KIR3DL2 polypeptide is administered such that the concentration in circulation that provides said % lytic capacity (or the EC value) in circulation is maintained for at least 10 weeks, optionally at least 3 months, optionally at least 6 months. In one embodiment, the method is a method of treating a T cell malignancy with tissue manifestations that is effective in both individuals having blood involvement and in individuals lacking blood involvement. In one embodiment, the method is a method for preparing an individual having a T cell malignancy (e.g. a CTCL) for a subsequent bone marrow transplant or hematopoietic stem cell transplant.

Optionally, in any embodiment, the treatment regimen is preceded by an induction or loading period in which the anti-KIR3DL2 binding agent is administered in a higher amount and/or frequency. Optionally, in any embodiment, the treatment regimen is preceded by an induction or loading period in which the anti-KIR3DL2 binding agent is administered (e.g. in a plurality of successive administrations) in the same amount but at a higher frequency.

Optionally, the amount of anti-KIR3DL2 agent is less than that which would provide the $EC_{80}$, the $EC_{90}$, or the $EC_{100}$ for receptor saturation in tissues (e.g. extravascular tissues, disease tissue, skin, within skin lesions or tumors, including e.g. advanced disease stages, high tumor burden or erythema).

In one embodiment, the anti-KIR3DL2 binding agent is an agent that mediates effector-cell mediated lysis of a KIR3DL2-expressing cell (e.g. a tumor cell). Optionally, the agent is an antigen binding polypeptide, optionally an antibody or fragment thereof (e.g. a protein comprising a VH and/or a VL domain), that binds a KIR3DL2 polypeptide, or an immune effector cell that expresses such a polypeptide (e.g. a chimeric antigen receptor immune effector cell), antibody or other compound. Optionally, the antibody is a depleting polypeptide (antibody). Optionally, the antibody is monospecific or a multispecific (e.g. bispecific) antibody that directs ADCC and/or ADCP toward a KIR3DL2-expressing cell.

In one aspect of any embodiment herein, a KIR3DL2-binding agent comprises an anti-KIR3DL2 antibody of human IgG isotype capable of mediating ADCC, and is administered to an individual at least twice, in an amount effective to achieve (and/or to maintain for a specified period of time or between two successive administrations) a blood (serum) concentration of anti-KIR3DL2 antibody of at least 0.1 μg/ml (or, optionally at least 0.4, 1, 2, 10 μg/mL), optionally less than 60 or less than 100 μg/mL, optionally between 2 and 30 μg/mL, optionally between 2 and 60 μg/mL. In one embodiment, the antibody is administered once per week, once every two weeks, once every month (or four weeks), optionally between once per month and once every two months, intravenously.

These aspects are more fully described in, and additional aspects, features, and advantages will be apparent from, the description of the invention provided herein.

DESCRIPTION OF THE INVENTION

Figure 1A:
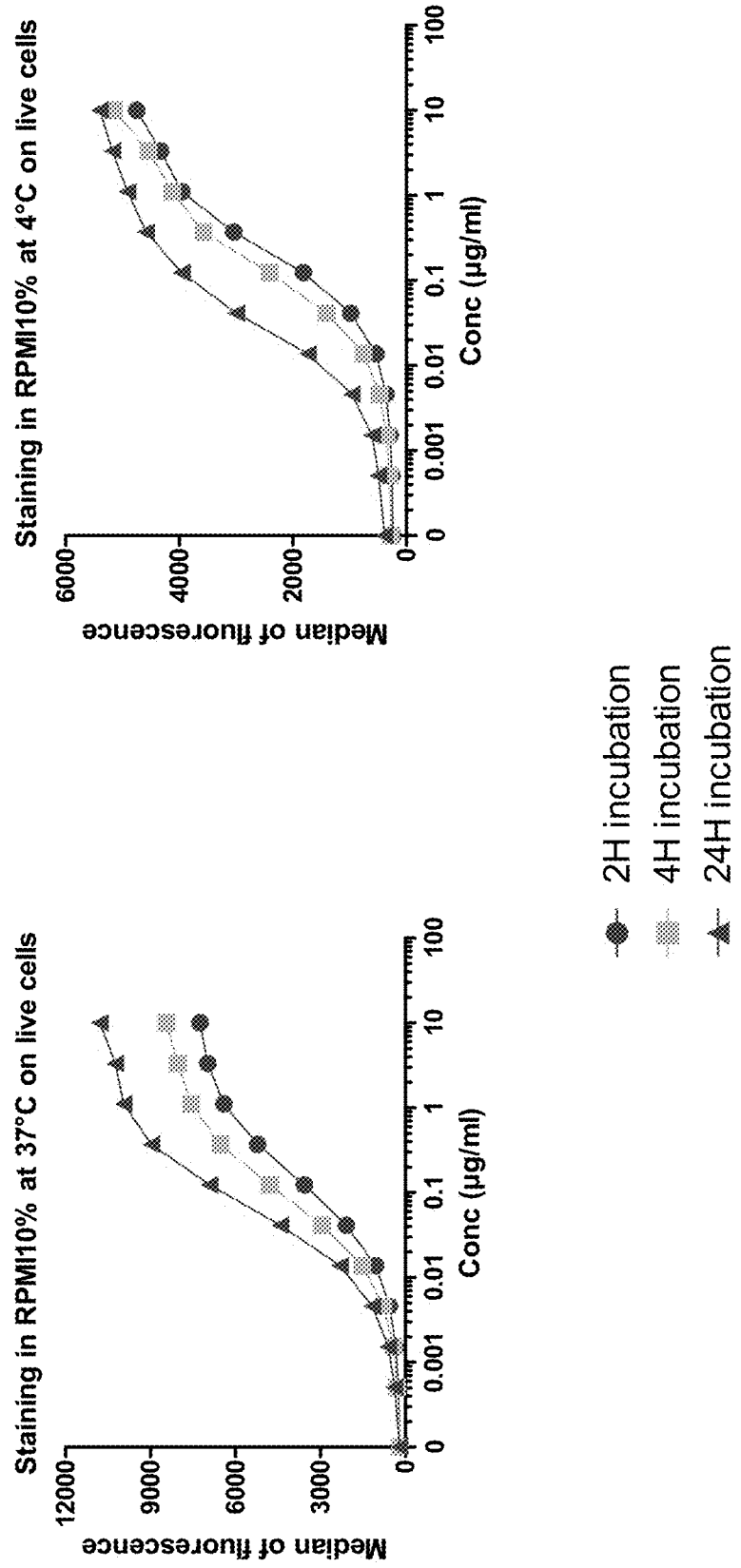
FIG. 1A shows while incubation at 4° C. which inhibits receptor internalization/cycling was expected to result in an at least equal level of cell-surface KIR3DL2, staining with antibody 2B12 (human IgG1) was higher at 37° C. than at 4° C. Furthermore, higher median fluorescence was observed with increasing duration of incubation, the greatest KIR3DL2 expression was observed after 24 hours of incubation.

As used herein, "a" or "an" may mean one or more. As used in the claim(s), when used in conjunction with the word "comprising", the words "a" or "an" may mean one or more than one. As used herein "another" may mean at least a second or more.

Where "comprising" is used, this can optionally be replaced by "consisting essentially of" or by "consisting of".

Whenever "treatment" is mentioned with reference to a disease and an anti-KIR3DL2 binding agent (e.g. antibody), there is meant: (a) method of treatment of a disease, said method comprising the step of administering (for at least one treatment) an anti-KIR3DL2 binding agent, (e.g., in a pharmaceutically acceptable carrier material) to a warm-blooded animal, especially a human, in need of such treatment, in a dose that allows for the treatment of disease, (a therapeutically effective amount), e.g., in a dose (amount) as specified hereinabove and herein below; (b) the use of an anti-KIR3DL2 binding agent for the treatment of disease, or an anti-KIR3DL2 binding agent, for use in said treatment (especially in a human); (c) the use of an anti-KIR3DL2 binding agent for the manufacture of a pharmaceutical preparation for the treatment of disease, a method of using an anti-KIR3DL2 binding agent for the manufacture of a pharmaceutical preparation for the treatment of disease, comprising admixing an anti-KIR3DL2 binding agent with a pharmaceutically acceptable carrier, or a pharmaceutical preparation comprising an effective dose of an anti-KIR3DL2 binding agent that is appropriate for the treatment of disease; or (d) any combination of a), b), and c), in accordance with the subject matter allowable for patenting in a country where this application is filed.

The term "biopsy" as used herein is defined as removal of a tissue for the purpose of examination, such as to establish diagnosis. Examples of types of biopsies include by application of suction, such as through a needle attached to a syringe; by instrumental removal of a fragment of tissue; by removal with appropriate instruments; by surgical excision, such as of the whole lesion; and the like.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG are the exemplary classes of antibodies employed herein because they are the most common antibodies in the physiological situation and because they are most easily made in a laboratory setting. In one embodiment, an antibody is a monoclonal antibody. Provided are humanized, chimeric, human, or otherwise-human-suitable antibodies. "Antibodies" also includes any fragment or derivative of any of the herein described antibodies. "Fragments" comprise a portion of the intact antibody, generally the antigen binding site or variable region. Examples of antibody fragments include Fab, Fab', Fab'-SH, F (ab') 2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific (e.g. bispecific) antibodies formed from antibody fragments. Included, inter alia, are a nanobody, domain antibody, single domain antibody or a "dAb".

The term "specifically binds to" means that an antibody can bind in a competitive binding assay to the binding partner, e.g. KIR3DL2, as assessed using either recombinant forms of the proteins, epitopes therein, or native proteins present on the surface of isolated target cells. Competitive binding assays and other methods for determining specific binding are further described below and are well known in the art.

When an antibody is said to "compete with" a particular monoclonal antibody, it means that the antibody competes with the monoclonal antibody in a binding assay using either recombinant KIR3DL2 molecules or surface expressed KIR3DL2 molecules. For example, if a test antibody reduces the binding of 19H12, 12B11, 10F6, 2B12, 18C6, 9E10, 10G5, 13H1, 5H1, 1E2, 1C3 or 20E9 to a KIR3DL2 polypeptide or KIR3DL2-expressing cell in a binding assay, the antibody is said to "compete" respectively with 19H12, 12B11, 10F6, 2B12, 18C6, 9E10, 10G5, 13H1, 5H1, 1E2, 1C3 or 20E9.

The term "affinity", as used herein, means the strength of the binding of an antibody to an epitope. The affinity of an antibody is given by the dissociation constant Kd, defined as [Ab]×[Ag]/[Ab-Ag], where [Ab-Ag] is the molar concentration of the antibody-antigen complex, [Ab] is the molar concentration of the unbound antibody and [Ag] is the molar concentration of the unbound antigen. The affinity constant $K_a$ is defined by 1/Kd. Methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One standard method well known in the art for determining the affinity of mAbs is the use of surface plasmon resonance (SPR) screening (such as by analysis with a BIAcore™ SPR analytical device).

The term "epitope" refers to an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

The term "intracellular internalization", or "internalization" when referring to a KIR3DL2 polypeptide and/or antibody that binds such, refers to the molecular, biochemical and cellular events associated with the process of translocating a molecule from the extracellular surface of a cell to the intracellular surface of a cell. The processes responsible for intracellular internalization of molecules are well-known and can involve, inter alia, the internalization of extracellular molecules (such as hormones, antibodies, and small organic molecules); membrane-associated molecules (such as cell-surface receptors); and complexes of membrane-associated molecules bound to extracellular molecules (for example, a ligand bound to a transmembrane receptor or an antibody bound to a membrane-associated molecule). Thus, "inducing and/or increasing intracellular internalization" comprises events wherein intracellular internalization is initiated and/or the rate and/or extent of intracellular internalization is increased.

The term "depleting", "deplete" or "depletion", with respect to KIR3DL2-expressing cells means a process, method, or composition that can kill, eliminate, lyse or induce such killing, elimination or lysis, so as to negatively affect the number of KIR3DL2-expressing cells present in a sample or in a subject. Depleting of cells can occur, for example, via ADCC.

The term "agent" is used herein to denote a chemical compound, a mixture of chemical compounds, a biological macromolecule, a cell, or an extract made from biological materials. The term "therapeutic agent" refers to an agent that has biological activity.

A "humanized" or "human" antibody refers to an antibody in which the constant and variable framework region of one or more human immunoglobulins is fused with the binding region, e.g. the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, MD).

The term "NK % lytic capacity" refers to the ability of NK cells from healthy donors to lyse tumor cells (e.g. HUT78 cells) in an in vitro cytotoxicity assay, as measured in a $^{51}$Cr release assay, by the percentage of maximal tumor cell lysis obtained (=Tumor cell lysis/Max tumor cell lysis at saturation×100). Examples of suitable assays employing PBMC and HUT78 cells as effector and target cells are described in the Examples herein. The "$EC_{10}$" (or "$EC_{60}$", "$EC_{80}$", "$EC_{90}$", or "$EC_{100}$") with respect to NK lytic capacity refers to the efficient concentration of anti-KIR3DL2 agent which produces 10% (or 60%, 80%, 90% or 100% when referring respectively to the "$EC_{60}$", "$EC_{80}$", "$EC_{90}$", or "$EC_{100}$") of its maximum response or effect with respect to such NK lytic capacity.

The term "antibody-dependent cell-mediated cytotoxicity" or "ADCC" is a term well understood in the art, and refers to a cell-mediated reaction in which non-specific cytotoxic cells that express Fc receptors (FcRs) recognize bound antibody on a target cell and subsequently cause lysis of the target cell. Non-specific cytotoxic cells that mediate ADCC include natural killer (NK) cells, macrophages, monocytes, neutrophils, and eosinophils.

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "modification" when referring to a sequence of amino acids (e.g., "amino acid modification"), is meant an amino acid substitution, insertion, and/or deletion in a polypeptide sequence. By "modification" or "amino acid modification" is meant an amino acid substitution, insertion, and/or deletion in a polypeptide sequence. By "amino acid substitution" or "substitution" herein is meant the replacement of an amino acid at a given position in a protein sequence with another amino acid. For example, the substitution P14S refers to a variant of a parent polypeptide, in which the proline at position 14 is replaced with serine. A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence.

Within the context herein, the term antibody that "binds" a polypeptide or epitope designates an antibody that binds said determinant with specificity and/or affinity.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Methods for determining identity are designed to give the largest match between the sequences tested. Methods of determining identity are described in publicly available computer programs. Computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

Treatment of Disease

Anti-KIR3DL2 agents and the administrations regimens disclosed herein can be used advantageously to treat KIR3DL2-expression T cell, lymphomas, notably CTCL, optionally as first-line treatment, optionally Sezary Syndrome (SS), optionally Mycosis fungoides (MF), optionally transformed MF, optionally advanced stage disease (e.g. stage IIB, III, IIIA, IIIB, IVA1, IVA2 or IVB), optionally disease with peripheral blood involvement, optionally disease with detectable or high levels of KIR3DL2-expressing malignant cells in peripheral blood, optionally indolent or early stage disease, optionally stage IA, IB or, IIA, disease, optionally disease without peripheral blood involvement, optionally disease without detectable or with low levels of KIR3DL2-expressing malignant cells in peripheral blood. In another aspect, provided is a method of preventing a lymphoma in an individual having a CTCL. In another aspect, provided is a method of reducing the risk of disease progression, reducing the risk of lymphoma in a cell population that has undergone initiation, in an individual having a CTCL. In another aspect, provided is a method of preparing a subject for, or making a subject eligible for, a hematopoietic stem cell or bone marrow transplant.

Cutaneous T-cell lymphoma (CTCL) (see the image below) is a group of lymphoproliferative disorders characterized by localization of neoplastic T lymphocytes to the skin. Collectively, CTCL is classified as a type of non-Hodgkin lymphoma (NHL). The World Health Organization-European Organization for Research and Treatment of Cancer (WHO-EORTC) classification of CTCLs is reported in Willemze et al. (2005) Blood 105:3768-3785. The WHO-EORTC divides CTCL into those with indolent clinical behavior and those with aggressive subtypes. A third category is that of precursor hematologic neoplasms that are not T-cell lymphomas (CD4+/CD56+ hematodermic neoplasm, blastic natural killer (NK)-cell lymphoma or B-cell derived primary cutaneous neoplasms). CTCLs which can have indolent clinical behavior include Mycosis fungoides (MF) and its variants, primary cutaneous CD30+ lymphoproliferative disorder (e.g., primary cutaneous anaplastic large cell lymphoma, lymphomatoid papulosis), subcutaneous panniculitis-like T-cell lymphoma (provisional) and primary cutaneous CD4+ small/medium-sized pleomorphic T-cell lymphoma (provisional). CTCLs with aggressive clinical behavior include Sézary syndrome (SS), Adult T-cell leukemia/lymphoma, Extranodal NK/T-cell lymphoma, nasal type, Primary cutaneous peripheral T-cell lymphoma, unspecified, Primary cutaneous aggressive epidermotropic CD8+ T-cell lymphoma (provisional) and Cutaneous gamma/delta-positive T-cell lymphoma (provisional).

The most common CTCLs are MF and SS. Their features are reviewed, e.g. in Willemze et al. (2005) Blood 105:3768-3785, the disclosure of which is incorporated herein by reference. In most cases of MF, the diagnosis is reached owing to its clinical features, disease history, and histomorphologic and cytomorphologic findings. An additional diagnostic criterion to distinguish CTCL from inflammatory dermatoses is demonstration of a dominant T-cell clone in skin biopsy specimens by a molecular assay (e.g., Southern blot, polymerase chain reaction (PCR)). Genetic testing may also be considered. Classic mycosis fungoides is divided into three stages: (1) Patch (atrophic or non-atrophic): Nonspecific dermatitis, patches on lower trunk and buttocks; minimal/absent pruritus; (2) Plaque: Intensely pruritic plaques, lymphadenopathy and (3) Tumor: Prone to ulceration. Sézary syndrome is defined by erythroderma and leukemia. Signs and symptoms include edematous skin, lymphadenopathy, palmar and/or plantar hyperkeratosis, alopecia, nail dystrophy, ectropion and hepatosplenomegaly. For a diagnosis of Sézary syndrome, criteria typically include absolute Sézary cell count, immunophenotypic abnormalities, loss of T-cell antigens and/or a T-cell clone in the peripheral blood shown by molecular or cytogenetic methods.

CTCL stages include I, II, III and IV, according to TNM classification, and as appropriate, peripheral blood involvement. Peripheral blood involvement with mycosis fungoides or Sézary syndrome (MF/SS) cells is correlated with more advanced skin stage, lymph node and visceral involvement, and shortened survival. ME and SS have a formal staging system proposed by the International Society for Cutaneous Lymphomas (ISCL) and the European Organization of Research and Treatment of Cancer (EORTC). See, Olsen et al., (2007) Blood. 110(6):1713-1722; and Agar et al. (2010) J. Clin. Oncol. 28(31):4730-4739, the disclosures of which are incorporated herein by reference. In SS and MF, stage IV (IVA1, IVA2 and IVB) can include B2 peripheral blood involvement (high blood-tumor burden: ≥1,000/μL Sézary cells with positive clone). SS and MF stages include I (IA and IB), II (IIA and IIB), III (III, IIIA and IIIB) and IV (IVA1, IVA2 and IVB).

A treatment designed to effectuate effector cell-mediated lysis of malignant KIR3DL2+ cells in circulation may, through lysis of as little as a small number of circulating cells (compared to the malignant cells overall, e.g. in extracellular manifestations of disease), through activation of a limited number of effector cells in circulation, and/or through the induction of antibody-dependent cellular phagocytosis (ADCP) toward a limited number of malignant cells in skin lesions, of generating an anti-tumor response that leads to elimination of malignant cells and generally disease improvement in skin lesions. Responses were obtained through repeated dosing of a KIR3DL2-binding antibody, via different treatment regimens designed to maintain a particular amount of anti-KIR3DL2 binding agent in circulation effective to provide the $EC_{10}$ for NK lytic capacity. While the administration regimens ameliorated skin lesions in patients having low or no blood involvement, the repeated administration regimens also ameliorated skin lesions in patients having high blood involvement.

Upon diagnosis of a CTCL, a subject can be treated with an anti-KIR3DL2 binding agent. The treatment, irrespective of tumor burden, can be used to eliminate malignant cells while maintaining healthy NK and T cells. This treatment is consequently compatible with subsequent BMT or HSCT. In one embodiment, the disclosure provides use of anti-KIR3DL2 binding agent as a first line therapy to treat a subject having a CTCL. The term "first-line therapy" as used herein refers to the first type of systemic drug therapy given for the treatment of CTCL. This can be a single-agent, combination or maintenance therapy offered initially following diagnosis.

In one aspect, provided is method for treating a CTCL in an individual, the method comprising administering to the individual an anti-KIR3DL2 binding agent without a step of prior testing of KIR3DL2 expression on malignant cells from a blood sample.

In one aspect, provided is method for treating a CTCL in an individual, the method comprising administering to the individual an anti-KIR3DL2 binding agent without a step of prior testing of KIR3DL2 expression on malignant cells from a skin biopsy.

In one aspect, provided is method for treating a CTCL in an individual lacking detectable KIR3DL2-expressing malignant cells (e.g. KIR3DL2-expressing Sézary cells) in circulation, the method comprising administering to the individual an anti-KIR3DL2 binding agent. In one aspect, provided is method for treating a CTCL in an individual having low levels of detectable KIR3DL2-expressing malignant cells (e.g. KIR3DL2-expressing Sézary cells) in circulation, the method comprising administering to the individual an anti-KIR3DL2 binding agent.

In one aspect, provided is method for treating a CTCL in an individual having less than B2 stage peripheral blood involvement, comprising administering to the individual an anti-KIR3DL2 binding agent. Optionally the individual has blood-tumor burden of less than 1,000/μL Sézary cells, and/or without positive clone.

In one aspect, provided is method for treating an indolent CTCL, comprising administering to the individual an anti-KIR3DL2 binding agent.

In embodiment, provided is a method of treating CTCL, the method comprising: (a) assessing the stage and/or disease prognosis of CTCL in an individual having a CTCL; and (b) if the individual has a stage II or III disease, optionally IIB, IIIA or IIIB, administering to the individual an anti-KIR3DL2 binding agent.

In one aspect, provided is method for treating a stage CTCL, comprising administering to the individual an anti-KIR3DL2 binding agent. In one aspect, provided is method for treating a stage II CTCL, comprising administering to the individual an anti-KIR3DL2 binding agent. In one aspect, provided is method for treating a stage III CTCL, comprising administering to the individual an anti-KIR3DL2 binding agent.

In one aspect, provided is method for treating a CTCL in an individual having less than B2 stage peripheral blood involvement, comprising administering to the individual an anti-KIR3DL2 binding agent. Optionally, the individual lacks or has low blood tumor burden, optionally wherein the individual has B0 (absence of significant blood involvement, e.g. ≤5% of peripheral blood lymphocytes are atypical (Sézary) cells) or B1 (low blood-tumor burden, e.g. >5% of peripheral blood lymphocytes are atypical (Sézary) cells, does not meet the criteria of B2) peripheral blood involvement.

In one aspect of any of the above, an individual having a CTCL has a skin lesion, optionally significant or advanced skin disease, optionally T2 (patches, papules, or plaques covering ≥10% of the skin surface, optionally further T2a (patch only) or T2b (plaque±patch), T3 (at least one tumor (1 cm diameter) or T4 stage skin involvement erythema covering ≥80% of body surface area). In one embodiment, the individual has multiple and/or high skin tumor burden. In one embodiment, the individual has one or multiple skin tumors greater than 1 cm diameter.

In one aspect of any of the above, an individual having a CTCL has patches, papules, or plaques covering ≥10% of the skin surface. In one aspect of any of the above, an individual having a CTCL has least one tumor ≥1 cm diameter. In one aspect of any of the above, an individual having a CTCL has erythema covering ≥80% of body surface area.

In embodiment, provided is a method of treating CTCL, the method comprising: (a) assessing the stage and/or disease prognosis of CTCL in an individual having a CTCL; and (b) if the individual has a stage IV disease, optionally IVA1 or IVA2 disease, optionally IVB disease, administering to the individual an anti-KIR3DL2 binding agent.

It will be appreciated that a treatment method of the disclosure may or may not involve a step of characterizing the CTCL prior to treatment. In embodiment, provided is a method of treating CTCL, the method comprising: (a) determining whether an individual has a CTCL comprising skin manifestation of CTCL (e.g. erythroderma, skin lesions or tumors), optionally a skin manifestation characterized by pathogenic KIR3DL2-expressing cells; and (b) if the individual has skin manifestations of CTCL, optionally a skin manifestation characterized by pathogenic KIR3DL2-expressing cells, administering to the individual an anti-KIR3DL2 binding agent. Optionally, the step of determining whether an individual has a CTCL comprising skin manifestation of CTCL comprises characterizing the extent of skin lesions; optionally, if the individual has plaques and/or ulcerating tumors, administering to the individual an anti- KIR3DL2 binding agent. Optionally, the step of determining whether an individual has a CTCL comprising skin manifestation of CTCL comprises characterizing the stage of skin disease, e.g. T2, T3, or T4 disease. Optionally, if the individual has advanced skin manifestations of CTCL, e.g., T2, T3, or T4 disease, administering to the individual an anti-KIR3DL2 binding agent.

In embodiment, provided is a method of treating CTCL, the method comprising: (a) assessing the stage and/or disease prognosis of CTCL in an individual having a CTCL; and (b) if the individual has an indolent CTCL, administering to the individual an anti-KIR3DL2 binding agent.

It will be appreciated that a treatment method of the disclosure may or may not involve a step of characterizing tumor cells for KIR3DL2-expression prior to treatment. In embodiment, provided is a method of treating CTCL, the method comprising: (a) determining whether skin manifestation of CTCL in an individual comprise pathogenic KIR3DL2-expressing cells (e.g. KIR3DL2-expressing cells in erythroderma and/or skin lesions); and (b) if the individual has skin manifestations of CTCL comprising pathogenic KIR3DL2-expressing cells, administering to the individual an anti-KIR3DL2 binding agent.

It will be appreciated that a treatment method of the disclosure may or may not involve a step of characterizing tumor cells for KIR3DL2-expression prior to treatment. In embodiment, provided is a method of treating CTCL, the method comprising: (a) obtaining a blood sample or biopsy (e.g. skin biopsy) from an individual and determining whether the sample comprises pathogenic KIR3DL2-expressing cells (KIR3DL2+ tumor cells); and (b) if the sample comprises pathogenic KIR3DL2-expressing cells, administering to the individual an anti-KIR3DL2 binding agent. In another embodiment, provided is a method of treating CTCL, the method comprising: (a) obtaining a blood sample from an individual and determining whether the sample comprises pathogenic KIR3DL2-expressing cells (KIR3DL2+ tumor cells); and (b) if the sample does not comprise detectable pathogenic KIR3DL2-expressing cells, administering to the individual an anti-KIR3DL2 binding agent.

Optionally the method further comprises determining whether disease cells also express other markers of abnormal lymphocytes at their surface, for example determining whether cells are CD4, CD30, CD3, CD8 cells.

In some aspects, an anti-KIR3DL2 binding agent can be administered to an individual who is in remission following treatment for CTCL or who has having otherwise responded positively to a first (one or more) anti-CTCL therapy (i.e. with a non-KIR3DL2), optionally having a low blood-tumor burden.

In some aspects, the anti-KIR3DL2 binding agent can be administered to an individual having a poor disease prognosis and/or who has relapsed, is resistant or is not responsive to therapy with a first (one or more) therapeutic agent.

Provided herein are treatment regimens that can be used for treatment of both CTCL with low or no blood tumor burden (and/or without detectable KIR3DL2+ tumor cells), or in CTCL with blood involvement or with high blood tumor burden (and/or with detectable KIR3DL2+ tumor cells). It will be appreciated, however, that the regimens can also be used for one or the other subgroup separately.

In one embodiment, optionally an anti-KIR3DL2 binding agent is administered in low doses, optionally in an amount that is designed to be below that would maintain full receptor occupancy on tumor cells in skin disease (e.g. erythroderma, skin lesions or tumors) in all patients, including those with high blood and skin tumor burden; such a dose may have the advantageous properties of giving rise to a broader anti-tumor response through depletion of a small number of KIR3DL2-expressing tumor cells in circulation (e.g., below the detection limit), for example tumor cells that enter circulation from skin tumors, and/or of giving rise to a broader anti-tumor response through the induction of antibody-dependent cellular phagocytosis (ADCP) in skin tumors. In one embodiment, the doses of anti-KIR3DL2 binding agent are repeated, in particular, the treatment comprises a first, second, and optionally further administration of an anti-KIR3DL2 binding agent. Optionally, the schedule of administration (e.g. the time between two successive administrations) and dose are chosen so as to maintain a trough level of anti-KIR3DL2 binding agent that provides a concentration in blood (e.g., blood serum) that corresponds to at least the $EC_{10}$, the $EC_{60}$, the $EC_{80}$, the $EC_{90}$, or the $EC_{100}$ for NK lytic capacity.

In some embodiments, an anti-KIR3DL2 agent is administered in an dose and frequency so as to obtain and/or maintain a concentration in blood (e.g., blood serum) that corresponds to at least the $EC_{10}$ for NK lytic capacity, optionally at about or at least about, the $EC_{60}$, the $EC_{80}$, the $EC_{90}$, or the $EC_{100}$.

Optionally, in any embodiment herein, the amount and frequency of anti-KIR3DL2 agent is less than that which provides a concentration in blood (e.g., blood serum) that corresponds to that provided by 25 mg/kg, 20 mg/kg, 15 mg/kg, 10 mg/kg, 7.5 mg/kg or 6 mg/kg body weight, when administered weekly. Optionally, in any embodiment herein, an amount or dose of anti-KIR3DL2 agent administered can be specified to be less than 25 mg/kg, 20 mg/kg or 15 mg/kg body weight.

In another embodiment of any aspect herein, a treatment method is a method of reducing or preventing progression, maintaining remission, or preventing relapse of CTCL or preventing relapse of lymphoma in CTCL. In another embodiment of any aspect herein, a treatment method is a method of increasing the likelihood of survival over a relevant period. In another embodiment of any aspect herein, a treatment method is a method of improving the quality of life in an individual. In another embodiment of any aspect herein, a treatment method is a method of reducing the number of circulating lymphoma cells (e.g. Sezary cells) in an individual. In another embodiment of any aspect herein, a treatment method is a method of reducing blood tumor burden in an individual.

In another embodiment of any aspect herein, a treatment method is a method of preventing progression of an early stage CTCL to a more advanced stage of CTCL. In another embodiment of any aspect herein, a treatment method is a method of preventing progression of an early stage I, II or III CTCL to a stage IV CTCL. In another embodiment of any aspect herein, a treatment method is a method of preventing progression of a CTCL without blood tumors or with low blood tumor burden to a CTCL with blood tumor burden or high blood tumor burden. In another embodiment of any aspect herein, a treatment method is a method of preventing progression of a CTCL with B0 or B1 blood tumor burden to a CTCL with B2 blood tumor burden.

Delivering an anti-KIR3DL2 agent (e.g. an antibody or fragment thereof) to a subject (either by direct administration as an isolated proteinaceous binding agent, by administration as a cell such as a CAR effector cell that expresses an anti-KIR3DL2 binding protein at its surface, or by expression of a proteinaceous binding agent from a nucleic acid therein, such as from a pox viral gene transfer vector comprising anti-KIR3DL2 antibody-encoding nucleic acid sequence(s)) and practicing the other methods herein can be used to reduce, treat, prevent, or otherwise ameliorate any suitable aspect of CTCL as disclosed herein. The treatments can be administered parenterally, e.g. intravenously, and can be particularly useful in the reduction and/or amelioration of proliferation of abnormal lymphocytes in skin lesions, restoration of normal skin structure and strong reduction of pathogenic T cells.

In certain embodiment herein, a KIR3DL2-binding agent is administered to an individual for at least one administration cycle in which the agent is administered at least twice in an amount that provides a concentration in blood (e.g., blood serum) that corresponds to at least the $EC_{10}$, the $EC_{60}$, the $EC_{80}$, the $EC_{90}$, or the $EC_{100}$ for NK lytic capacity. Optionally, the agent is administered in an amount effective to achieve, and/or to maintain between two successive administrations of the agent, a concentration that provides a concentration in blood (e.g., blood serum) that corresponds to at least the $EC_{10}$, the $EC_{60}$, the $EC_{80}$, the $EC_{90}$, or the $EC_{100}$ for NK lytic capacity. Optionally, the administration cycle comprises at least a first and second (and optionally a $3^{rd}$, $4^{th}$, $5^{th}$, $6^{th}$, $7^{th}$, and/or $8^{th}$ or further) administration of the agent. Optionally, the agent is administered intravenously. Optionally the treatment has a duration of at least 10 weeks, 2 months, 3 months, 4 months or 6 months.

In one aspect of any embodiment herein, a KIR3DL2-binding agent is administered to an individual in an amount that provides (e.g. achieves and/or maintains) a concentration in blood (e.g., blood serum) that is at least the $EC_{10}$, the $EC_{60}$, the $EC_{80}$, the $EC_{90}$, or the $EC_{100}$ for NK lytic capacity.

In one aspect of any embodiment herein, a KIR3DL2-binding agent is administered to an individual in an amount that maintains for at least 1 week, at least 2 weeks, at least 1 month or at least 2 months, a concentration in blood (e.g., blood serum) that corresponds to between the $EC_{10}$ and the $EC_{70}$, between $EC_{10}$ and the $EC_{80}$, between $EC_{10}$ and the $EC_{90}$, or between $EC_{60}$ and the $EC_{100}$ for NK lytic capacity.

In one aspect of any embodiment herein, a KIR3DL2-binding agent is administered to an individual in an amount that is less than the amount that maintains substantially full KIR3DL2 occupancy on CTCL cells in skin (e.g. in skin lesions or tumors) between two successive administrations of the agent. In one aspect of any embodiment herein, a KIR3DL2-binding agent is administered to an individual in an amount that is less than the amount that maintains between two successive administrations of the agent a concentration in skin (e.g. in skin lesions or tumors) that corresponds to at least the $EC_{50}$, the $EC_{70}$, the $EC_{80}$, the $EC_{90}$, or the $EC_{100}$ for NK lytic capacity. In one aspect of any embodiment herein, an anti-KIR3DL2 antibody of human IgG isotype, optionally an antibody characterized by $EC_{50}$ in $^{51}$Cr-release assay for HuT78 tumor lysis by PBMC from healthy volunteers, of less than 100 ng/ml, optionally between 1 and 100 ng/ml, optionally between 1 and 50 ng/ml, optionally about 50 ng/ml, and is administered to an individual in an amount (e.g. administered weekly) that is less than 15, 20 or 30 mg/kg body weight.

In one aspect of any embodiment herein, a KIR3DL2-binding agent comprises an anti-KIR3DL2 antibody of human IgG isotype, optionally an antibody characterized by $EC_{50}$ in $^{51}$Cr-release assay for HuT78 tumor lysis by PBMC from healthy volunteers, of less than 100 ng/ml, optionally between 1 and 100 ng/ml, optionally between 1 and 50 ng/ml, optionally about 50 ng/ml, and is administered to an individual in an amount effective to achieve (and/or to maintain for a specified period of time or between two successive administrations) a blood (serum) concentration of anti-KIR3DL2 antibody of at least 0.1 µg/ml (or, optionally at least 0.4, 1, 2 or 10 µg/mL). In one embodiment, the antibody is administered once per week, once every two weeks, once every three weeks, once per month, optionally between once per month and once every two months intravenously. In one embodiment, the antibody is administered to an individual in an amount effective to maintain between two successive administrations) a blood (serum) concentration of anti-KIR3DL2 antibody of at least 7 ng/ml (e.g. 10% lytic capacity), optionally at least 70 ng/ml (e.g. 60% lytic capacity), optionally at least 0.4 µg/ml (e.g. 80% lytic capacity), optionally at least 2 µg/ml (e.g. 90% lytic capacity), optionally at least 10 µg/ml (e.g. 100% lytic capacity), or optionally at least 20 µg/ml, 50 µg/ml or 80 µg/ml.

In one aspect of any embodiment herein, a KIR3DL2-binding agent comprises an anti-KIR3DL2 antibody of human IgG isotype and is administered to an individual in an amount effective to maintain for a specified period of time or between two successive administrations) a minimum (trough) blood (serum) concentration of anti-KIR3DL2 antibody of between 0.1-0.5 µg/ml, optionally between 0.4-2 µg/ml, optionally between 2-7 µg/ml, optionally between 2-10 µg/ml, optionally between 2-50 µg/ml, optionally between 10 and 20 µg/ml, optionally between 20 and 50 µg/ml, or optionally between 50 and 100 µg/ml. In one embodiment, the antibody is administered once per month, optionally between once per month and once every two months intravenously.

The amount of antibody required to achieve a particular blood concentration can be determined based on the properties of the particular antibody. In one aspect of any embodiment herein, a KIR3DL2-binding agent comprises an anti-KIR3DL2 antibody of human IgG isotype, optionally an antibody characterized by $EC_{50}$ in $^{51}$Cr-release assay for HuT78 tumor lysis by PBMC from healthy volunteers comparable to that of an anti-KIR3DL2 antibody disclosed herein (e.g., having an $EC_{50}$ that is lower or within 1-log or 0.5-log of the $EC_{50}$ of that of an antibody disclosed herein (e.g. a 2B12 antibody), optionally an $EC_{50}$ of less than 100 ng/ml, optionally between 1 and 100 ng/ml, optionally between 1 and 50 ng/ml, optionally about 50 ng/ml. In one aspect of any embodiment herein, the KIR3DL2-binding agent is administered to an individual intravenously at a dose of between 0.1-0.75 mg/kg, optionally 0.2-0.75 mg/kg, optionally 0.4-1 mg/kg, optionally 0.75-1.5 mg/kg, optionally about 0.01 mg/kg, optionally about 0.2 mg/kg, optionally about 0.75 mg/kg, or optionally about 1.5 mg/kg body weight. In one embodiment, the antibody is administered once per month, optionally between once per month and once every two months intravenously, at a dose of between 0.1-0.75 mg/kg, optionally 0.2-0.75 mg/kg, optionally 0.4-1 mg/kg, optionally 0.75-1.5 mg/kg, optionally about 0.01 mg/kg, optionally about 0.2 mg/kg, optionally about 0.75 mg/kg, optionally about 1 mg/kg, or optionally about 1.5 mg/kg body weight.

In one aspect of any embodiment herein, the KIR3DL2-binding agent is administered to an individual intravenously at a dose of between 0.75 and 10 mg/kg, optionally between 0.75-1.5 mg/kg, optionally between 1-3 mg/kg, optionally 1.5-3 mg/kg, optionally 3-6 mg/kg, optionally 6-10 mg/kg, optionally about 1 mg/kg, optionally about 1.5 mg/kg, optionally about 3 mg/kg, optionally about 6 mg/kg, or optionally about 10 mg/kg body weight. In one embodiment, the antibody is administered once per week (optionally once per 2 weeks), or between once per week and once per month (or every 4 weeks), intravenously, at a dose of between 1-3 mg/kg, optionally 1.5-3 mg/kg, optionally 3-6 mg/kg, optionally 1.5-8 mg/kg, optionally 6-10 mg/kg, optionally about 1 mg/kg, optionally about 1.5 mg/kg, optionally about 3 mg/kg, optionally about 4 mg/kg, optionally about 6 mg/kg, optionally less than 10 mg/kg body weight, or optionally about 10 mg/kg body weight.

In one aspect of any embodiment herein, the KIR3DL2-binding agent is administered to an individual intravenously at a dose of between 1-3 mg/kg, optionally 1.5-3 mg/kg, optionally 3-6 mg/kg, optionally 6-10 mg/kg, optionally about 1 mg/kg, optionally about 1.5 mg/kg, optionally about 3 mg/kg, optionally about 6 mg/kg, or optionally about 10 mg/kg body weight. In one embodiment, the antibody is administered between once per month and once every two months intravenously at a dose of between 1-3 mg/kg, optionally 1.5-3 mg/kg, optionally 3-6 mg/kg, optionally 6-10 mg/kg, optionally about 1 mg/kg, optionally about 1.5 mg/kg, optionally about 3 mg/kg, optionally about 6 mg/kg, optionally less than 10 mg/kg body weight, or optionally about 10 mg/kg body weight.

In any embodiment, a mg/kg dose can be expressed as a fixed dose equivalent of any of the doses using for example a body weight of 65 kg or 75 kg, e.g., a fixed dose equivalent of 10 mg/kg can be defined as 750 mg.

In one embodiment, provided is a method of treating a CTCL in an individual (e.g. an individual having a CTCL as described herein), the method comprising administering to the individual a KIR3DL2-binding agent for at least one administration cycle in which the agent is administered at least twice in an amount that provides a concentration in blood (e.g., blood serum) that is at least the $EC_{10}$, the $EC_{60}$, the $EC_{80}$, the $EC_{90}$, or the $EC_{100}$ for NK lytic capacity. Optionally, the agent is administered in an amount effective to achieve, and/or to maintain between two successive administrations of the agent, a concentration that provides a concentration in blood (e.g., blood serum) that is at least the $EC_{10}$, the $EC_{60}$, the $EC_{80}$, the $EC_{90}$, or the $EC_{100}$ for NK lytic capacity. Optionally, the administration cycle comprises at least a first and second (and optionally a $3^{rd}$, $4^{th}$, $5^{th}$, $6^{th}$, $7^{th}$, and/or $8^{th}$ or further) administration of the agent. Optionally, the agent is administered intravenously.

Optionally, treatment regimens can comprise an induction cycle. For example, a regimen for an anti-KIR3DL2 antibody of human IgG isotype, optionally an antibody characterized by $EC_{50}$ in $^{51}Cr$-release assay for HuT78 tumor lysis by PBMC from healthy volunteers comparable to that of an anti-KIR3DL2 antibody disclosed herein (e.g., having an $EC_{50}$ that is lower or within 1-log or 0.5-log of the $EC_{50}$ of that of a 2B12 antibody disclosed herein; optionally, an antibody characterized by $EC_{50}$ in $^{51}Cr$-release assay for HuT78 tumor lysis by PBMC from healthy volunteers of less than 100 ng/ml, optionally between 1 and 100 ng/ml, optionally between 1 and 50 ng/ml, optionally about 50 ng/ml, can comprise:

(a) an induction treatment cycle comprising a plurality of administrations of the antibody, wherein the antibody is administered to an individual intravenously in an amount effective to maintain for a specified period of time or between two successive administrations) a minimum (trough) blood (serum) concentration of anti-KIR3DL2 antibody of at least 50, 80, 90, 100, 200 or 300 µg/ml, optionally between 50 and 200 µg/ml, optionally between 50 and 100 µg/ml, followed by:

(b) a treatment cycle comprising a plurality of administrations of the antibody, wherein the antibody is administered to the individual intravenously in an amount effective to maintain for a specified period of time or between two successive administrations) a minimum (trough) blood (serum) concentration of anti-KIR3DL2 antibody of less than 100 µg/ml, optionally less than 50 µg/ml, optionally at least 0.1-0.5 µg/ml, optionally between 0.4-2 µg/ml, optionally between 2-7 µg/ml, optionally between 2-10 µg/ml, optionally between 2-50 µg/ml, optionally between 10 and 20 µg/ml, optionally between 20 and 50 µg/ml. In one embodiment, the amount administered in the treatment cycle (b) is the same amount administered in the treatment cycle (a) but at lesser frequency of administration.

In another exemplary treatment regimen for an anti-KIR3DL2 antibody of human IgG isotype, the treatment comprises:

(a) an induction treatment cycle comprising a plurality (e.g. at least 2, 4, 8, or 10) of administrations of the antibody, wherein the antibody is administered to an individual intravenously at a dose of between 1-20 mg/kg, optionally 1-10 mg/kg, optionally 1-3 mg/kg, optionally 1.5-3 mg/kg, optionally 3-6 mg/kg, optionally 6-10 mg/kg, optionally about 1 mg/kg, optionally about 1.5 mg/kg, optionally about 3 mg/kg, optionally about 6 mg/kg, or optionally about 10 mg/kg body weight at a frequency of about 2, 3 or 4 times per month, optionally once per week, followed by:

(b) a treatment cycle (e.g. maintenance cycle) comprising a plurality of (e.g. at least 2, 4, 8, or 10) administrations of the antibody, wherein the antibody is administered to the individual intravenously at a dose of between 1-20 mg/kg, optionally 1-10 mg/kg, optionally 1-3 mg/kg, optionally 1.5-3 mg/kg, optionally 3-6 mg/kg, optionally 6-10 mg/kg, optionally about 1 mg/kg, optionally about 1.5 mg/kg, optionally about 3 mg/kg, optionally about 6 mg/kg, or optionally about 10 mg/kg body weight at a frequency of about once every 1-3 months, optionally about once per month. In one embodiment, the dose (e.g. 1, 1.5, 3, 6 or 10 mg/kg) administered in the treatment cycle (b) is the same dose administered in the treatment cycle (a).

In one embodiment, a common treatment regimen (e.g. same dosage and same frequency of administration) that does not result in healthy NK and/or T cell depletion can advantageously be employed in individuals irrespective of initial tumor burden and/or disease stage, wherein the common treatment regimen is preceded by an induction regimen or loading period in which anti-KIR3DL2 antibody is administered to an individual (e.g. an individual having a high tumor burden) at a higher administration frequency (optionally wherein the doses at each administration of antibody in the common treatment regimen and the induction regimen are the same.

In one embodiment, provided is a method of treating an individual having a cancer (e.g. a solid tumor), the method comprising administering to the individual an anti-KIR3DL2 antibody of human IgG isotype, for at least one administration cycle, wherein the method comprises:

a. an induction period (or cycle) in which antibody is administered in a plurality of successive intravenous administrations, in a dose of between 0.75 and 10 mg/kg body weight, at a frequency of 2-4 administrations per month (e.g. one administration per week), and
 b. a maintenance period (or cycle) in which the antibody is administered in a plurality of successive intravenous administrations, in a dose of between 0.75 and 10 mg/kg body weight, at a frequency of one administration every one or two months (e.g. one administration per week). In one embodiment, the first administration within the maintenance period occurs no more than one month after the last dose of the loading period. In one embodiment, the dose at each administration in the induction cycle of (a) and at each administration in the maintenance period of (b) is the same (e.g. 0.75 mg/kg, 1.5 mg/kg, 6 mg/kg or 10 mg/kg are used both in the induction cycle and the maintenance period).

In one embodiment of any of the treatments comprising an induction cycle or period, the induction period comprises 4, 5, 6, 7, 8 or more administrations. In one embodiment, the following (e.g. maintenance) period comprises at least 2, 3, 4, 5, 6, 7 or 8 administrations. In one embodiment, the antibody is administered at the same dose in both the loading period and the maintenance period. In one embodiment, the induction period and the maintenance period each comprise administering the antibody in a dose of 0.75 mg/kg body weight. In one embodiment, the induction period and the maintenance period each comprise administering the antibody in a dose of 1.5 mg/kg body weight. In one embodiment, the induction period and the maintenance period each comprise administering the antibody in a dose of 3 mg/kg body weight. In one embodiment, the induction period and the maintenance period each comprise administering the antibody in a dose of 6 mg/kg body weight. In one embodiment, the induction period and the maintenance period each comprise administering the antibody in a dose of 10 mg/kg body weight. In one embodiment, the antibody comprises a heavy chain variable region comprising an amino acid sequence of SEQ ID NO: 31; and a light chain variable region comprising an amino acid sequence of SEQ ID NO: 25. In one embodiment, the antibody comprises a heavy chain variable region comprising an amino acid sequence of SEQ ID NO: 31; and a light chain variable region comprising an amino acid sequence of SEQ ID NO: 26.

Optionally, the treatment of the disclosure does not cause depletion of KIR3DL2-expressing healthy immune cells (e.g. NK cells, CD8 T cells, gammadelta T cells). Optionally, the amount of agent is an amount effective to give rise to a broader anti-tumor response through depletion of KIR3DL2-expressing tumor cells in circulation (e.g., where such cells are few or below the detection limit, e.g. in an individual having low/no blood tumor burden), for example tumor cells that enter circulation from skin lesions. Optionally, the amount of agent is an amount effective to give rise to a broader anti-tumor response through the induction of antibody-dependent cellular phagocytosis (ADCP) in skin lesions.

In one aspect, any of the treatment regimens herein are used for the treatment of individuals having CTCL, wherein the treatment regimen (e.g. the same dose of anti-KIR3DL2 agent and frequency of administration) is used in individuals having SS and in individuals having MF.

In one aspect, any of the treatment regimens herein are used for the treatment of individuals having CTCL, wherein the treatment regimen (e.g. the same dose of anti-KIR3DL2 agent and frequency of administration) is used in individuals having indolent disease and in individuals having aggressive disease.

In one aspect, any of the treatment regimens herein are used for the treatment of individuals having CTCL, wherein the treatment regimen (e.g. the same dose of anti-KIR3DL2 agent and frequency of administration) is used in individuals lacking detectable KIR3DL2-expressing malignant cells (e.g. KIR3DL2-expressing Sézary cells) in circulation, and in individuals having detectable KIR3DL2-expressing malignant cells (e.g. KIR3DL2-expressing Sézary cells) in circulation.

In one aspect, any of the treatment regimens herein are used for the treatment of individuals having CTCL, wherein the treatment regimen (e.g. the same dose of anti-KIR3DL2 agent and frequency of administration) is used in individuals having low numbers of detectable KIR3DL2-expressing malignant cells (e.g. KIR3DL2-expressing Sézary cells) in circulation, and in individuals having high numbers of detectable KIR3DL2-expressing malignant cells (e.g. KIR3DL2-expressing Sézary cells) in circulation.

In one aspect, any of the treatment regimens herein are used for the treatment of individuals having CTCL, wherein the treatment regimen (e.g. the same dose of anti-KIR3DL2 agent and frequency of administration) is used in individuals having low or no blood tumor burden, and in individuals having (or having high) blood tumor burden. In one embodiment, no or low tumor burden is B0 (absence of significant blood involvement, e.g. ≤5% of peripheral blood lymphocytes are atypical (Sézary) cells) or B1 (low blood-tumor burden, e.g. >5% of peripheral blood lymphocytes are atypical (Sézary) cells. In one embodiment, having blood tumor burden or having high blood tumor burden is B2 (high blood-tumor burden: ≥1,000/µL Sézary cells with positive clone).

In one aspect, any of the treatment regimens herein are used for the treatment of individuals having CTCL, wherein the treatment regimen (e.g. the same dose of anti-KIR3DL2 agent and frequency of administration) is used in individuals having early stage CTCL (e.g. stage I, II and/or III), and in individuals having late stage CTCL (e.g., stage IV).

In one aspect, any of the treatment regimens herein are used for the treatment of individuals having CTCL having skin lesions, optionally significant or advanced skin disease, optionally T2 (patches, papules, or plaques covering ≥10% of the skin surface, optionally further T2a (patch only) or T2b (plaque±patch), T3 (at least one tumor (≥1 cm diameter) or T4 stage skin involvement erythema covering ≥80% of body surface area). In one embodiment, the individual has multiple and/or high skin tumor burden. In one embodiment, the individual has one or multiple skin tumors greater than 1 cm diameter.

The anti-KIR3DL2 binding agent may be used in combined treatments with one or more other treatments or therapeutic agents, including treatments and agents normally utilized for the particular therapeutic purpose for which the agent is being administered. The additional treatment or agent will normally be administered in amounts and treatment regimens typically used for that treatment or agent in a monotherapy for the particular disease or condition being treated. In the treatment methods, the KIR3DL2-binding compound and the second therapeutic agent or treatment can be administered sequentially. The KIR3DL2-binding compound can be administered prior to the administration of the second therapeutic agent or treatment. For example, the KIR3DL2-binding compound can be administered approximately 0 to 30 days prior to the administration of the second therapeutic agent or treatment. In some embodiments, an KIR3DL2-binding compound is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days prior to the administration of the second therapeutic agent or treatment. In one embodiment, the treatment is a bone marrow transplant or hematopoietic stem cell transplant. In some embodiments, a KIR3DL2-binding compound is administered concurrently with the administration of the therapeutic agents.

In one embodiment, a subject receives treatment with the anti-KIR3DL2 agent prior to treatment with a bone marrow transplant or hematopoietic stem cell transplant. For example, a transplant can be administered within 1, 2 or 3 months following the end of treatment with the anti-KIR3DL2 agent.

In one embodiment with the anti-KIR3DL2 agent precedes treatment with an additional therapeutic agent or treatment for CTCL selected from the group consisting of: a corticosteroid, nitrogen mustard, carmustine, topical tacrolimus (Protopic®), imiquimod (Aldara®; 3M Inc.), topical retinoids, and rexinoids (bexarotene; Targretin®; Ligand Pharmaceuticals, San Diego, CA)), mogamulizumab, alemtuzumab, brentuximab vedotin, as well as ultraviolet light therapy (Psoralen+UVA (PUVA), narrowband UVB, and UVB), Photodynamic therapy (PDT) and body irradiation, histone deacetylase inhibitors such as vorinostat (suberoylanilide hydroxamic acid, Zolinza®) and Romidepsin (depsipeptide, FK-228, Istodax®), a cyclic peptide that selectively inhibits histone deacetylase isotypes 1, 2, 4 and 6, chemotherapy or combination chemotherapy, gemcitabine, antifolate analogues such as Pralatrexate (Folotyn®), IMiDs (immunomodulatory drugs), CC-5013 (lenalidomide; Revlimid®), CC-4047 (Actimid), and ENMD-0995, proteosome inhibitors and bortezomib (Velcade®). Anti-KIR3DL2 agent can be advantageously used in individuals who have not received one or more of (or any of) the above treatments.

In one embodiment, the anti-KIR3DL2 agent compositions optionally do not comprise a further therapeutic agent. In one embodiment, the anti-KIR3DL2 agent compositions may be employed as monotherapy, e.g., without the combined administration of another therapeutic agent for the particular therapeutic purpose for which the anti-KIR3DL2 agent is being administered, notably for the treatment of a CTCL.

KIR3DL2 Binding Agents

An agent that binds a KIR3DL2 polypeptide (used interchangeable with the terms Anti-KIR3DL2 agent, KIR3DL2-binding agent, anti-KIR3DL2 binding agent and the like) can be any agent suitable to bind KIR3DL2 and have the functionality in accordance with the disclosure.

KIR3DL2 (CD158k) is a disulphide-linked homodimer of three-Ig domain molecules of about 140 kD, described in Pende et al. (1996) J. Exp. Med. 184: 505-518, the disclosure of which is incorporated herein by reference. Several allelic variants have been reported for KIR3DL2 polypeptides, each of these are encompassed by the term KIR3DL2. The amino acid sequence of the mature human KIR3DL2 (allele *002) is shown in SEQ ID NO: 1, below, corresponding to Genbank accession no. AAB52520 in which the 21 amino acid residue leader sequence has been omitted:

```
                                          (SEQ ID NO: 1)
LMGGQDKPF LSARPSTVVP RGGHVALQCH YRRGFNNFML

YKEDRSHVPI FHGRIFQESF IMGPVTPAHA GTYRCRGSRP

HSLTGWSAPS NPLVIMVTGN HRKPSLLAHP GPLLKSGETV

ILQCWSDVMF EHFFLHRDGI SEDPSRLVGQ IHDGVSKANF

SIGPLMPVLA GTYRCYGSVP HSPYQLSAPS DPLDIVITGL

YEKPSLSAQP GPTVQAGENV TLSCSSWSSY DIYHLSREGE

AHERRLRAVP KVNRTFQADF PLGPATHGGT YRCFGSFRAL

PCVWSNSSDP LLVSVTGNPS SSWPSPTEPS SKSGICRHLH

VLIGTSVVIF LFILLLFFLL YRWCSNKKNA AVMDQEPAGD
```

```
RTVNRQDSDE QDPQEVTYAQ LDHCVFIQRK ISRPSQRPKT

PLTDTSVYTE LPNAEPRSKV VSCPRAPQSG LEGVF.
```

Also encompassed are any nucleic acid or protein that represent allelic variants of KIR3DL2 shown in SEQ ID NO: 1, for example KIR3DL2 proteins sharing at least 95%, 97%, 98%, 99%, or higher amino acid identity.

Closely related KIR3DL1 (CD158e1) is a monomeric molecule of about 70 kD, described in Colonna and Samaridis (1995) Science 268 (5209), 405-408. The cDNA encoding a KIR3DL1 (CD158e2) polypeptide (allele *00101) is shown in Genbank accession no. L41269; the encoded amino acid sequence is shown in Genbank accession no. AAA69870. In one embodiment, a KIR3DL1 polypeptide referred to herein is allele *00101.

KIR3DL2 binding agents can be readily derived from any suitable source, for example KIR3DL2 binding agents can be made from a variety of immunoglobulin or non-immunoglobulin scaffolds, for example affibodies based on the Z-domain of staphylococcal protein A, engineered Kunitz domains, monobodies or adnectins based on the 10th extracellular domain of human fibronectin III, anticalins derived from lipocalins, DARPins (designed ankyrin repeat domains, multimerized LDLR-A module, avimers or cysteine-rich knottin peptides. See, e.g., Gebauer and Skerra (2009) Current Opinion in Chemical Biology 13:245-255, the disclosure of which is incorporated herein by reference. In certain embodiments, a KIR3DL2 binding agent comprises an antibody (or an antibody fragment).

A KIR3DL2 binding agent (e.g. an antibody, an antibody fragment) for use in treating CTCL may for example be in the form of an isolated protein, or it can be present on the surface of a cell (e.g. a CAR effector cell such as a T cell, NK cell or NKT cell) or encoded by a nucleic acid therein, such as from a pox viral gene transfer vector comprising anti-KIR3DL2 antibody-encoding nucleic acid sequence(s). A cell expressing a chimeric antigen receptor (CAR) can be constructed. Examples of CARs are engineered to comprise an extracellular single chain antibody (scFv) fused to the intracellular signaling domain of the T cell antigen receptor complex zeta chain, and have the ability, when expressed in effector cells such as T cells, NKT cells or NK cells, to redirect antigen recognition (i.e. KIR3DL2 recognition) based on the monoclonal antibody's specificity. In one aspect, provided are genetically engineered immune cells which express and bear on the cell surface membrane a KIR3DL2-specific chimeric immune receptor comprising an intracellular signaling domain, a transmembrane domain (TM) and a KIR3DL2-specific extracellular domain (e.g., a domain derived from variable heavy and light chain regions of the a monoclonal antibody that binds specifically to KIR3DL2, e.g. one of antibodies disclosed herein). Also provided are the KIR3DL2 specific chimeric immune receptors, DNA constructs encoding the receptors, and plasmid expression vectors containing the constructs in proper orientation for expression.

In one embodiment, the KIR3DL2-binding antibody is an antibody that directs ADCC and optionally further ADCP toward a KIR3DL2-expressing cell.

In one embodiment, the antibody used in any embodiment herein binds a KIR3DL2 polypeptide, optionally wherein the antibody does not substantially bind to a KIR3DL1 polypeptide, is characterized by binding affinity ($K_D$) for a human KIR3DL2 polypeptide of less than (better than) 100 ng/ml, optionally between 1 and 100 ng/ml.

The antibody is optionally characterized by an $EC_{50}$ in $^{51}Cr$-release assay for HuT78 tumor lysis by PBMC from healthy volunteers, of less than 100 ng/ml, optionally between 1 and 100 ng/ml, optionally between 1 and 50 ng/ml, optionally between 25 and 75 ng/ml, optionally about 50 ng/ml. The antibody is optionally characterized by an $EC_{50}$ in $^{51}Cr$-release assay for HuT78 tumor lysis by PBMC from healthy volunteers comparable to that of an anti-KIR3DL2 antibody disclosed herein (e.g., having an EC50 that is lower or within 1-log or 0.5-log of the EC50 of that of a 2B12 antibody disclosed herein having a VH of SEQ ID NO 31: and a VL of SEQ ID NOS: 25 or 26, comprising an Fc domain of wild type or modified human IgG1 isotype, and that mediates ADCC.

An exemplary anti-KIR3DL2 antibody can be characterized by an average disassociation constant ($K_D$) of less than $1\times10^{-9}$ M with respect to KIR3DL2, as determined by, e.g., surface plasmon resonance (SPR) screening (such as by analysis with a BIAcore™ SPR analytical device). Optionally, the anti-KIR3DL2 antibody has a KD of about $1\times10^{-8}$ M to about $1\times10^{-10}$ M, or about $1\times10^{-9}$ M to about $1\times10^{-11}$ M, for KIR3DL2.

In one aspect, an antibody that specifically binds KIR3DL2 can be characterized by having one or more (including any combination thereof, to the extent that such combination is not contradictory) of the following properties:

(a) has a Kd of less than $10^{-8}$ M, preferably less than $10^{-9}$ M, or preferably less than 10-10 M for binding to a KIR3DL2 polypeptide;
(b) binds to at least one residue in the segment corresponding to residues 1-98 or residues 193-292 of the KIR3DL2 polypeptide;
(c) competes for binding to a KIR3DL2 polypeptide with antibody 10F6, 2B12, 18C6, 9E10, 10G5, 13H1, 5H1, 1E2, 1C3 and/or 20E9;
(d) competes with a natural ligand of KIR3DL2 (e.g. a HLA polypeptide, optionally HLA-B27) for binding to a KIR3DL2 polypeptide (e.g. in a polypeptide interaction assay);
(e) does not substantially increase or induce internalization of KIR3DL2 polypeptides in KIR3DL2-expressing cells and/or is not internalized into KIR3DL2-expressing cells;
(f) does or does not inhibit KIR3DL2 signaling induced by a natural ligand of KIR3DL2 (e.g. a HLA polypeptide; HLA-B27);
(g) does not substantially bind to a KIR3DL1, KIR3DS1, KIR3DL3, KIR2DS1, KIR2DS2, KIR2DL3, KIR2DL1 and/or KIR2DS4 polypeptide;
(h) binds to an epitope comprising any one or more of amino acid residues R13, P14, S15, H23, A25, Q27, H32, G33, I60, G62, R78, L82, W226, I231 and/or R246 of a KIR3DL2 polypeptide; and
(i) has reduced binding to a KIR3DL2 polypeptide having a mutation at one or more of residues R13, P14, S15, H23, A25, Q27, H32, G33, I60, G62, R78, L82, W226, I231 and/or R246 of a KIR3DL2 polypeptide.

In any of the embodiments herein, an antibody may be characterized by any one or more features of (a)-(i), above. In any of the embodiments herein, an antibody may be characterized by the features of (a), (b), (c), and (g), further in combination with the features of (d) or (f), and optionally further the features of (e), above. Optionally, the antibody is further characterized by features (h) and/or (i).

In one embodiment, the antibody is human-suitable. In one embodiment the antibody is chimeric, e.g. contains variable regions of non-human or murine origin, and constant regions of human or non-murine origin. In one embodiment, the antibody is human or humanized.

In one embodiment the antibody comprises an Fc domain or is of an isotype that is bound by FcγR (e.g. FcγRIIIA), e.g. an antibody of IgG1 or IgG3 isotype.

Exemplary of antibodies that bind human KIR3DL2 include antibodies 19H12, 12B11, 10F6, 2B12, 18C6, 9E10, 10G5, 13H1, 5H1, 1E2, 1C3 or 20E9. These and further antibodies are provided in PCT/EP2013/069302 and PCT/EP2013/069293, both filed 17 Sep. 2013, the disclosures of which antibodies are incorporated herein by reference. These antibodies bind selectively to KIR3DL2 and do not bind KIR3DL1 (or KIR3DS1). While antibody 10F6, 2B12, 18C6, 9E10, 10G5, 13H1, 5H1, 1E2, 1C3 or 20E9 can be used, for example, as therapeutic agent administered to an individual for the depleting of a KIR3DL2 expressing target, e.g. by induction of ADCC toward a pathogenic KIR3DL2-expressing cell, antibody 12B11 and 19H12 will be advantageous for use in detection (e.g. in vitro assays) of KIR3DL2 expression on the surface of cells because 12B11 and 19H12 are particularly efficient in the detection of KIR3DL2-positive cells in detection assays, 12B11 is advantageous for immunohistochemistry assays using frozen tissue sections, while 19H12 is advantageous for flow cytometry detection.

The amino acid sequence of the heavy and light chain variable regions of antibodies 10F6, 2B12, 18C6, 9E10, 10G5, 13H1, 5H1, 1E2, 1C3 or 20E9 are listed in Table C. In a specific embodiment, an anti-KIR3DL2 antibody binds essentially the same epitope or determinant as any of monoclonal antibodies 10F6, 2B12, 18C6, 9E10, 10G5, 13H1, 5H1, 1E2, 1C3 or 20E9; optionally the antibody comprises an antigen binding region of antibody 10F6, 2B12, 18C6, 9E10, 10G5, 13H1, 5H1, 1E2, 1C3 or 20E9. In any of the embodiments herein, antibody 10F6, 2B12, 18C6, 9E10, 10G5, 13H1, 5H1, 1E2, 1C3 or 20E9 can be characterized by its amino acid sequence and/or nucleic acid sequence encoding it. In one embodiment, the monoclonal antibody comprises the Fab or F(ab')$_2$ portion of 10F6, 2B12, 18C6, 9E10, 10G5, 13H1, 5H1, 1E2, 1C3 or 20E9. A monoclonal antibody can comprise the heavy chain variable region of 10F6, 2B12, 18C6, 9E10, 10G5, 13H1, 5H1, 1E2, 1C3 or 20E9. According to one embodiment, the monoclonal antibody comprises the three CDRs of the heavy chain variable region of 10F6, 2B12, 18C6, 9E10, 10G5, 13H1, 5H1, 1E2, 1C3 or 20E9. A monoclonal antibody can further comprise the variable light chain variable region of 10F6, 2B12, 18C6, 9E10, 10G5, 13H1, 5H1, 1E2, 1C3 or 20E9 or one, two or three of the CDRs of the light chain variable region of 10F6, 2B12, 18C6, 9E10, 10G5, 13H1, 5H1, 1E2, 1C3 or 20E9. Optionally any one or more of said light or heavy chain CDRs may contain one, two, three, four or five or more amino acid modifications (e.g. substitutions, insertions or deletions). Optionally, any of the light and/or heavy chain variable regions comprising part or all of an antigen binding region of antibody 10F6, 2B12, 18C6, 9E10, 10G5, 13H1, 5H1, 1E2, 1C3 or 20E9 are fused to an immunoglobulin constant region of the human IgG type, optionally a human constant region, optionally a human IgG1 or IgG3 isotype.

In another aspect, an antibody comprises: a HCDR1 region of 10F6, 2B12, 18C6, 9E10, 10G5, 13H1, 5H1, 1E2, 1C3 or 20E9 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR2 region of 10F6, 2B12, 18C6, 9E10, 10G5, 13H1, 5H1, 1E2, 1C3 or 20E9 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a HCDR3 region of 10F6, 2B12, 18C6, 9E10, 10G5, 13H1, 5H1, 1E2, 1C3 or 20E9 comprising an amino acid sequence as set forth in Table A, or a sequence of at least 4, 5, 6, 7, 8, 9 or 10 contiguous amino acids thereof, optionally wherein one or more of these amino acids may be substituted by a different amino acid; a LCDR1 region of 10F6, 2B12, 18C6, 9E10, 10G5, 13H1, 5H1, 1E2, 1C3 or 20E9 comprising an amino acid sequence as set forth in Table B, or a sequence of at least 4, 5, 6, 7, 8, 9 or 10 contiguous amino acids thereof, optionally wherein one or more of these amino acids may be substituted by a different amino acid; a LCDR2 region of 10F6, 2B12, 18C6, 9E10, 10G5, 13H1, 5H1, 1E2, 1C3 or 20E9 comprising an amino acid sequence as set forth in Table B, or a sequence of at least 4, 5, 6, 7, 8, 9 or 10 contiguous amino acids thereof, optionally wherein one or more of these amino acids may be substituted by a different amino acid; a LCDR3 region of 10F6, 2B12, 18C6, 9E10, 10G5, 13H1, 5H1, 1E2, 1C3 or 20E9 comprising an amino acid sequence as set forth in Table B, or a sequence of at least 4, 5, 6, 7, 8, 9 or 10 contiguous amino acids thereof, optionally wherein one or more of these amino acids may be deleted or substituted by a different amino acid. The HCDR1, 2, 3 and LCDR1, 2, 3 sequences can optionally be specified as all (or each, independently) being those of the Kabat numbering system (as indicated in Tables A and/or B for each CDR), those of the Chotia numbering system as indicated in Table A for each CDR), those of the IMGT numbering system as indicated in Table A for each CDR), or any other suitable numbering system.

TABLE A

| mAb | CDR definition | HCDR1 SEQ ID | HCDR1 Sequence | HCDR2 SEQ ID | HCDR2 Sequence | HCDR3 SEQ ID | HCDR3 Sequence |
|---|---|---|---|---|---|---|---|
| 10F6 | Kabat | 51 | IAGMQ | 54 | WINTHSGVPKYAEDFKG | 20 | GGDEGVMDY |
|  | Chotia | 52 | GYTFTI | 55 | WINTHSGVPK | 20 | GGDEGVMDY |
|  | AbM | 53 | GYTFTIAGMQ |  | WINTHSGVPK | 20 | GGDEGVMDY |
| 2B12 | Kabat | 18 | TAGMQ | 19 | WINSHSGVPKYAEDFK | 20 | GGDEGVMDY |
|  | Chotia | 56 | GYTFTT | 58 | WINSHSGVP | 59 | GGDEGVMDYW |
|  | AbM | 57 | GYTFTTAGMQ | 58 | WINSHSGVP | 59 | GGDEGVMDYW |
| 10G5 | Kabat | 2 | SYTMH | 3 | YINPSSGYTENNRKF | 4 | RLGKGLLPPFDY |
|  | Chotia | 60 | GYTFTS | 62 | YINPSSGY | 63 | RLGKGLLPPFDY |
|  | AbM | 61 | GYTFTSYTMH |  | YINPSSGY |  | RLGKGLLPPFDY |
| 13H1 | Kabat | 64 | GYTMN | 67 | LINPYNGDTTYNQKFKG | 69 | ENWGYPYAMDY |
|  | Chotia | 65 | HYSFIG | 68 | LINPYNGDTT | 69 | ENWGYPYAMDY |
|  | AbM | 66 | LINPYNGDTTN | 68 | HYSFIGYTM | 69 | ENWGYPYAMDY |
| 1E2 | Kabat | 70 | DYAMN | 73 | VISTYYGDANYNQKFKG | 75 | IYYDYDGSY |
|  | Chotia | 71 | GYTFTD | 74 | VISTYYGDAN | 75 | IYYDYDGSY |
|  | AbM | 72 | GYTFTDYAMN | 74 | VISTYYGDAN | 75 | IYYDYDGSY |
| 9E10 | Kabat | 76 | SYTMH | 79 | YINPSSGYTDYNQKFKD | 81 | LGKGLLPPFDY |
|  | Chotia | 77 | GYTFTS | 80 | YINPSSGYTD | 81 | LGKGLLPPFDY |
|  | AbM | 78 | GYTFTSYTMH | 80 | YINPSSGYTD | 81 | LGKGLLPPFDY |
| 1C3 | Kabat | 82 | SYWMQ | 85 | AIYPGDGDTRYTQKFKG | 87 | RYDGYYHFDY |
|  | Chotia | 83 | GYTFTS | 86 | AIYPGDGDTR | 87 | RYDGYYHFDY |
|  | AbM | 84 | GYTFTSYWMQ | 86 | AIYPGDGDTR | 87 | RYDGYYHFDY |
| 20E9 | Kabat | 88 | TYWMQ | 91 | AIYPGDGDTRYTQKFKG | 93 | RGDYGNYGMDY |
|  | Chotia | 89 | GFTFTT | 92 | AIYPGDGDTR | 93 | RGDYGNYGMDY |
|  | AbM | 90 | GFTFTTYWMQ | 92 | AIYPGDGDTR | 93 | RGDYGNYGMDY |

TABLE B

| mAb | LCDR1 Sequence | LCDR2 Sequence | LCDR3 Sequence |
|---|---|---|---|
| 10F6 | 21 KASQDVSTAVA | 22 WASTRHT | 94 QQHYNTPWT |
| 2B12 | 21 KASQDVSTAVA | 22 WTSTRHT | 23 QQHYSTPWT |
| 10G5 | 5 RASENIYSNLA | 6 AATNLAD | 7 QHFWGTPYT |
| 13H1 | 95 RASESVDNFGISFMN | 96 AASNQGS | 97 QQSKEVPYT |
| 1E2 | 98 RSSQSLVHSNGNTYLH | 99 KVSNRFS | 100 SQSTHVPPYT |

TABLE B-continued

| mAb | LCDR1 Sequence | LCDR2 Sequence | LCDR3 Sequence |
|---|---|---|---|
| 9E10 | 101 KSNQNLLWSGNQRYCLV | 102 WTSDRYS | 103 QQHLHIPYT |
| 1C3 | 104 KSSQSLLWSVNQKNYLS | 105 GASIRES | 106 QHNHGSFLPLT |
| 20E9 | 107 RSSQSIVHSNGNTYLE | 108 KVSNHFS | 109 FQGSHVPPT |

TABLE C

| Antibody portion | | Amino acid sequence |
|---|---|---|
| 10F6 VH | 34 | QIQLVQSGPELKKPGETVRISCKASGY TFTIAGMQWVQKMPGKGLKWIGWINTH SGVPKYAEDFKGRFAFSLETSANIAYL QISNLKNEDTATYFCARGGDEGVMDYW GQGTSVTVS |
| 10F6 VL | 35 | DIVMTQSHKFMSTSVGDRVSITCKASQ DVSTAVAWYHQKPGQSPKLLIYWASTR HTGVPDRFSGSGSGTDYLTISALQAE DLALYYCQQHYNTPWTFGGGTKLEIK |
| 2B12 VH | 36 | QIQLVQSGPELKKPGETVRISCKASGY TFTTAGMQWVQKTPGKGLKWIGWINSH SGVPKYAEDFKGRFAFSLETSASTAYL QISTLKNEDTATYFCARGGDEGVMDYW GQGTSVTVS |
| 2B12 VL | 37 | DIVMTQSHKFMSTSLGDRVSFTCKASQ DVSTAVAWYQQKPGQSPKLLIYWTSTR HTGVPDRFTGSGSGTDYLTISSVQAE DLALYYCQQHYSTPWTFGGGTKLEIK |
| 10G5 VH | 38 | QVQLQQSAAELARPGASVKMSCKASGY TFTSYTMHWVKQRPGQGLEWIGYINPS SGYTENNRKFKDKTTLTADKSSSTAYM QLSSLTSEDSAVYYCARLGKGLLPPFD YWGQGTTLTVSSAKTTPPSVYPLAPGS AAQT |
| 10G5 VL | 39 | DIQMIQSPASLSVSVGETVTITCRASE NIYSNLAWYQQKQGKSPQLLVYAATNL ADGVPSRFSGSGSGTQYSLKINSLQSE DFGSYYCQHFWGTPYTFGGGTKLEIK |
| 13H1 VH | 40 | EVQLQQSGPELVKPGASMKISCKASHY SFIGYTMNWVKQRHGKNLEWIGLINPY NGDTTYNQKFKGKASLTVDKSSSTAYM EILSLTSEDSAVYYCARENWGYPYAMD YWGQGTSVTVS |
| 13H1 VL | 41 | DIVLTQSPASLAVSLGQRATISCRASE SVDNFGISFMNWFQQKPGQPPKLLIYA ASNQGSGVPARFSGSRSGTDFSLNIHP MEEDDTAMYFCQQSKEVPYTFGGGTKL EIK |
| 1E2 VH | 42 | QVQLQQSGAELVRPGVSVKISCKGSGY TFTDYAMNWVKQSHAKSLEWIGVISTY YGDANYNQKFKGKATMTVDKSSSTAYM ELARLTSEDSAIYYCALIYYDYDGSYW GQGTTLTVS |
| 1E2 VL | 43 | DVVMTQTPLSLPVSLGDQASISCRSSQ SLVHSNGNTYLHWYLQKPGQSPKLLIY KVSNRFSGVPDRFSGSGSGTDFTLKIS RVEAEDLGVYFCSQSTHVPPYTFGGGT KLEIK |

TABLE C-continued

| Antibody portion | | Amino acid sequence |
|---|---|---|
| 9E10 VH | 44 | Q V Q L Q Q S A A E L A R P G A S V K M S C K A S G Y T F T S Y T M H W V K Q R P G Q G L E W I G Y I N P S S G Y T D Y N Q K F K D K T T L T A D R S S S T A Y M Q L S S L T S E D S A V Y Y C A R L G K G L L P P F D Y W G Q G S T L T V S S |
| 9E10 VL1 | 45 | E I V L I Q S I P S L I V S A G E R V I I S C K S N Q N L L W S G N Q R Y C L V W H Q W K P G Q T P T P L I T W T S D R Y S G V P D R F I G S G S V I D F I L T I S S V Q A E D V A V Y F C Q Q H L H I P Y T F G G G T K L E I K |
| 9E10 VL2 | 46 | D I Q M I Q S P A S L S V S V G E T V T I T C R A S E N I Y S N L A W Y Q Q K Q G K S P Q L L V Y A A T N L A D G V P S R F S G S G S G T Q Y S L K I N S L Q S E D F G S Y Y C Q H F W G T P Y T F G G G T K L E I K |
| 1C3 VH | 47 | Q V Q L Q Q S G A E L A R P G A S V K L S C K A S G Y T F T S Y W M Q W V K Q R P G Q G L E W I G A I Y P G D G D T R Y T Q K F K G K A T L T A D K S S S T A Y M Q L S S L A S E D S A V Y Y C A R R Y D G Y Y H F D Y W G Q G T T L T V S |
| 1C3 VL | 48 | D I V M T Q S P S S L A V T A G E K V T M S C K S S Q S L L W S V N Q K N Y L S W Y Q Q K Q R Q P P K L L I Y G A S I R E S W V P D R F T G S G S G T D F T L T I S N V H A E D L A V Y Y C Q H N H G S F L P L T F G S G T K L E I K |
| 20E9 VH | 49 | Q V Q L Q Q S G A E V A R P G A S V K L S C K S S G F T F T T Y W M Q W V K Q R P G Q G L E W I G A I Y P G D G D T R Y T Q K F K G K A I L T A D K S S I T A Y M Q L S S L A S E D S A V Y Y C A R R G D Y G N Y G M D Y W G Q G T S V T V S S |
| 20E9 VL | 50 | D V L M T Q T P L S L P V S L G D Q A S I S C R S S Q S I V H S N G N T Y L E W Y L Q K P G Q S P K L L I Y K V S N H F S G V P D R F S G S G S G T D F T L K I S R V E A E D L G V Y Y C F Q G S H V P P T F G G G T K L E I K |

Examples of humanized VH and VL amino acid sequences of antibody 10G5 are shown in Table D and in SEQ ID NOS: 13-17 and 8-12, respectively. In one aspect, provided is an isolated humanized antibody that binds a human KIR3DL2 polypeptide, wherein the antibody comprises: a HCDR1 region comprising an amino acid sequence SYTMH as set forth in SEQ ID NO: 2, or a sequence of at least 3 or 4 amino acids thereof; a HCDR2 region comprising an amino acid sequence YINPSSGYTENNRKF as set forth in SEQ ID NO: 3, or a sequence of at least 4, 5, 6, 7, 8, 9 or 10 contiguous amino acids thereof; a HCDR3 region comprising an amino acid sequence LGKGLLPPFDY as set forth in SEQ ID NO: 4, or a sequence of at least 4, 5, 6, 7, 8, 9 or 10 contiguous amino acids thereof; a LCDR1 region comprising an amino acid sequence RASENIYSNLA as set forth in SEQ ID NO: 5, or a sequence of at least 4, 5, 6, 7, 8, 9 or 10 contiguous amino acids thereof; a LCDR2 region comprising an amino acid sequence AATNLAD as set forth in SEQ ID NO: 6, or a sequence of at least 3, 4 or 5 contiguous amino acids thereof; a LCDR3 region comprising an amino acid sequence QHFWGTPYT as set forth in SEQ ID NO: 7, or a sequence of at least 4, 5, 6, 7 or 8 contiguous amino acids thereof.

In one aspect, a humanized 10G5 antibody that binds a human KIR3DL2 polypeptide comprises:

(a) a CDR-H1 comprising the amino acid sequence of SEQ ID NO:2;
(b) a CDR-H2 comprising the amino acid sequence of SEQ ID NO:3;
(c) a CDR-H3 comprising the amino acid sequence of SEQ ID NO:4;
(d) a CDR-L1 comprising the amino acid sequence of SEQ ID NO:5;
(e) a CDR-L2 comprising the amino acid sequence of SEQ ID NO:6;
(f) a CDR-L3 comprising the amino acid sequence of SEQ ID NO:7; and
(g) human framework sequences.

In one embodiment, the humanized antibody comprises a heavy chain framework from the human subgroup VH1 together with JH6, optionally the antibodies comprises IGHV1-46*03, together with IGHJ6*01. In one embodiment, the humanized antibody comprises a light chain framework from the human subgroup VK1, optionally IGKV1-NL1*01.

Optionally the human framework comprises one or more mutations, e.g. back mutations that show a retain ability to bind KIR3DL2. Embodiments of the invention thus include the back-mutated 10G5 heavy chain variants having back mutations at any one or more (or any combination of) the following residues, using Abnum numbering:

10G5 VH: 5, 11, 12, 13, 20, 38, 40, 48, 66, 67, 69, 71, 72a, 75.

Abnum amino acid numbering nomenclature is described in Abhinandan and Martin, (2008) Molecular Immunology 45: 3832-3839, the disclosure of which is incorporated by reference). Sequence numbering using the Abnum system can also be automatically generated at Worldwide Web site: bioinfo.org.uk/abs/abnum. However it will be appreciated that the person of skill in the art can use an alternative numbering system and identify positions corresponding to Abnum numbering, for example the Kabat numbering system can be used (Kabat et al. (1991) Sequences of Protein of Immunological Interest, 5th ed., United States Public Health Service, National Institute of Health, Bethesda, MD).

Further embodiments of the invention thus include the back-mutated 10G5 light chain variants having back mutations at any one or more (or any combination of) the following residues:

10G5 VL: 17, 18, 40, 45, 48, 70, 76, 100.

The humanized antibody may further comprise one or more additional mutations (e.g. back-mutations) in the human framework sequences, to, e.g., enhance affinity, stability, or other properties of the humanized antibody.

In one aspect, a humanized 10G5 antibody that binds human KIR3DL2 polypeptide comprises:
(a) a CDR-H1 comprising the amino acid sequence of SEQ ID NO: 2;
(b) a CDR-H2 comprising the amino acid sequence of SEQ ID NO: 3;
(c) a CDR-H3 comprising the amino acid sequence of SEQ ID NO: 4;
(d) a CDR-L1 comprising the amino acid sequence of SEQ ID NO: 5;
(e) a CDR-L2 comprising the amino acid sequence of SEQ ID NO: 6;
(f) a CDR-L3 comprising the amino acid sequence of SEQ ID NO: 7; and
(g) human framework sequences, wherein a glutamine (Q) residue is present at position 39 of the VH domain and at position 38 of the VL domain. Optionally, the human framework sequences further comprise one or more back-mutations.

The glutamine (Q) residue at position 39 may exist naturally in the human VH framework sequence, or may be introduced by amino acid substitution or other modification of the sequence.

In another aspect, a humanized antibody may comprise a VH domain having at least about 80% sequence identity (e.g., at least about 85%, 90%, 95%, 97%, 98%, or more identity) to the VH domain of 10G5 of SEQ ID NOS: 13-17. In another particular aspect, a humanized antibody may comprise (a) a VH domain that comprises non-human CDR residues incorporated into a human VH domain, wherein the VH domain is at least about 80% (such as at least 90%, 95%, 97%, 98%) identical to a humanized 10G5 VH of SEQ ID NOS: 13-17, and (b) a VL domain that comprises non-human CDR residues incorporated into a human VL domain, wherein the VL domain is at least about 80% (such as at least 90%, 95%, 97%, 98%) identical to humanized 10G5 VL of SEQ ID NOS: 8-12.

Examples of humanized VH and VL amino acid sequences of antibody 2B12 are shown in Table D and in SEQ ID NOS: 24-28 and 30-33, respectively. In one aspect, a humanized antibody comprises: a HCDR1 region comprising an amino acid sequence TAGMQ as set forth in SEQ ID NO: 18, or a sequence of at least 3 or 4 contiguous amino acids thereof; a HCDR2 region comprising an amino acid sequence WINSHSGVPKYAEDFK as set forth in SEQ ID NO: 19, or a sequence of at least 4, 5, 6, 7, 8, 9 or 10 contiguous amino acids thereof; a HCDR3 region comprising an amino acid sequence GGDEGVMDY as set forth in SEQ ID NO: 20, or a sequence of at least, 5, 6, 7, or 8 contiguous amino acids thereof; a LCDR1 region comprising an amino acid sequence KASQDVSTAVA as set forth in SEQ ID NO: 21, or a sequence of at least 4, 5, 6, 7, 8, 9 or 10 contiguous amino acids thereof; a LCDR2 region comprising an amino acid sequence WTSTRHT as set forth in SEQ ID NO: 22, or a sequence of at least 3, 4 or 5 contiguous amino acids thereof; and/or a LCDR3 region comprising an amino acid sequence QQHYSTPWT as set forth in SEQ ID NO: 23, or a sequence of at least 4, 5, 6, 7, or 8 contiguous amino acids thereof.

In any of the embodiments herein, any of the CDRs 1, 2 and 3 of the heavy and light chains may be characterized by a sequence of at least 4, 5, 6, 7, 8, 9 or 10 contiguous amino acids thereof, and/or as having an amino acid sequence that shares at least 70%, 80%, 85%, 90% or 95% sequence identity with the particular CDR or set of CDRs listed in the corresponding SEQ ID NO.

In one aspect, a humanized 2B12 antibody comprises:
(a) a CDR-H1 comprising the amino acid sequence of SEQ ID NO: 18;
(b) a CDR-H2 comprising the amino acid sequence of SEQ ID NO: 19;
(c) a CDR-H3 comprising the amino acid sequence of SEQ ID NO: 20;
(d) a CDR-L1 comprising the amino acid sequence of SEQ ID NO: 21;
(e) a CDR-L2 comprising the amino acid sequence of SEQ ID NO: 22;
(f) a CDR-L3 comprising the amino acid sequence of SEQ ID NO: 23; and
(g) human framework sequences.

In one embodiment, a humanized antibody comprises a heavy chain framework from the human subgroup VH1 and/or VH7 together with JH6, optionally the antibodies comprises IGHV7-4-1*02 and/or IGHV1-c*01, together with IGHJ6*01. In one embodiment, a humanized antibody comprises a light chain framework from the human subgroup VK1 and/or VK4, optionally IGKV4-1*01 and/or IGKV1-39*01, together with JH4, optionally IGKJ4*01.

Optionally a human framework comprises one or more mutations, e.g. back mutations, for example. Optionally, a 2B12 heavy chain variant of the amino acid sequence below (SEQ ID NO: 29) can have back mutations at any one or more (or any combination of) the following residues, using Abnum numbering:

2B12 VH: 2, 38, 39, 40, 43, 48, 68, 72c, 91, 108.

(SEQ ID NO: 29)
QVQLVQSGSELKKPGASVKVSCKASGYTFTTAGMQWVRQAPGQGLEWMGW

INSHSGVPKYAEDFKGRFVFSLDTSVSTAYLQISSLKAEDTAVYYCARGG

DEGVMDYWGQGTTVTVSS.

Further embodiments of the invention thus include the back-mutated 2B12 light chain variants having back mutations at any one or more (or any combination of) the following residues:

2B12 VL: 3, 8, 9, 21, 43, 71, 78, 104.

The humanized antibody may further comprise one or more additional mutations (e.g. back-mutations) in the human framework sequences, to, e.g., enhance affinity, stability, or other properties of the humanized antibody.

In one aspect, a humanized 2B12 antibody comprises:
(a) a CDR-H1 comprising the amino acid sequence of SEQ ID NO: 18;
(b) a CDR-H2 comprising the amino acid sequence of SEQ ID NO: 19;
(c) a CDR-H3 comprising the amino acid sequence of SEQ ID NO: 20;
(d) a CDR-L1 comprising the amino acid sequence of SEQ ID NO: 21;
(e) a CDR-L2 comprising the amino acid sequence of SEQ ID NO: 22;
(f) a CDR-L3 comprising the amino acid sequence of SEQ ID NO: 23; and
(g) human framework sequences, wherein a glutamine (Q) residue is present at position 39 of the VH domain and at position 38 of the VL domain. Optionally, the human framework sequences further comprise one or more back-mutations.

In another aspect, humanized antibodies comprise a VH domain having at least about 80% sequence identity (e.g., at least about 85%, 90%, 95%, 97%, 98%, or more identity) to the VH domain of 2B12 or humanized 2B12 of SEQ ID NOS: 30-33. In another particular aspect, a humanized antibody comprises: (a) a VH domain that comprises non-human CDR residues incorporated into a human VH domain, wherein the VH domain is at least about 80% (such as at least 90%, 95%, 97%, 98%) identical to humanized 2B12 VH of SEQ ID NOS: 30-33, and (b) (a) a VL domain that comprises non-human CDR residues incorporated into a human VL domain, wherein the VL domain is at least about 80% (such as at least 90%, 95%, 97%, 98%) identical to humanized 2B12 VL of SEQ ID NOS: 24-28.

The glutamine (Q) residue at position 39 may exist naturally in the human VH framework sequence, or may be introduced by amino acid substitution or other modification of the sequence.

The 10G5 or 2B12 antibody may further comprise a native or engineered human IgG constant domain. Optionally the constant domain is an IgG1 domain, optionally further comprising a modification to increase Fc receptor binding.

TABLE D

| Antibody domain | Amino acid sequence (SEQ ID NO) |
|---|---|
| 10G5-L0 | DIQMTQSPSSLSASVGDRVTITCRASENTYSNLAWYQQKPGKAPKLLLYAATNLADGVPS RFSGSGSGTDYTLTISSLQPEDFATYYCQHFWGTPYTFGQGTKLEIK (SEQ ID NO: 8) |
| 10G5-L2 | DIQMTQSPSSLSASVGDRVTITCRASENTYSNLAWYQQKPGKAPQLLVYAATNLADGVPS RFSGSGSGTDYTLTISSLQPEDFATYYCQHFWGTPYTFGGGTKLEIK (SEQ ID NO: 9) |
| 10G5-L3 | DIQMTQSPSSLSASVGDRVTITCRASENTYSNLAWYQQKPGKAPQLLVYAATNLADGVPS RFSGSGSGTQYTLTISSLQPEDFATYYCQHFWGTPYTFGGGTKLEIK (SEQ ID NO: 10) |
| 10G5-L4 | DIQMTQSPSSLSASVGDRVTITCRASENTYSNLAWYQQKQGKAPQLLVYAATNLADGVPS RFSGSGSGTQYTLTINSLQPEDFATYYCQHFWGTPYTFGGGTKLEIK (SEQ ID NO: 11) |
| 10G5-L5 | DIQMTQSPSSLSASVGETVTITCRASENTYSNLAWYQQKQGKAPQLLVYAATNLADGVPS RFSGSGSGTQYTLTINSLQPEDFATYYCQHFWGTPYTFGGGTKLEIK (SEQ ID NO: 12) |
| 10G5-H0 | QVQLVQSGAEVKKPGASVKVSCKASGYTFTSYTMHWVRQAPGQGLEWMGYINPSSGYTEN NRKFKDRVTMTRDTSTSTVYMELSSLRSEDTAVYYCARLGKGLLPPFDYWGQGTTVTVSS (SEQ ID NO: 13) |
| 10G5-H3 | QVQLVQSGAEVKKPGASVKVSCKASGYTFTSYTMHWVRQAPGQGLEWIGYINPSSGYTEN NRKFKDKTTMTADTSTSTAYMELSSLRSEDTAVYYCARLGKGLLPPFDYWGQGTTVTVSS (SEQ ID NO: 14) |
| 10G5-H4 | QVQLQQSGAEVKKPGASVKMSCKASGYTFTSYTMHWVRQAPGQGLEWIGYINPSSGYTEN NRKFKDKTTLTADTSTSTAYMELSSLRSEDTAVYYCARLGKGLLPPFDYWGQGTTLTVSS (SEQ ID NO: 15) |
| 10G5-H5 | QVQLVQSGAELARPGASVKVSCKASGYTFTSYTMHWVRQAPGQGLEWIGYINPSSGYTEN NRKFKDKTTLTADKSTSTAYMELSSLRSEDTAVYYCARLGKGLLPPFDYWGQGTTVTVSS (SEQ ID NO: 16) |
| 10G5-H6 | QVQLQQSGAEVKKPGASVKMSCKASGYTFTSYTMHWVKQRPGQGLEWIGYINPSSGYTEN NRKFKDKTTLTADKSTSTAYMELSSLRSEDTAVYYCARLGKGLLPPFDYWGQGTTLTVSS (SEQ ID NO: 17) |
| 2B12-L0 | DIQMTQSPSFLSASVGDRVTITCKASQDVSTAVAWYQQKPGQPPKLLIYWTSTRHTGVPD RFSGSGSGTDFTLTISSLQAEDVAVYYCQQHYSTPWTFGGGTKVEIK (SEQ ID NO: 24) |
| 2B12-L1 | DIQMTQSPSFLSASVGDRVTITCKASQDVSTAVAWYQQKPGQPPKLLIYWTSTRHTGVPD RFSGSGSGTDYTLTISSLQAEDVAVYYCQQHYSTPWTFGGGTKVEIK (SEQ ID NO: 25) |
| 2B12-L2 | DIVMTQSPSFLSASVGDRVTITCKASQDVSTAVAWYQQKPGQPPKLLIYWTSTRHTGVPD RFSGSGSGTDYTLTISSVQAEDVAVYYCQQHYSTPWTFGGGTKVEIK (SEQ ID NO: 26) |

TABLE D-continued

| Antibody domain | Amino acid sequence (SEQ ID NO) |
|---|---|
| 2B12-L3 | DIVMTQSPSFLSASVGDRVTFTCKASQDVSTAVAWYQQKPGQSPKLLIYWTSTRHTGVPD RFSGSGSGTDYTLTISSVQAEDVAVYYCQQHYSTPWTFGGGTKVEIK (SEQ ID NO: 27) |
| 2B12-L4 | DIVMTQSHKFLSASVGDRVTFTCKASQDVSTAVAWYQQKPGQSPKLLIYWTSTRHTGVPD RFSGSGSGTDYTLTISSVQAEDVAVYYCQQHYSTPWTFGGGTKLEIK (SEQ ID NO: 28) |
| 2B12-H1 | QVQLVQSGSELKKPGASVKVSCKASGYTFTTAGMQWVQKSPGQGLEWMGWINSHSGVPKY AEDFKGRFVFSLDTSVSTAYLQISSLKAEDTAVYFCARGGDEGVMDYWGQGTTVTVSS (SEQ ID NO: 30) |
| 2B12-H2 | QIQLVQSGSELKKPGASVKVSCKASGYTFTTAGMQWVRQAPGQGLEWIGWINSHSGVPKY AEDFKGRFVFSLDTSVSTAYLQISSLKAEDTAVYFCARGGDEGVMDYWGQGTTVTVSS (SEQ ID NO: 31) |
| 2B12-H3 | QIQLVQSGSELKKPGASVKVSCKASGYTFTTAGMQWVQKSPGQGLEWIGWINSHSGVPKY AEDFKGRFAFSLDTSVSTAYLQISSLKAEDTAVYFCARGGDEGVMDYWGQGTTVTVSS (SEQ ID NO: 32) |
| 2B12-H4 | QIQLVQSGSELKKPGASVKVSCKASGYTFTTAGMQWVQKTPGKGLEWIGWINSHSGVPKY AEDFKGRFAFSLDTSASTAYLQISSLKAEDTAVYFCARGGDEGVMDYWGQGTSVTVSS (SEQ ID NO: 33) |

In one embodiment, a humanized 2B12 monoclonal antibody comprises:
(a) a heavy chain variable region comprising an amino acid sequence of SEQ ID NO: 31, and
(b) a light chain variable region comprising an amino acid sequence of SEQ ID NO: 25.

In one embodiment, a humanized 2B12 monoclonal antibody comprises:
(a) a heavy chain variable region comprising an amino acid sequence of SEQ ID NO: 31, and
(b) a light chain variable region comprising an amino acid sequence of SEQ ID NO: 26.

In one embodiment, a humanized 2B12 monoclonal antibody comprises:
(a) a heavy chain variable region comprising an amino acid sequence of SEQ ID NO: 32, and
(b) a light chain variable region comprising an amino acid sequence of SEQ ID NO: 26.

In one embodiment, a humanized 2B12 monoclonal antibody comprises:
(a) a heavy chain variable region comprising an amino acid sequence of SEQ ID NO: 33, and
(b) a light chain variable region comprising an amino acid sequence of SEQ ID NO: 26.

In one embodiment, a humanized 10G5 monoclonal antibody comprises:
(a) a heavy chain variable region comprising an amino acid sequence of SEQ ID NO: 13, and
(b) a light chain variable region comprising an amino acid sequence of SEQ ID NO: 8.

In one embodiment, a humanized 10G5 monoclonal antibody comprises:
(a) a heavy chain variable region comprising an amino acid sequence of SEQ ID NO: 14, and
(b) a light chain variable region comprising an amino acid sequence of SEQ ID NO: 9.

In one embodiment, a humanized 10G5 monoclonal antibody comprises:
(a) a heavy chain variable region comprising an amino acid sequence of SEQ ID NO: 15, and
(b) a light chain variable region comprising an amino acid sequence of SEQ ID NO: 9.

In one aspect, an anti-KIR3DL2 agent used in accordance with the methods of treatment herein binds to an epitope on a KIR3DL2 polypeptide that at least partially overlaps, or includes at least one residue in the segment corresponding to residues 1-192, residues 1-98, or residues 99-192 of the KIR3DL2 polypeptide of SEQ ID NO: 1 (or a subsequence thereof). In one embodiment, all key residues of the epitope is in a segment corresponding to residues 1-192, residues 1-98 or residues 99-192 of the KIR3DL2 polypeptide of SEQ ID NO: 1. In one embodiment, the antibodies bind an epitope comprising 1, 2, 3, 4, 5, 6, 7 or more residues in the segment corresponding to residues 1-192, 1-98 or 99-192 of the KIR3DL2 polypeptide of SEQ ID NO: 1. Preferably the residues bound by the antibody are present on the surface of the KIR3DL2 polypeptide.

In one aspect, an anti-KIR3DL2 agent used in accordance with the methods of treatment herein binds an epitope comprising one, two, three, four, five or more of residues selected from the group consisting of: R13, P14, S15, H23, A25, Q27, I60 and G62 (with reference to SEQ ID NO: 1), and/or has reduced binding to a KIR3DL2 polypeptide having a mutation at a residue selected from the group consisting of: R13, P14, S15, H23, A25, Q27, I60 and G62 (with reference to SEQ ID NO: 1).

The shorthand notation used for mutations herein is: wild type residue: position in polypeptide, with numbering of residues as indicated in SEQ ID NO: 1: mutant residue.

In one aspect, an anti-KIR3DL2 agent binds an epitope comprising residues R13, A25 and/or Q27 of the KIR3DL2 polypeptide, and/or has reduced binding to a KIR3DL2 polypeptide having a mutation at residues R13, A25 and/or Q27 (with reference to SEQ ID NO: 1). For example, an antibody can have reduced binding to a KIR3DL2 polypeptide having the mutations R13W, A25T and/or Q27R. Optionally, the epitope additionally comprises one or more of residues I60 and/or G62 (with reference to SEQ ID NO: 1), and/or the antibodies have reduced binding to a KIR3DL2 polypeptide having a mutation at residues I60 and/or G62 (with reference to SEQ ID NO: 1, e.g. I60N, G62S). Optionally, the epitope additionally or alternatively comprises one or more of residues P14, S15 and/or H23 (with reference to SEQ ID NO: 1), and/or the antibodies have reduced binding to a KIR3DL2 polypeptide having a mutation at residues P14, S15 and/or H23 (with reference to SEQ ID NO: 1, e.g. P14S, S15A, H23S). Optionally, the epitope does not comprise residues R32 and/or G33 (with reference to SEQ ID NO: 1), and/or the antibodies do not have reduced binding to a KIR3DL2 polypeptide having a mutation at residues R32 and/or G33 (with reference to SEQ ID NO: 1, e.g., R32H and/or G33R). Optionally, the epitope does not comprise residues F50 and/or R53 (with reference to SEQ ID NO: 1), and/or the antibodies do not have reduced binding to a KIR3DL2 polypeptide having a mutation at residues F50 and/or R53 (with reference to SEQ ID NO: 1, e.g., F50A, R53S). The antibody may (e.g. antibodies that block the KIR3DL2-HLA B27 and -HLA A3 interactions) or may not (e.g. non-internalizing antibodies) bind to residues Q56 and/or E57, and/or residues F9 and/or S11; thus, in one embodiment, optionally, the epitope does not comprise residues F9, S11, Q56 and/or E57 (with reference to SEQ ID NO: 1), and/or the antibodies do not have reduced binding to a KIR3DL2 polypeptide having a mutation at residues F9, S11, Q56 and/or E57 (with reference to SEQ ID NO: 1, e.g., F9S and S11A, Q56S and E57A); in another embodiment, optionally, the epitope comprises residues F9, S11, Q56 and/or E57 (with reference to SEQ ID NO: 1), and/or the antibodies have reduced binding to a KIR3DL2 polypeptide having a mutation at residues F9, S11, Q56 and/or E57 (with reference to SEQ ID NO: 1, e.g., F9S and S11A, Q56S and E57A). Optionally, the epitope does not comprise residues H29 and/or F34 (with reference to SEQ ID NO: 1), and/or the antibodies do not have reduced binding to a KIR3DL2 polypeptide having a mutation at residues H29 and/or F34 (with reference to SEQ ID NO: 1, e.g., H29S, F34A). Optionally, the epitope does not comprises one or more of residues F9 and/or S11 (with reference to SEQ ID NO: 1), and/or the antibodies do not have reduced binding to a KIR3DL2 polypeptide having a mutation at residues F9 and/or S11 (with reference to SEQ ID NO: 1, e.g., F9S, S11A).

In one aspect, an anti-KIR3DL2 agent binds an epitope comprising residues I60 and/or G62 of the KIR3DL2 polypeptide of SEQ ID NO: 1, and/or has reduced binding to a KIR3DL2 polypeptide having a mutation at residues I60 and/or G62 (with reference to SEQ ID NO: 1). For example, an antibody can have reduced binding to a KIR3DL2 polypeptide having the mutations I60N and/or G62S. Optionally, the epitope additionally or alternatively comprises one or more of residues P14, S15 and/or H23 (with reference to SEQ ID NO: 1), and/or the antibodies have reduced binding to a KIR3DL2 polypeptide having a mutation at residues P14, S15 and/or H23 (with reference to SEQ ID NO: 1, e.g. P14S, S15A, H23S). Optionally, the antibodies do not bind residues R13, A25 and/or Q27 of the KIR3DL2 polypeptide, and/or do not have reduced binding to a KIR3DL2 polypeptide having a mutation at residues R13, A25 and/or Q27 (e.g., a KIR3DL2 polypeptide having the mutations R13W, A25T and/or Q27R).

In one aspect, an anti-KIR3DL2 agent binds an epitope comprising residues P14, S15 and/or H23 of the KIR3DL2 polypeptide of SEQ ID NO: 1, and/or has reduced binding to a KIR3DL2 polypeptide having a mutation at residues P14, S15 and/or H23 (with reference to SEQ ID NO: 1, e.g. P14S, S15A, H23S).

In one aspect, an anti-KIR3DL2 agent displays reduced binding to (1) a KIR3DL2 polypeptide having a mutation at residues I60 and/or G62 (with reference to SEQ ID NO: 1, e.g. I60N, G62S), and (2) a KIR3DL2 polypeptide having a mutation at residues P14, S15 and/or H23 (with reference to SEQ ID NO: 1, e.g. P14S, S15A, H23S).

In one aspect, an anti-KIR3DL2 agent binds an epitope comprising: (a) 1, 2 or 3 of residues R13, A25 and/or Q27 and (b) one or both of residues I60 and/or G62 of the KIR3DL2 polypeptide. In one aspect antibodies have reduced binding to a KIR3DL2 polypeptide having: (a) a mutation at 1, 2 or 3 of residues R13, A25 and/or Q27, and (b) a mutation at one or both of residues I60 and/or G62.

In one aspect, an anti-KIR3DL2 agent binds an epitope comprising residues R78 and/or L82 of the KIR3DL2 polypeptide of SEQ ID NO: 1, and/or has reduced binding to a KIR3DL2 polypeptide having a mutation at residues R78 and/or L82 (with reference to SEQ ID NO: 1). For example, an antibody can have reduced binding to a KIR3DL2 polypeptide having the mutations R78H and L82P. Optionally, the epitope additionally comprises, or excludes, one or more of residues K7, Y30, R31, P79, H80, S81, T83, G84, W85, S86 and/or A87 (with reference to SEQ ID NO: 1), and/or the antibodies have reduced binding to, or does not have reduced binding to, a KIR3DL2 polypeptide having a mutation at residues K7, Y30, R31, P79, H80, S81, T83, G84, W85, S86 and/or A87 (with reference to SEQ ID NO: 1). In one embodiment, the antibodies bind an epitope comprising 1, 2, 3, 4, 5, 6, 7 or more residues in the segment corresponding to residues 1 to 98 of the KIR3DL2 polypeptide (with reference to SEQ ID NO: 1), optionally further wherein the epitope comprises one or more (e.g. 1, 2, 3, 4, 5) of residues K7, Y30, R31, R78, P79, H80, S81, L82, T83, G84, W85, S86 and/or A87.

In one aspect, an anti-KIR3DL2 agent binds an epitope comprising residues W226 of the KIR3DL2 polypeptide of SEQ ID NO: 1, and/or has reduced binding to a KIR3DL2 polypeptide having a mutation at residues W226 (with reference to SEQ ID NO: 1). Optionally, the epitope additionally comprises one or more of residues I231 and/or R246 (with reference to SEQ ID NO: 1), and/or the antibodies have reduced binding to a KIR3DL2 polypeptide having a mutation at residues I231 and/or R246 (with reference to SEQ ID NO: 1, e.g., I231M, R246P). Optionally, the epitope additionally comprises residue E239 (with reference to SEQ ID NO: 1), and/or the antibodies have reduced binding to a KIR3DL2 polypeptide having a mutation at residue E239 (with reference to SEQ ID NO: 1, e.g., E239G).

In one aspect, an anti-KIR3DL2 agent binds an epitope comprising residues I231 and/or R246 of the KIR3DL2 polypeptide of SEQ ID NO: 1, and/or has reduced binding to a KIR3DL2 polypeptide having a mutation at residues I231 and/or R246 (with reference to SEQ ID NO: 1).

In one aspect, an anti-KIR3DL2 agent binds an epitope comprising residue W226 and one or both of residues I231 and/or R246 of the KIR3DL2 polypeptide.

In one aspect, an anti-KIR3DL2 agent has reduced binding to a KIR3DL2 polypeptide having a mutation at residues W226 and a mutation at one or both of residues I231 and/or R246.

Binding of anti-KIR3DL2 antibody to cells transfected with the KIR3DL2 mutants was measured and compared to the ability of anti-KIR3DL2 antibody to bind wild-type KIR3DL2 polypeptide (SEQ ID NO:1) (see International patent publication no. WO2014/044686, the disclosure of which is incorporated herein by reference). A reduction in binding between an anti-KIR3DL2 antibody and a mutant KIR3DL2 polypeptide as used herein means that there is a reduction in binding affinity (e.g., as measured by known methods such FACS testing of cells expressing a particular mutant, or by Biacore testing of binding to mutant polypeptides) and/or a reduction in the total binding capacity of the anti-KIR3DL2 antibody (e.g., as evidenced by a decrease in B max in a plot of anti-KIR3DL2 antibody concentration versus polypeptide concentration). A significant reduction in binding indicates that the mutated residue is directly involved in binding to the anti-KIR3DL2 antibody or is in close proximity to the binding protein when the anti-KIR3DL2 antibody is bound to KIR3DL2. An antibody epitope will may thus include such residue and may include additional residues spatially adjacent to such residue.

In some embodiments, a significant reduction in binding means that the binding affinity and/or capacity between an anti-KIR3DL2 antibody and a mutant KIR3DL2 polypeptide is reduced by greater than 40%, greater than 50%, greater than 55%, greater than 60%, greater than 65%, greater than 70%, greater than 75%, greater than 80%, greater than 85%, greater than 90% or greater than 95% relative to binding between the antibody and a wild type KIR3DL2 polypeptide (e.g., the polypeptide shown in SEQ ID NO:1). In certain embodiments, binding is reduced below detectable limits. In some embodiments, a significant reduction in binding is evidenced when binding of an anti-KIR3DL2 antibody to a mutant KIR3DL2 polypeptide is less than 50% (e.g., less than 45%, 40%, 35%, 30%, 25%, 20%, 15% or 10%) of the binding observed between the anti-KIR3DL2 antibody and a wild-type KIR3DL2 polypeptide (e.g., the extracellular domain shown in SEQ ID NO:1). Such binding measurements can be made using a variety of binding assays known in the art. A specific example of one such assay is described in the Example section.

In some embodiments, anti-KIR3DL2 antibodies exhibit significantly lower binding for a mutant KIR3DL2 polypeptide in which a residue in a wild-type KIR3DL2 polypeptide (e.g., SEQ ID NO:1) is substituted, e.g. the mutants as described in Example 1. In the shorthand notation used here, the format is: Wild type residue: Position in polypeptide: Mutant residue, with the numbering of the residues as indicated in SEQ ID NO: 1.

Optionally, the antibodies have reduced binding to a KIR3DL2 polypeptide having a substitution at residues N99, H100, E130, H131, F132, V178, P179, H180, S181, P182, Y183 and/or residue Q184 of SEQ ID NO: 1.

In some embodiments, an anti-KIR3DL2 antibody binds a wild-type KIR3DL2 polypeptide having a sequence of SEQ ID NO: 1 but has decreased binding to a mutant KIR3DL2 polypeptide having any one or more (e.g., 1, 2, 3 or 4) of the following mutations: P179T and/or S181T (with reference to SEQ ID NO:1). In one embodiment, binding to the mutant KIR3DL2 is significantly reduced compared to binding to the wild-type KIR3DL2.

In some embodiments, anti-KIR3DL2 antibodies exhibit significantly lower binding for a mutant KIR3DL2 polypeptide in which a residue in a segment corresponding to residues 1-98, residues 99-292, or residues 99-192 (or a subsequence thereof) in a wild-type KIR3DL2 polypeptide (e.g., SEQ ID NO:1) is substituted with a different amino acid.

In one aspect, an antibody can compete with monoclonal antibody 10F6, 2B12, 18C6, 9E10, 10G5, 13H1, 5H1, 1E2, 1C3 or 20E9 and recognizes bind to, or have immunospecificity for substantially or essentially the same, or the same, epitope or "epitopic site" on a KIR3DL2 molecule as monoclonal antibody 10F6, 2B12, 18C6, 9E10, 10G5, 13H1, 5H1, 1E2, 1C3 or 20E9. In other embodiments, the monoclonal antibody consists of, or is a derivative or fragment of, antibody 10F6, 2B12, 18C6, 9E10, 10G5, 13H1, 5H1, 1E2, 1C3 or 20E9.

It will be appreciated that, while antibodies may bind to the same epitope as antibody 10F6, 2B12, 18C6, 9E10, 10G5, 13H1, 5H1, 1E2, 1C3 or 20E9, suitable antibodies can recognize and be raised against any part of the KIR3DL2 polypeptide so long as the antibody binds KIR3DL2 and has the desired functionality. For example, any fragment of KIR3DL2, e.g., human KIR3DL2, or any combination of KIR3DL2 fragments, can be used as immunogens to raise antibodies, and the antibodies can recognize epitopes at any location within the KIR3DL2 polypeptide, so long as they can do so on KIR3DL2 expressing NK cells as described herein. In an embodiment, the recognized epitopes are present on the cell surface, i.e. they are accessible to antibodies present outside of the cell. Optionally, the epitope is the epitope specifically recognized by antibody 10F6, 2B12, 18C6, 9E10, 10G5, 13H1, 5H1, 1E2, 1C3 or 20E9. Further, antibodies recognizing distinct epitopes within KIR3DL2 can be used in combination, e.g. to bind to KIR3DL2 polypeptides with maximum efficacy and breadth among different individuals.

The antibodies may be produced by a variety of techniques known in the art. Typically, they are produced by immunization of a non-human animal, optionally a mouse, with an immunogen comprising a KIR3DL2 polypeptide, optionally a human KIR3DL2 polypeptide. The KIR3DL2 polypeptide may comprise the full length sequence of a human KIR3DL2 polypeptide, or a fragment or derivative thereof, typically an immunogenic fragment, i.e., a portion of the polypeptide comprising an epitope exposed on the surface of cells expressing a KIR3DL2 polypeptide, optionally the epitope recognized by the 10F6, 2B12, 18C6, 9E10, 10G5, 13H1, 5H1, 1E2, 1C3 or 20E9 antibody. Such fragments typically contain at least about 7 consecutive amino acids of the mature polypeptide sequence, or at least about 10 consecutive amino acids thereof. Fragments typically are essentially derived from the extra-cellular domain of the receptor. In one embodiment, the immunogen comprises a wild-type human KIR3DL2 polypeptide in a lipid membrane, typically at the surface of a cell. In one embodiment, the immunogen comprises intact cells, particularly intact human cells, optionally treated or lysed. In another embodiment, the polypeptide is a recombinant KIR3DL2 polypeptide.

The step of immunizing a non-human mammal with an antigen may be carried out in any manner well known in the art for stimulating the production of antibodies in a mouse (see, for example, E. Harlow and D. Lane, Antibodies: A Laboratory Manual, Cold Spring Harbor Laboratory Press, Cold Spring Harbor, NY (1988), the entire disclosure of which is herein incorporated by reference). For exemplary monoclonal antibodies, the next step is the isolation of splenocytes from the immunized non-human mammal and the subsequent fusion of those splenocytes with an immortalized cell in order to form an antibody-producing hybridoma. Once isolated and present in single cell suspension, lymphocytes can be fused to an immortal cell line.

Antibodies may also be produced by selection of combinatorial libraries of immunoglobulins, as disclosed for instance in (Ward et al. Nature, 341 (1989) p. 544, the entire disclosure of which is herein incorporated by reference).

The identification of one or more antibodies that bind(s) to KIR3DL2 can be readily determined using any one of a variety of immunological screening assays in which antibody competition can be assessed. Many such assays are routinely practiced and are well known in the art (see, e.g., U.S. Pat. No. 5,660,827, issued Aug. 26, 1997, which is specifically incorporated herein by reference). It will be understood that actually determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control (10F6, 2B12, 18C6, 9E10, 10G5, 13H1, 5H1, 1E2, 1C3 or 20E9, for example) and test antibodies are admixed (or pre-adsorbed) and applied to a sample containing KIR3DL2 polypeptides. Protocols based upon western blotting and the use of BIACORE analysis are suitable for use in such competition studies.

In certain embodiments, one pre-mixes the control antibodies (10F6, 2B12, 18C6, 9E10, 10G5, 13H1, 5H1, 1E2, 1C3 or 20E9, for example) with varying amounts of the test antibodies (e.g., about 1:10 or about 1:100) for a period of time prior to applying to the KIR3DL2 antigen sample. In other embodiments, the control and varying amounts of test antibodies can simply be admixed during exposure to the KIR3DL2 antigen sample. As long as one can distinguish bound from free antibodies (e.g., by using separation or washing techniques to eliminate unbound antibodies) and 10F6, 2B12, 18C6, 9E10, 10G5, 13H1, 5H1, 1E2, 1C3 or 20E9 from the test antibodies (e.g., by using species-specific or isotype-specific secondary antibodies or by specifically labeling 10F6, 2B12, 18C6, 9E10, 10G5, 13H1, 5H1, 1E2, 1C3 or 20E9 with a detectable label) one can determine if the test antibodies reduce the binding of 10F6, 2B12, 18C6, 9E10, 10G5, 13H1, 5H1, 1E2, 1C3 or 20E9 to the antigens. The binding of the (labeled) control antibodies in the absence of a completely irrelevant antibody can serve as the control high value. The control low value can be obtained by incubating the labeled (10F6, 2B12, 18C6, 9E10, 10G5, 13H1, 5H1, 1E2, 1C3 or 20E9) antibodies with unlabeled antibodies of exactly the same type (10F6, 2B12, 18C6, 9E10, 10G5, 13H1, 5H1, 1E2, 1C3 or 20E9), where competition would occur and reduce binding of the labeled antibodies. In a test assay, a significant reduction in labeled antibody reactivity in the presence of a test antibody is indicative of a test antibody that may recognize substantially the same epitope. A test antibody may for example reduce the binding of 10F6, 2B12, 18C6, 9E10, 10G5, 13H1, 5H1, 1E2, 1C3 or 20E9 to KIR3DL2 antigens by at least about 50%, such as at least about 60%, or more preferably at least about 80% or 90% (e.g., about 65-100%), at any ratio of 10F6, 2B12, 18C6, 9E10, 10G5, 13H1, 5H1, 1E2, 1C3 or 20E9: test antibody between about 1:10 and about 1:100. For example such test antibody can reduce the binding of 10F6, 2B12, 18C6, 9E10, 10G5, 13H1, 5H1, 1E2, 1C3 or 20E9 to the KIR3DL2 antigen by at least about 90% (e.g., about 95%).

Competition can also be assessed by, for example, a flow cytometry test. In such a test, cells bearing a given KIR3DL2 polypeptide can be incubated first with 10F6, 2B12, 18C6, 9E10, 10G5, 13H1, 5H1, 1E2, 1C3 or 20E9, for example, and then with the test antibody labeled with a fluorochrome or biotin. The antibody is said to compete with 10F6, 2B12, 18C6, 9E10, 10G5, 13H1, 5H1, 1E2, 1C3 or 20E9 if the binding obtained upon preincubation with a saturating amount of 10F6, 2B12, 18C6, 9E10, 10G5, 13H1, 5H1, 1E2, 1C3 or 20E9 is about 80%, about 50%, about 40% or less (e.g., about 30%, 20% or 10%) of the binding (as measured by mean of fluorescence) obtained by the antibody without preincubation with 10F6, 2B12, 18C6, 9E10, 10G5, 13H1, 5H1, 1E2, 1C3 or 20E9. Alternatively, an antibody is said to compete with 10F6, 2B12, 18C6, 9E10, 10G5, 13H1, 5H1, 1E2, 1C3 or 20E9 if the binding obtained with a labeled 10F6, 2B12, 18C6, 9E10, 10G5, 13H1, 5H1, 1E2, 1C3 or 20E9 antibody (by a fluorochrome or biotin) on cells preincubated with a saturating amount of test antibody is about 80%, about 50%, about 40%, or less (e.g., about 30%, 20% or 10%) of the binding obtained without preincubation with the test antibody.

A simple competition assay in which a test antibody is pre-adsorbed and applied at saturating concentration to a surface onto which a KIR3DL2 antigen is immobilized may also be employed. The surface in the simple competition assay is for example a BIACORE chip (or other media suitable for surface plasmon resonance analysis). The control antibody (e.g., 10F6, 2B12, 18C6, 9E10, 10G5, 13H1, 5H1, 1E2, 1C3 or 20E9) is then brought into contact with the surface at a KIR3DL2-saturating concentration and the KIR3DL2 and surface binding of the control antibody is measured. This binding of the control antibody is compared with the binding of the control antibody to the KIR3DL2-containing surface in the absence of test antibody. In a test assay, a significant reduction in binding of the KIR3DL2-containing surface by the control antibody in the presence of a test antibody indicates that the test antibody competes and may recognize substantially the same epitope as the control antibody. Any test antibody that reduces the binding of control (such as 10F6, 2B12, 18C6, 9E10, 10G5, 13H1, 5H1, 1E2, 1C3 or 20E9) antibody to a KIR3DL2 antigen by at least about 30% or more, or about 40%, can be selected. For example, such a test antibody will reduce the binding of the control antibody (e.g., 10F6, 2B12, 18C6, 9E10, 10G5, 13H1, 5H1, 1E2, 1C3 or 20E9) to the KIR3DL2 antigen by at least about 50% (e.g., at least about 60%, at least about 70%, or more). It will be appreciated that the order of control and test antibodies can be reversed: that is, the control antibody can be first bound to the surface and the test antibody is brought into contact with the surface thereafter in a competition assay. For example, the antibody having higher affinity for the KIR3DL2 antigen is bound to the surface first, as it will be expected that the decrease in binding seen for the second antibody (assuming the antibodies are cross-reacting) will be of greater magnitude. Further examples of such assays are provided in, e.g., Saunal (1995) J. Immunol. Methods 183: 33-41, the disclosure of which is incorporated herein by reference.

Determination of whether an antibody binds within an epitope region can be carried out in ways known to the person skilled in the art. As one example of such mapping/characterization methods, an epitope region for an anti-KIR3DL2 antibody may be determined by epitope "foot-printing" using chemical modification of the exposed amines/carboxyls in the KIR3DL2 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e.g., Ehring H, Analytical Biochemistry, Vol. 267 (2) pp. 252-259 (1999) Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectrum of the complex compared to the spectrum of the free antigen, and the amino acids involved in the binding can be identified that way. See, e.g., Ernst Schering Res Found Workshop. 2004; (44): 149-67; Huang et Journal of Molecular Biology, Vol. 281 (1) pp. 61-67 (1998); and Saito and Patterson, Methods. 1996 June; 9 (3): 516-24.

Epitope mapping/characterization also can be performed using mass spectrometry methods. See, e.g., Downward, J Mass Spectrom. 2000 April; 35 (4): 493-503 and Kiselar and Downward, Anal Chem. 1999 May 1; 71 (9): 1792-801. Protease digestion techniques also can be useful in the context of epitope mapping and identification. Antigenic determinant-relevant regions/sequences can be determined by protease digestion, e.g. by using trypsin in a ratio of about 1:50 to KIR3DL2 or o/n digestion at and pH 7-8, followed by mass spectrometry (MS) analysis for peptide identification. The peptides protected from trypsin cleavage by the anti-KIR3DL2 binder can subsequently be identified by comparison of samples subjected to trypsin digestion and samples incubated with antibody and then subjected to digestion by e.g. trypsin (thereby revealing a footprint for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the KIR3DL2 polypeptide that is not surface exposed and, accordingly, most likely not relevant in terms of immunogenicity/antigenicity. See, e.g., Manca, Ann 1st Super Sanita. 1991; 27: 15-9 for a discussion of similar techniques.

Site-directed mutagenesis is another technique useful for elucidation of a binding epitope. For example, in "alanine-scanning", each residue within a protein segment is replaced with an alanine residue, and the consequences for binding affinity measured. If the mutation leads to a significant reduction in binding affinity, it is most likely involved in binding. Monoclonal antibodies specific for structural epitopes (i.e., antibodies which do not bind the unfolded protein) can be used to verify that the alanine-replacement does not influence overall fold of the protein. See, e.g., Clackson and Wells, Science 1995; 267:383-386; and Wells, Proc Natl Acad Sci USA 1996; 93:1-6.

Electron microscopy can also be used for epitope "footprinting". For example, Wang et al., Nature 1992; 355:275-278 used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance (SPR, BIACORE) and reflectometric interference spectroscopy (RifS). See, e.g., Fägerstam et al., Journal Of Molecular Recognition 1990; 3:208-14; Nice et al., J. Chromatogr. 1993; 646:159-168; Leipert et al., Angew. Chem. Int. Ed. 1998; 37:3308-3311; Kröger et al., Biosensors and Bioelectronics 2002; 17:937-944.

It should also be noted that an antibody binding the same or substantially the same epitope as an antibody can be identified in one or more of the exemplary competition assays described herein.

Once antibodies are identified that are capable of binding KIR3DL2 and/or having other desired properties, they will also typically be assessed, using standard methods including those described herein, for their ability to bind to other polypeptides, including unrelated polypeptides. Ideally, the antibodies only bind with substantial affinity to KIR3DL2, e.g., human KIR3DL2, and do not bind at a significant level to unrelated polypeptides. However, it will be appreciated that, as long as the affinity for KIR3DL2 is substantially greater (e.g., 5×, 10×, 50×, 100×, 500×, 1000×, 10,000×, or more) than it is for other, unrelated polypeptides), then the antibodies are suitable for use in the present methods.

In one aspect of any of the embodiments, the antibodies prepared according to the present methods are monoclonal antibodies. In another aspect, the non-human animal used iesto produce antibodies is a mammal, such as a rodent, bovine, porcine, fowl, horse, rabbit, goat, or sheep.

According to an alternate embodiment, the DNA encoding an antibody that binds an epitope present on KIR3DL2 polypeptides is isolated from the hybridoma and placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

DNA encoding a monoclonal antibody, e.g., antibody 10F6, 2B12, 18C6, 9E10, 10G5, 13H1, 5H1, 1E2, 1C3 or 20E9, can be readily isolated and sequenced using conventional procedures (e.g., by using oligonucleotide probes that are capable of binding specifically to genes encoding the heavy and light chains of murine antibodies). Once isolated, the DNA can be placed into expression vectors, which are then transfected into host cells such as $E.\ coli$ cells, simian COS cells, Chinese hamster ovary (CHO) cells, or myeloma cells that do not otherwise produce immunoglobulin protein, to obtain the synthesis of monoclonal antibodies in the recombinant host cells. As described elsewhere in the present specification, such DNA sequences can be modified for any of a large number of purposes, e.g., for humanizing antibodies, producing fragments or derivatives, or for modifying the sequence of the antibody, e.g., in the antigen binding site in order to optimize the binding specificity of the antibody.

Recombinant expression in bacteria of DNA encoding the antibody is well known in the art (see, for example, Skerra et al., Curr. Opinion in Immunol., 5, pp. 256 (1993); and Pluckthun, Immunol. 130, p. 151 (1992).

In one embodiment, an antibody is capable of mediating the depletion of pathogenic KIR3DL2-expressing cells (e.g. tumor cells) via ADCC (and optionally further via ADCP). Once an antigen-binding compound is obtained it may be assessed for its ability to induce ADCC towards, inhibit the activity and/or proliferation of and/or cause the elimination of KIR3DL2-expressing target cells. Assessing the antigen-binding compound's ability to induce ADCC or generally lead to the elimination or inhibition of activity of KIR3DL2-expressing target cells, can be carried out at any suitable stage of the method. This assessment can be useful at one or more of the various steps involved in the identification, production and/or development of an antibody (or other compound) destined for therapeutic use. For example, activity may be assessed in the context of a screening method to identify candidate antigen-binding compounds, or in methods where an antigen-binding compound is selected and made human suitable (e.g. made chimeric or humanized in the case of an antibody), where a cell expressing the antigen-binding compound (e.g. a host cell expressing a recombinant antigen-binding compound) has been obtained and is assessed for its ability to produce functional antibodies (or other compounds), and/or where a quantity of antigen-binding compound has been produced and is to be assessed for activity (e.g. to test batches or lots of product). Generally the antigen-binding compound will be known to specifically bind to a KIR3DL2 polypeptide. The step may involve testing a plurality (e.g., a very large number using high throughput screening methods or a smaller number) of antigen-binding compounds.

Testing ADCC can be carried out can be determined by various assays including those known in the art and those described in the experimental examples herein. Testing ADCC typically involves assessing cell-mediated cytotoxicity in which a KIR3DL2-expressing target cell (e.g. a celiac disease cell or other KIR3DL2-expressing cell) with bound anti-KIR3DL2 antibody is recognized by an effector cell bearing Fc receptors, without the involvement of complement. A cell which does not express a KIR3DL2 antigen can optionally be used as a control. Activation of NK cell cytotoxicity is assessed by measuring an increase in cytokine production (e.g. IFN-γ production) or cytotoxicity markers (e.g. CD107 mobilization). In one embodiment, the antibody will induce an increase in cytokine production, expression of cytotoxicity markers, or target cell lysis of at least 20%, 50%, 80%, 100%, 200% or 500% in the presence of target cells, compared to a control antibody (e.g. an antibody not binding to KIR3DL2, a KIR3DL2 antibody having murine constant regions). In another example, lysis of target cells is detected, e.g. in a chromium release assay, for example the antibody will induce lysis of at least 10%, 20%, 30%, 40% or 50% of target cells.

In one embodiment, an anti-KIR3DL2 antibody does not substantially increase or induce intracellular internalization of KIR3DL2 expressed at the surface of a cell. As used herein, an anti-KIR3DL2 antibody that is not "internalized" or that does not "internalize" is one that is not substantially taken up by (i.e., enters) the cell upon binding to KIR3DL2 on a mammalian cell (i.e. cell surface KIR3DL2).

In one embodiment, an anti-KIR3DL2 antibody is capable of causing an increase of cell surface KIR3DL2 polypeptide available for binding by an anti-KIR3DL2 antibody, notably on malignant cells. The antibodies may, in one embodiment, increase the level of expression of KIR3DL2 polypeptides on the cell surface (e.g. of malignant cells). The antibodies may, in one embodiment, increase the amount or number of KIR3DL2 polypeptides on the cell surface available for binding by an anti-KIR3DL antibody. The antibodies may, in one embodiment, stabilize and/or cause accumulation of KIR3DL2 polypeptides present on the cell surface, e.g., they may decrease receptor cycling or internalization of KIR3DL2 polypeptides. Antibodies that increase cell surface KIR3DL2, e.g. on pathogenic CD4+ T cells, have increased potency because they permit a greater number of antibodies to be bound to a KIR3DL2-expressing cell (e.g. target cell, malignant cell). In one embodiment, provided is an isolated monoclonal antibody that binds a KIR3DL2 polypeptide on the surface of a KIR3DL2-expressing cell, wherein the antibody causes an increase of the amount or numbers of KIR3DL2 polypeptides detectable at the cell surface after being in contact with cells (in vivo or in vitro) for at least 1 hour, 3 hours, 6 hours, 12 hours or 24 hours. The increase can be in comparison to a control antibody, e.g. an isotype control, or another antibody that binds KIR3DL2 (e.g. an antibody that has a different heavy and/or light chain variable region amino acid sequence).

Whether an anti-KIR3DL2 antibody internalizes upon binding KIR3DL2 on a mammalian cell, or whether a KIR3DL2 polypeptide undergoes intracellular internalization (e.g. upon being bound by an antibody) can be determined by various assays including those described in the experimental examples PCT/EP2013/069302 and PCT/EP2013/069293, both filed 17 Sep. 2013. For examples cells can be incubated in tissue culture dishes in the presence or absence of the relevant antibodies added to the culture media and processed for microscopic analysis at desired time points. The presence of an internalized, labelled antibody in the cells can be directly visualized by microscopy or by autoradiography if radiolabelled antibody is used. Optionally, in microscopy, co-localization with a known polypeptide or other cellular component can be assessed; for example co-localization with endosomal/lysosomal marker LAMP-1 (CD107a) can provide information about the subcellular localization of the internalized antibody.

Testing whether an antibody is capable of increasing the number of KIR3DL2 polypeptides at the surface of a cell can be carried out by incubating the test antibody with a KIR3DL2-expressing cell (e.g. a T cell lymphoma) and detecting KIR3DL2 polypeptides at the surface of the cell after the incubation period. KIR3DL2 polypeptides can be carried out using a suitable affinity regent, e.g. one or more antibodies. Exemplary assays are shown in PCT/EP2013/069302 and PCT/EP2013/069293. For example, an antibody may induce an increase of at least 20%, 50%, 75% or 100% of the number of KIR3DL2 polypeptides detectable at the surface of cells after incubation (e.g. for at least 1, 3, 6, 12, 24 or 48 hours) in the presence of test antibody, compared to a control antibody (e.g. an antibody not binding to KIR3DL2, a different anti-KIR3DL2 antibody). Optionally, the number of KIR3DL2 polypeptides detectable at the surface of cells after incubation is the number detectable using the test antibody. Optionally, the number of KIR3DL2 polypeptides detectable at the surface of cells after incubation is the number detectable using a second anti-KIR3DL2 antibody that does not compete with the test antibody for binding to KIR3DL2.

In one embodiment, an anti-KIR3DL2 antibody can be tested for its ability to detectably reduce (or eliminate) binding between the KIR3DL2 and an HLA natural ligand of KIR3DL2. Exemplary assays are shown in PCT/EP2013/069302 and PCT/EP2013/069293. In one embodiment, provided is an antibody that binds a KIR3DL2 polypeptide, wherein said antibody detectably reduces (or eliminates) binding between the KIR3DL2 and a first HLA natural ligand of KIR3DL2 but does not detectably reduce (or eliminate) binding between the KIR3DL2 and a second HLA natural ligand of KIR3DL2.

In one embodiment, the antibody optionally detectably reduces binding between the KIR3DL2 and an HLA class 1-ligand of KIR3DL2 (e.g. HLA-B27). In one embodiment, the antibody optionally detectably reduces binding between the KIR3DL2 and HLA-B27 but does not detectably reduce binding between KIR3DL2 and HLA-A3.

When an agent that binds a KIR3DL2 polypeptide has been identified, it can be tested to determine the concentration that provide a specified "NK % lytic capacity" by testing the ability of NK cells to lyse tumor cells (e.g. HUT78 cells) in an in vitro cytotoxicity assay, as measured in a $^{51}$Cr release assay, by the percentage of maximal tumor cell lysis obtained (=Tumor cell lysis/Max tumor cell lysis at saturation×100). Examples of suitable assays employing PBMC and HUT78 cells as effector and target cells are described in the Examples herein. The anti-KIR3DL2 agent can be tested to determine the $EC_{10}$, the $EC_{60}$, $EC_{80}$, $EC_{90}$, or $EC_{100}$ of its maximum response or effect with respect to such NK lytic capacity. Typically, the NK cells are NK cells from a healthy human donor, e.g. within PBMC. A suitable number of experiments using samples from different donors can be carried out, e.g. 10, 20 or more different donor samples.

In certain embodiments, the DNA of a hybridoma producing an antibody can be modified prior to insertion into an expression vector, for example, by substituting the coding sequence for human heavy- and light-chain constant domains in place of the homologous non-human sequences (e.g., Morrison et al., PNAS pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody.

Thus, according to another embodiment, the antibody is humanized. "Humanized" forms of antibodies according are specific chimeric immunoglobulins, immunoglobulin chains or fragments thereof (such as Fv, Fab, Fab', F (ab') 2, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 2, pp. 593 (1992); Verhoeyen et Science, 239, pp. 1534; and U.S. Pat. No. 4,816,567, the entire disclosures of which are herein incorporated by reference.) Methods for humanizing the antibodies are well known in the art.

The choice of human variable domains, both light and heavy, to be used in making the humanized antibodies is very important to reduce antigenicity. According to the so-called "best-fit" method, the sequence of the variable domain of an antibody is screened against the entire library of known human variable-domain sequences. The human sequence which is closest to that of the mouse is then accepted as the human framework (FR) for the humanized antibody (Sims et al., J. Immunol. 151, pp. 2296 (1993); Chothia and Lesk, J. Mol. 196, 1987, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et al., J. Immunol., 151, p. 2623 (1993)).

It is further important that antibodies be humanized with retention of high affinity for KIR3DL2 receptors and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen (5), is achieved. In general, the CDR residues are directly and most substantially involved in influencing antigen binding.

Another method of making "humanized" monoclonal antibodies is to use a XenoMouse (Abgenix, Fremont, CA) as the mouse used for immunization. A XenoMouse is a murine host that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference.

Human antibodies may also be produced according to various other techniques, such as by using, for immunization, other transgenic animals that have been engineered to express a human antibody repertoire (Jakobovitz et al., Nature 362 (1993) 255), or by selection of antibody repertoires using phage display methods. Such techniques are known to the skilled person and can be implemented starting from monoclonal antibodies as disclosed in the present application.

In view of the ability of the anti-KIR3DL2 antibodies to induce ADCC, the antibodies can be made with modifications that increase their ability to bind Fc receptors which can affect effector functions such as antibody-dependent cytotoxicity, mast cell degranulation, and phagocytosis, as well as immunomodulatory signals such as regulation of lymphocyte proliferation and antibody secretion. Typical modifications include modified human IgG1 constant regions comprising at least one amino acid modification (e.g. substitution, deletions, insertions), and/or altered types of glycosylation, e.g., hypofucosylation. Such modifications can affect interaction with Fc receptors: FcγRI (CD64), FcγRII (CD32), and FcγRIII (CD 16). FcγRI (CD64), FcγRIIA (CD32A) and FcγRIII (CD 16) are activating (i.e., immune system enhancing) receptors while FcγRIIB (CD32B) is an inhibiting (i.e., immune system dampening) receptor. A modification may, for example, increase binding of the Fc domain to FcγRIIIa on effector (e.g. NK) cells.

Anti-KIR3DL2 antibodies may comprise an Fc domain (or portion thereof) of human IgG1 or IgG3 isotype, optionally modified. Residues 230-341 (Kabat EU) are the Fc CH2 region. Residues 342-447 (Kabat EU) are the Fc CH3 region. Anti-KIR3DL2 antibodies may comprise a variant Fc region having one or more amino acid modifications (e.g., substitutions, deletions, insertions) in one or more portions, which modifications increase the affinity and avidity of the variant Fc region for an FcγR (including activating and inhibitory FcγRs). In some embodiments, said one or more amino acid modifications increase the affinity of the variant Fc region for FcγRIIIA and/or FcγRIIA. In another embodiment, the variant Fc region further specifically binds FcγRIIB with a lower affinity than does the Fc region of the comparable parent antibody (i.e., an antibody having the same amino acid sequence as the antibody except for the one or more amino acid modifications in the Fc region). For example, the one or both of the histidine residues at amino acid positions 310 and 435 may be substituted, for example by lysine, alanine, glycine, valine, leucine, isoleucine, proline, methionine, tryptophan, phenylalanine, serine or threonine (see, e.g. PCT publication no. WO 2007/080277); such substituted constant regions provide decreased binding to the inhibitory FcγRIIB without decreasing binding to the activatory FcγRIIIA. In some embodiments, such modifications increase the affinity of the variant Fc region for FcγRIIIA and/or FcγRIIA and also enhance the affinity of the variant Fc region for FcγyRIIB relative to the parent antibody. In other embodiments, said one or more amino acid modifications increase the affinity of the variant Fc region for FcγRIIIA and/or FcγRIIA but do not alter the affinity of the variant Fc regions for FcγRIIB relative to the Fc region of the parent antibody. In another embodiment, said one or more amino acid modifications enhance the affinity of the variant Fc region for FcγRIIIA and FcγRIIA but reduce the affinity for FcγRIIB relative to the parent antibody. Increased affinity and/or avidity results in detectable binding to the FcγR or FcγR-related activity in cells that express low levels of the FcγR when binding activity of the parent molecule (without the modified Fc region) cannot be detected in the cells.

The affinities and binding properties of the molecules for an FcγR can be determined using in vitro assays (biochemical or immunological based assays) known in the art for determining antibody-antigen or Fc-FcγR interactions, i.e., specific binding of an antigen to an antibody or specific binding of an Fc region to an FcγR, respectively, including but not limited to ELISA assay, surface plasmon resonance assay, immunoprecipitation assays.

Specific mutations (in IgG1 Fc domains) which affect (enhance) FcγRIIIa or FcRn binding are also set forth below.

| Isotype | Species | Modification | Effector Function | Effect of Modification |
|---|---|---|---|---|
| IgG1 | Human | T250Q/M428L | Increased binding to FcRn | Increased half-life |
| IgG1 | Human | 1M252Y/S254T/ T256E + H433K/ N434F | Increased binding to FcRn | Increased half-life |
| IgG1 | Human | E333A | Increased binding to FcγRIIIa | Increased ADCC and CDC |
| IgG1 | Human | S239D/I332E or S239D/A330L/ I332E | Increased binding to FcγRIIIa | Increased ADCC |

-continued

| Isotype | Species | Modification | Effector Function | Effect of Modification |
|---|---|---|---|---|
| IgG1 | Human | P257I/Q311 | Increased binding to FcRn | Unchanged half-life |
| IgG1 | Human | S239D/I332E/ G236A | Increased FcγRIIa/ FcγRIIb ratio | Increased macrophage phagocytosis |

In some embodiments, the molecules comprising a variant Fc region comprise at least one amino acid modification (for example, possessing 1, 2, 3, 4, 5, 6, 7, 8, 9, or more amino acid modifications) in the CH3 domain of the Fc region. In other embodiments, the molecules comprising a variant Fc region comprise at least one amino acid modification (for example, possessing 1, 2, 3, 4, 5, 6, 7, 8, 9, or more amino acid modifications) in the CH2 domain of the Fc region, which is defined as extending from amino acids 231-341. In some embodiments, the molecules comprise at least two amino acid modifications (for example, possessing 2, 3, 4, 5, 6, 7, 8, 9, or more amino acid modifications), wherein at least one such modification is in the CH3 region and at least one such modification is in the CH2 region. Amino acid modifications may be made for example in the hinge region. In a particular embodiment, the invention encompasses amino acid modification in the CH1 domain of the Fc region, which is defined as extending from amino acids 216-230.

Any combination of Fc modifications can be made, for example any combination of different modifications disclosed in U.S. Pat. Nos. 7,632,497; 7,521,542; 7,425,619; 7,416,727; 7,371,826; 7,355,008; 7,335,742; 7,332,581; 7,183,387; 7,122,637; 6,821,505 and 6,737,056; in PCT Publications Nos. WO2011/109400; WO 2008/105886; WO 2008/002933; WO 2007/021841; WO 2007/106707; WO 06/088494; WO 05/115452; WO 05/110474; WO 04/1032269; WO 00/42072; WO 06/088494; WO 07/024249; WO 05/047327; WO 04/099249 and WO 04/063351; and in Presta, L. G. et al. (2002) Biochem. Soc. Trans. 30(4):487-490; Shields, R. L. et al. (2002) J. Biol. Chem. 26; 277(30):26733-26740 and Shields, R. L. et al. (2001) J. Biol. Chem. 276(9):6591-6604).

Anti-KIR3DL2 antibodies may comprise a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule has an enhanced effector function relative to a molecule comprising a wild-type Fc region, optionally wherein the variant Fc region comprises a substitution at any one or more of positions 221, 239, 243, 247, 255, 256, 258, 267, 268, 269, 270, 272, 276, 278, 280, 283, 285, 286, 289, 290, 292, 293, 294, 295, 296, 298, 300, 301, 303, 305, 307, 308, 309, 310, 311, 312, 316, 320, 322, 326, 329, 330, 332, 331, 332, 333, 334, 335, 337, 338, 339, 340, 359, 360, 370, 373, 376, 378, 392, 396, 399, 402, 404, 416, 419, 421, 430, 434, 435, 437, 438 and/or 439.

Anti-KIR3DL2 antibodies may comprise a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule has an enhanced effector function relative to a molecule comprising a wild-type Fc region, optionally wherein the variant Fc region comprises a substitution at any one or more of positions 329, 298, 330, 332, 333 and/or 334 (e.g. S239D, S298A, A330L, I332E, E333A and/or K334A substitutions).

In one embodiment, antibodies having variant or wild-type Fc regions may have altered glycosylation patterns that increase Fc receptor binding ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. See, for example, Shields, R. L. et al. (2002) J. Biol. Chem. 277:26733-26740; Umana et al. (1999) Nat. Biotech. 17:176-1, as well as, European Patent No: EP 1,176,195; PCT Publications WO 06/133148; WO 03/035835; WO 99/54342, each of which is incorporated herein by reference in its entirety.

Generally, such antibodies with altered glycosylation are "glyco-optimized" such that the antibody has a particular N-glycan structure that produces certain desirable properties, including but not limited to, enhanced ADCC and effector cell receptor binding activity when compared to non-modified antibodies or antibodies having a naturally occurring constant region and produced by murine myeloma NSO and Chinese Hamster Ovary (CHO) cells (Chu and Robinson, Current Opinion Biotechnol. 2001, 12: 180-7), HEK293T-expressed antibodies as produced herein in the Examples section, or other mammalian host cell lines commonly used to produce recombinant therapeutic antibodies.

Monoclonal antibodies produced in mammalian host cells contain an N-linked glycosylation site at Asn297 of each heavy chain. Glycans on antibodies are typically complex biatennary structures with very low or no bisecting N-acetyl-glucosamine (bisecting GlcNAc) and high levels of core fucosylation. Glycan temini contain very low or no terminal sialic acid and variable amounts of galactose. For a review of effects of glycosylation on antibody function, see, e.g., Wright & Morrison, Trend Biotechnol. 15:26-31 (1997). Considerable work shows that changes to the sugar composition of the antibody glycan structure can alter Fc effector functions. The important carbohydrate structures contributing to antibody activity are believed to be the fucose residues attached via alpha-1,6 linkage to the innermost N-acetylglucosamine (GlacNAc) residues of the Fc region N-linked oligosaccharides (Shields et al., 2002).

FcγR binding requires the presence of oligosaccharides covalently attached at the conserved Asn297 in the Fc region of human IgGI, IgG2 or IgG3 type. Non-fucosylated oligosaccharides structures have recently been associated with dramatically increased in vitro ADCC activity. "Asn 297" means amino acid asparagine located at about position 297 in the Fc region; based on minor sequence variations of antibodies, Asn297 can also be located some amino acids (usually not more than +3 amino acids) upstream or downstream.

Historically, antibodies produced in CHO cells contain about 2 to 6% in the population that are nonfucosylated. YB2/0 (rat myeloma) and Lecl3 cell line (a lectin mutant of CHO line which has a deficient GDP-mannose 4,6-dehydratase leading to the deficiency of GDP-fucose or GDP sugar intermediates that are the substrate of alpha6-fucosyltransferase have been reported to produce antibodies with 78 to 98% non-fucosylated species. In other examples, RNA interference (RNAi) or knock-out techniques can be employed to engineer cells to either decrease the FUT8 mRNA transcript levels or knock out gene expression entirely, and such antibodies have been reported to contain up to 70% non-fucosylated glycan.

An antibody that binds to KIR3DL2 may be glycosylated with a sugar chain at Asn297. In one embodiment, an antibody will comprise a constant region comprising at least one amino acid alteration in the Fc region that improves antibody binding to FcγRIIIa and/or ADCC.

In one aspect, the antibodies are hypofucosylated in their constant region. Such antibodies may comprise an amino acid alteration or may not comprise an amino acid alteration but be produced or treated under conditions so as to yield such hypofucosylation. In one aspect, an antibody composition comprises a chimeric, human or humanized antibody described herein, wherein at least 20, 30, 40, 50, 60, 75, 85, 90, 95% or substantially all of the antibody species in the composition have a constant region comprising a core carbohydrate structure (e.g. complex, hybrid and high mannose structures) which lacks fucose. In one embodiment, provided is an antibody composition which is free of antibodies comprising a core carbohydrate structure having fucose. The core carbohydrate will preferably be a sugar chain at Asn297.

In one embodiment, an antibody composition, e.g. a composition comprising antibodies which bind to KIR3DL2, are glycosylated with a sugar chain at Asn297, wherein the antibodies are partially fucosylated. Partially fucosylated antibodies are characterized in that the proportion of anti-KIR3DL2 antibodies in the composition that lack fucose within the sugar chain at Asn297 is between 20% and 90%, between 20% and 80%, between 20% and 50%, 55%, 60%, 70% or 75%, between 35% and 50%, 55%, 60%, 70% or 75%, or between 45% and 50%, 55%, 60%, 70% or 75%. Optionally the antibody is of human IgGI or IgG3 type.

The sugar chain show can further show any characteristics (e.g. presence and proportion of complex, hybrid and high mannose structures), including the characteristics of N-linked glycans attached to Asn297 of an antibody from a human cell, or of an antibody recombinantly expressed in a rodent cell, murine cell (e.g. CHO cell) or in an avian cell.

In one embodiment, the antibody is expressed in a cell that is lacking in a fucosyltransferase enzyme such that the cell line produces proteins lacking fucose in their core carbohydrates. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their core carbohydrates. These cell lines were created by the targeted disruption of the FUT8 gene in CHO/DG44 cells using two replacement vectors (see U.S. Patent Publication No. 20040110704 by Yamane et al.; and Yamane-Ohnuki et al. (2004) Biotechnol Bioeng 87:614-22, the disclosures of which are incorporated herein by reference). Other examples have included use of antisense suppression, double-stranded RNA (dsRNA) interference, hairpin RNA (hpRNA) interference or intron-containing hairpin RNA (ihpRNA) interference to functionally disrupt the FUT8 gene. In one embodiment, the antibody is expressed in a cell line with a functionally disrupted FUT8 gene, which encodes a fucosyl transferase, such that antibodies expressed in such a cell line exhibit hypofucosylation by reducing or eliminating the alpha 1,6 bond-related enzyme.

In one embodiment, the antibody is expressed in cell lines engineered to express glycoprotem-modifying glycosyl transferases (e.g., beta(I,4)-N-acetylglucosaminyl-transferase III (GnTHI)) such that antibodies expressed in the engineered cell lines exhibit increased bisecting GlcNac structures which results in increased ADCC activity of the antibodies (PCT Publication WO 99/54342 by Umana et al.; and Umana et al. (1999) Nat. Biotech. 17:176-180, the disclosures of which are incorporated herein by reference).

In another embodiment, the antibody is expressed and the fucosyl residue(s) is cleaved using a fucosidase enzyme. For example, the fucosidase alpha-L-fucosidase removes fucosyl residues from antibodies (Tarentino, et al. (1975) Biochem. 14:5516-5523). In other examples, a cell line producing an antibody can be treated with a glycosylation inhibitor; Zhou et al. Biotech. and Bioengin. 99: 652-665 (2008) described treatment of CHO cells with the alpha-mannosidase I inhibitor, kifunensine, resulting in the production of antibodies with non-fucosylated oligomannose-type N-glucans.

In one embodiment, the antibody is expressed in a cell line which naturally has a low enzyme activity for adding fucosyl to the N-acetylglucosamine that binds to the Fc region of the antibody or does not have the enzyme activity, for example the rat myeloma cell line YB2/0 (ATCC CRL 1662). Other example of cell lines include a variant CHO cell line, Led 3 cells, with reduced ability to attach fucosyl to Asn(297)-linked carbohydrates, also resulting in hypofucosylation of antibodies expressed in that host cell (WO 03/035835 (Presta et al); and Shields, R X. et al. (2002) J. Biol. Chem. 277:26733-26740, the disclosures of which are incorporated herein by reference). In another embodiment, the antibody is expressed in an avian cell, e.g., a EBx® cell (Vivalis, France) which naturally yields antibodies with low fucose content e.g. WO2008/142124. Hypofucosylated glycans can also be produced in cell lines of plant origin, e.g. WO 07/084926A2 (Biolex Inc.), WO 08/006554 (Greenovation Biotech GMBH), the disclosures of which are incorporated herein by reference.

Antibody Formulations

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. This method comprises the step of contacting said composition with said patient. Such method will be useful for both prophylaxis and therapeutic purposes.

For use in administration to a patient, the composition will be formulated for administration to the patient. The compositions may be administered parenterally, in particular by intravenous injection or infusion techniques.

Sterile injectable forms of the compositions may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Several monoclonal antibodies have been shown to be efficient in clinical situations, such as Rituxan™ (rituximab), Herceptin™ (Trastuzumab) or Xolair™ (Omalizumab), and similar administration regimens (i.e., formulations and/or doses and/or administration protocols) may be used with the antibodies. For example, an antibody present in a pharmaceutical composition can be supplied at a concentration of 10 mg/mL in either 100 mg (10 mL) or 500 mg (50 mL) single-use vials.

Further aspects and advantages will be disclosed in the following experimental section, which should be regarded as illustrative and not limiting the scope of this application.

EXAMPLES

Example 1—Generation of KIR3DL2-Selective Antibodies

Immunization and Screening

Antibodies which bind KIR3DL2 but not closely related KIR3DL1 were generated by immunizing mice with recombinant KIR3DL2-Fc fusion protein, described in US patent publication number US-2015-0232556-A1. Supernatant (SN) of the growing hybridomas were tested by flow cytometry on Sezary Syndrome cell lines (HUT78, COU-L) and HEK-293T/KIR3DL2 Domain 0-eGFP. Potentially interesting hybridomas selected from the initial screening were cloned by limiting dilution techniques in 96-wells plates. The secondary screen involved selection of hybridomas of interest by testing supernatants of the subclones by flow cytometry on HUT78, COU-L, HEK-293T/KIR3DL1 Domain 0-eGFP and HEK-293T/KIR3DL2 Domain 0-eGFP. Positive subclones were injected into mice to produce ascites and antibodies of interest were purified before being tested in a Biacore assay using rec KIR3DL2 chips, followed by various assays formats based on binding to human KIR3DL2-expressing cells.

Sequences of the variable domains of heavy (VH) and light (VL) chain of antibodies were amplified by PCR from the cDNA of each antibody. Sequences amplified were run on agarose gel then purified using the Qiagen Gel Extraction kit. VH and VL sequences were then sub-cloned into the Lonza expression vectors (Double-Gene Vectors) using the InFusion system (Clontech) according to the manufacturer's instructions. After sequencing, vectors containing the VH and VL sequences were prepared as Maxiprep using the Promega PureYield™ Plasmid Maxiprep System. Vectors were then used for HEK-293T cell transfection using Invitrogen's Lipofectamine 2000 according to the manufacturer instructions. Antibodies generated included, inter alia, 10G5, 2B12, 19H12 and 12B11.

Epitope Mapping

Antibodies were further tested for binding to a series of KIR3DL2 mutants. Antibodies 19H12 and 12B11 did not show any loss of binding to un-mutated wild type KIR3DL2 (WTaKIR3DL2), but lost binding to mutant 11 having P179T and S181T substitutions as well as to mutant 11A1 having V178A and H180S substitutions. The principal epitope of these antibodies 19H12, 18B10 and 12B11 therefore includes residues P179, S181, V178 and/or H180. These residues at positions 179 and 181 in mutant 11 correspond to the residues present at in KIR3DL1 (KIR3DL1 has T179 and T181). Residues P179 and S181 in particular are within the D1 domain of KIR3DL2 and on the opposite face on the KIR3DL2 protein of the HLA-binding regions (i.e. the HLA binding pocket). Each of antibodies 15C11, 19H12, 18B10 and 12B11 had reduced binding (full loss of binding for 15C11 and 19H12) to mutant M11A4 having substitutions E130S, H131S and R145S. These residues at positions 179 and 181 in mutant 11 correspond to the residues present at in KIR3DL1 (KIR3DL1 has T179 and T181). Residues P179 and S181 in particular are within the D1 domain of KIR3DL2 and on the opposite face on the KIR3DL2 protein of the HLA-binding regions (i.e. the HLA binding pocket). Surface-exposed residues adjacent to these mutated residues can also contribute to the epitopes of the antibodies, including for example residues N99, H100, E130, H131, F132, V178, H180, P182, Y183, and Q184 (reference to SEQ ID NO: 1) located at the surface of KIR3DL2 in the region of the P179/S181 epitope but outside of the region of the KIR3DL2 mutations which did not result in loss of binding of the antibodies (e.g., mutant 5 (residue P66) and mutant 8 (residues V127)). Antibody 2B12 had loss of binding to mutants having I60N and G62S substitutions and decrease in binding to mutants having P14S, S15A and H23S substitutions, but did not lose binding to any other mutants. The principal epitope of these antibodies therefore includes residues I60 and/or G62 (and the epitope optionally further includes one or more of P14, S15, and H23). Residues 60 and 62 are within the D0 domain of KIR3DL2. Residues 14, 15, 23, 60 and 61 are within the D0 domain of KIR3DL2.

Antibodies Increase the Number of Available Cell Surface KIR3DL2 Receptors

Part 1:

Impact of Staining Conditions on 2B12 Labelling of KIR3DL2-Expressing Cells

This study aimed to evaluate the impact of staining conditions on 2B12 labelling of KIR3DL2-expressing cells, gated on total cells, at 4° C. or 37° C., and with incubation times of 2 hours, 4 hours or 24 hours. Briefly, 100,000 HUT78 cells per well were incubated with a dose range of 2B12 antibody starting from 0.0005 μg/ml to 30 μg/ml (serial dilution 1/3 in complete medium). The protocol used was as follows: incubation 2H; 4H and overnight at 4° C. and 37°; staining in RPMI 10% with or without PFA fixation; 2 washes in SB (150 μl/w); addition of anti-human-Fc PE for 30 min at 4° C.; 2 washes in SB (100 μl/w); and detection using FACS CANTO II.

Results are shown in FIG. 1A. While incubation at 4° C. which inhibits receptor internalization/cycling was expected to result in an at least equal level of available cell-surface KIR3DL2, staining with antibody 2B12 (human IgG1) was higher at 37° C. than at 4° C. Furthermore, higher median fluorescence was observed with increasing duration of incubation, the greatest KIR3DL2 expression was observed after 24 hours of incubation.

Part 2:

Total, Free and 2B12-Bound KIR3DL2 Detection on HUT78 Tumor Cells after Overnight Incubation This study aimed to evaluate the impact of a 20 hour incubation with antibody 2B12 on cell surface KIR3DL2 level by observing the amount of bound 2B12 (human IgG1), free (non-antibody bound) cell surface KIR3DL2 polypeptide, and total cell surface KIR3DL2 polypeptide. Briefly, HUT78 (100,000 cells/well) were incubated for 20 h at 37° C. with a dose range of 2B12 antibody starting from (decreasing) 8.88 μg/ml, 1/3 serial dilution, 11 concentrations. Dose ranges were made in duplicate in order to perform the following 2 staining conditions:

Total KIR3DL2+bound KIR3DL2 (GaH IgG Fc-PE+ mAb2-APC (a non-competing anti-KIR3LD2 mAb) (10 μg/ml)

Free KIR3DL2: 2B12-PE (10 μg/ml).

Staining was performed at 4° C. in staining buffer for 1 h and analyzed with a FACS Canto 11 HTS. Results are shown in FIG. 1B. The dark line/squares represents antibody 2B12 while the light line/circles represents isotype control. It can be seen that free KIR3DL2 receptors can be detected when incubating cells with 10 μg/ml of 2B12-PE and detecting free receptors with non-competing anti-KIR3DL2 antibody. It can be seen that 2B12-bound KIR3DL2 receptors can be detected by incubating cells with goat anti-human IgG Fc-PE secondary Ab. Both read-outs were correlated, with similar $EC_{50}$. The rightmost panel shows that a 20 hour incubation with 2B12 increases KIR3DL2 receptor level at cell surface as detected by the non-competing anti-KIR3DL2 antibody mAb2-APC. Antibody 2B12 may be causing conformational change upon binding, receptor stabilization/accumulation at cell surface and/or internalization/recycling blockade.

Part 3:

Total, Free and 2B12-Bound KIR3DL2 Detection on HUT78 Tumor Cells after 1, 24 or 48 Hours This study aimed to evaluate the dynamics of KIR3DL2 receptor expression by observing the amount of total, free and 2B12-bound KIR3DL2 after different periods of incubation with antibody 2B12. Briefly, HUT78 cells (50,000 cells/well) were incubated for 1 h, 24 h or 48 h at 37° C. in complete medium with 2B12 (human IgG1), dose range starting from 10 μg/ml (decreasing), 1/3 serial dilution, 11 concentrations, or with isotype control (IC), dose range starting (decreasing) from 10 μg/ml, 1/3 serial dilution, 11 concentrations. Dose ranges were made in triplicate in order to perform 3 staining conditions:

Bound KIR3DL2 (30 min at 4° C.): GaH IgG Fc-PE,

Free KIR3DL2+total KIR3DL2 (1 h at 4° C.): 2B12-PE (10 μg/ml)+mAb2-APC (non-competing anti-KIR3DL2) (10 μg/ml), Total KIR3DL2 (1 h+30 min at 4° C.): 2B12 (10 μg/ml)+ GaH IgG Fc-PE.

Staining was performed at 4° C. in staining buffer, and analysis conducted with HTFC Intellicyt.

Results are shown in FIG. 1C. In these culture conditions (96 well-plates, 50,000 HUT78/well at TO), KIR3DL2 detection at cell surface decreases in the absence of any Ab (as detected by mAb2-APC, 2B12-PE or 2B12+GaH-PE, points on the Y-axis).

Incubation with 2B12 at 37° C. increases surface expression of KIR3DL2 (as detected by non-competing mAb2 or by 2B12 itself+secondary Ab), in a dose-dependent manner. Isotype control did not give rise to any change in KIR3DL2. This increase is already observed after 1 h at 37° C., and seems to reach its maximum after 24 h. Staining is optimal after 24 h (in terms of total staining and of detected Ab-bound receptors).

Antibodies do not Internalize into Sezary Syndrome Cell Line

Internalization of antibodies 10F6, 2B12, 18C6, 9E10, 10G5, 13H1, 4B5, 5H1, 1E2, 1C3 and 20E9, as well as antibody AZ158 (an anti-domain 0 mAb as comparator) and other anti-D1 antibodies as disclosed in PCT applications WO2014/044686 and WO2014/044681 were assessed by fluoro-microscopy using the HUT78 SS cell line.

Materials and Methods:

Hut-78 cells were incubated during 1H at 4° C. with 10 μg/ml of the different antibodies. After this incubation cells were either fixed (t=0H) or incubated for 2H at 37° C. Cells incubated for 2H were then fixed and stained. Antibodies were stained using goat anti-mouse antibodies coupled to Alexa594 (Invitrogen, A11032). LAMP-1 compartments were stained using rabbit anti-LAMP-1 antibodies (Abcam, ab24170) revealed by goat anti-rabbit polyclonal antibodies coupled to FITC (Abcam ab6717). Pictures were acquired using an Apotome device (Zeiss) and analyzed using the Axiovision software.

Results:

Anti-KIR3DL2 mAbs were visible in red while LAMP-1 compartments were visible in green. At the time of addition of antibodies, KIR3DL2 staining in red was visible at the cell surface while green LAMP-1 were visible intracellularly in green. However, at 2 hours following the addition of antibodies, each of antibodies AZ158, 13H1 and 4B5, and anti-D1 antibodies caused red staining to be colocalized with green staining, along with a decrease in red staining at the cell surface, indicating that AZ158, 13H1 and 4B5, and anti-D1 antibodies were rapidly internalized. Antibodies 10F6, 2B12, 18C6, 9E10, 10G5, 5H1, 1E2, 1C3 and 20E9, however was not internalized, and at 2 hours following the addition of antibody, red staining remained entirely on the cell surface.

Antibodies are able to kill KIR3DL2 expressing targets via antibody dependent cellular cytotoxicity (ADCC)

Cell lysis through an ADCC mechanism was monitored in a radioactivity-based $^{51}$Cr release experiment (the level of radioactivity released from the preloaded target cells being proportional to their death). One million target cells were loaded with $^{51}$Cr for 1 hour at 37° C. and washed 3 times. 3,000 cells were seeded per well (U-shaped bottom 96-well plates) and test mAbs are added at 10 or 20 μg/ml final concentration (or increasing concentrations if dose-response relationship is studied). Effector cells were added at a defined effector:target ratio (in general 10:1) and the mixture was incubated at 37° C. for 4 h. Supernatant is analyzed on a Lumaplate apparatus.

Anti-KIR3DL2 mAbs selected in Example 1 were tested at the same final concentration (10 μg/ml), to kill KIR3DL2-transfected B221 target cells. The mAbs were effective in mediating ADCC against KIR3DL2-expressing B221 targets.

Example 2—Activity in Mouse Xenograft Models of KIR3DL2 Expressing Human Tumors

Tumor cells lines B221 and RAJI were made to express human KIR3DL2. Immune compromised mice used for B221-KIR3DL2 and RAJI-KIR3DL2 models were NOD-SCID purchased from Charles River Laboratories. In the following models, 5 million human B221-KIR3DL2 or RAJI-KIR3DL2 tumor cells (in 100 μl PBS as vehicle) were engrafted IV on Day 0 (D0), i.e. 1 day before treatment initiation (D1). From D1, mice were treated IV with different doses of anti-KIR3DL2 mAbs (doses were adapted to mouse body weight) diluted in PBS, 2 injections per week for the duration of the whole experiment.

Control groups included, depending on the experiment:
 PBS/placebo-treated mice as a control of normal/unaffected tumor growth;
 mice injected with the same dose of isotype control-matched mAbs directed against an irrelevant antigen.

Mice were weighed and observed for clinical signs every 2 to 5 days depending on the model. Percent of body weight changes were calculated as compared to body weight at D0 before tumor engraftment or to the highest body weight reached during the experiment. Mouse deaths or important weight losses were recorded and used to draw survival Kaplan-Meier curves and calculate improvement in survival as compared to control groups of mice.

The efficacy of IgG2b isotype murine anti-KIR3DL2 19H12 antibodies (given at 300 μg/mouse, twice a week) was separately tested against SC B221-KIR3DL2 xenografts or RAJI-KIR3DL2 xenografts (n=6 NOD-SCID mice per group). Animals treated with anti-KIR3DL2 antibodies showed an increase in survival in comparison to mice treated with isotype control-matched mAbs.

Example 3—Improved Detection Methods Reveal KIR3DL2 Positive Tumors

Tumor biopsies from RAJI-KIR3DL2 models and RAJI-KIR3DL2 cell lines were obtained and staining was performed on frozen sample using AZ158 antibody (see WO2010/081890) or antibodies 12B11 (see Example 1). KIR3DL2 was stained with anti-KIR3DL2 antibody by DAB chromogenic detection according to standard protocols, adapted for immunostaining with BenchMark XT Ventana Roche. For all staining control isotype (mIgG1) and control DAB were performed. Surprisingly while AZ158 was negative, tumors were positive when using 12B11 antibody at the same concentration (5 μg/ml) of antibody (see FIG. 1). Raising concentrations of antibody AZ158 (to 50 μg/ml) generated extensive background staining that did not allow tumor samples to be differentiated from healthy tissue.

Next, tumor biopsies from cancer patients previously stained with AZ158 were re-examined using antibody 12B11. Biopsies that had been KIR3DL2-negative with AZ158 were stained with 12B11 (i.e. becoming KIR3DL2-positive).

Example 4: NK Lytic Capacity Assay

Cell lysis through an ADCC mechanism was monitored in a radioactivity-based $^{51}$Cr release experiment (the level of radioactivity released from the preloaded target cells HUT78 (ATCC reference TIB-161™, available from LGC Standards Corp.) being proportional to their death). Briefly, human peripheral blood mononuclear cells (PBMCs) from healthy donors were incubated with HUT78 target cell line (KIR3DL2$^+$) in the presence of a dose range of IPH4102 mAb (humanized 2B12 mAb). HUT78 cell lysis by PBMCs was monitored in a 4-hour chromium release assay, using an E:T ratio of 100.

Effector Cell Preparation

Human blood was withdrawn on CPT tubes (n=6 to 8 tubes per donor containing 7-8 ml of blood). Within 30 minutes after collection, CPT tubes were centrifuged for 30 minutes at 1500 g with low acceleration and low brake, at room temperature (RT). After centrifugation, the mononuclear cells, in the supernatant above the separation gel, were transferred into 50 ml conical tubes (contents of 2 to 3 CPT tubes were pooled into one 50 ml tube), completed to 50 ml with RPMI-1640 and centrifuged for 10 minutes at 600 g at RT. All cell pellets were pooled into one 50 ml conical tube and washed with 50 ml of RPMI-1640 (centrifugation 10 min, 130 g, RT). Remaining red blood cell (RBC) lysis could be performed at this step, by adding 1 ml of cold NH$_4$Cl on cell pellet and incubating 5-10 min at RT. When RBC lysis was necessary, an additional washing step was performed by filling the tube to 50 ml with RPMI-1640 (centrifuged 10 min, 130 g, RT). Cell pellet was resuspended in 20 ml of CCM, and PBMCs were counted by excluding dead cells with Trypan blue stain, using Cellometer cell counter.

PBMC concentration was adjusted with CCM to 6×10$^6$ cells/mi for target cell lysis assay ($^{51}$Cr release, 50 µl/w=3× 10$^5$ cells), and to 2.5×10$^6$ cells/mi for NK cell activation assay (CD137 expression, 50 µl/w=1.25×10$^5$ cells).

Target Cell Preparation

HUT78 target cells were counted by excluding dead cells with Trypan blue stain, using Cellometer cell counter. 2.10$^6$ cells were labelled with $^{51}$Cr, by adding 50 µCi of $^{51}$Cr per 10$^6$ cells on cell pellet in round-bottom 14 ml polypropylene tube, and incubated 1 h at 37° C. After chromium labeling, cells were washed 3 times with 10 ml of CCM (centrifugation 5 min, 500 g, RT). Cells were counted by excluding dead cells with Trypan blue stain, using Kovaslide. Cell concentration was adjusted to 3×10$^4$ cells/mi (100 µl/w=3× 10$^3$ cells).

mAb Solution Preparation

4× solutions (50 µl/w in 200 µl/w final) of anti-KIR3DL2 antibody (1.6 ml), negative isotypic control, 1.6 ml) and alemtuzumab (anti-CD52, positive control, 1.2 ml) were prepared in CCM and centrifuged for 10 min at maximal speed (16100 g) at 4° C. in a benchtop centrifuge (to eliminate potential aggregates).

The highest tested concentration was 10 µg/mi (i.e. 40 µg/mi as a 4× solution) for isotype control and alemtuzumab and 8.88 µg/mi (i.e. 35.5 µg/mi as a 4× solution) for anti-KIR3DL2 antibody. 1/4 serial dilutions were performed in 96-deepwell plate for isotype control and anti-KIR3DL2 antibody, by transferring 400 µl of mAb solution into 1.2 ml of CCM. Eleven concentrations were tested for both Abs, whereas alemtuzumab was only tested at 10 µg/ml.

Assay Procedures mAb solutions (50 µl/w) were transferred from the 96 deepwell plate into U-bottom plate, in triplicate. Effector cells (PBMCs, 50 µl/w) and target cells loaded with $^{51}$Cr (HUT78, 100 µl/w) were added to the wells. Final E/T ratio is 100/1. Spontaneous and maximal chromium release from target cells were measured in dedicated wells (n=8 per plate) containing respectively target cells in medium and target cells in medium+2% Triton X-100. The plates were centrifuged for 1 minute at 300 g before incubation at 37° C. for 4 hours. After the 4 h-incubation, plates were centrifuged for 3 minutes at 300 g, and 50 µl of supernatants were transferred into Lumaplate containing scintillator. Supernatants were allowed to dry at 56° C., and chromium released into culture supernatants was quantified using TopCount NXT™ microplate scintillation counter (Perkin Elmer).

Specific lysis of target cells was calculated using the following formula:

$$\text{specific lysis (\%)} = \frac{(\text{experimental release} - \text{spontaneous release})}{(\text{maximal release} - \text{spontaneous release})} \times 100$$

Example 5—Development of a Model Based on NK Cell % Lytic Activity to Determine Dosing of Anti-KIR3DL2 Antibodies Pharmacokinetic of therapeutic mAbs is usually modelled using a two-compartment model (Dirks and Meibohm, 2010; Lobo et al., 2004; Morell et al., 1970; Roskos et al., 2004). Anti-KIR3DL2 antibody 2B12 obtained according to Example 1 was humanized (VH and VL amino acid sequences shown in Table D; see also WO2015/136052, the disclosure of which is incorporated herein by reference); the antibody (referred to as IPH4102) was produced as a full-length human IgG1 isotype antibody and evaluated in cynomolgus monkeys and mice. Based on preclinical PK results in both cynomolgus monkeys and mice, IPH4102 is expected to display PK properties similar to other therapeutic mAbs in humans, except for compound-specific target-mediated effects. In SS and MF patients, IPH4102 will bind KIR3DL2$^+$ tumor cells in blood and in tissues, in addition to KIR3DL2$^+$ normal lymphocytes. It is anticipated that target-mediated drug disposition (TMDD) may influence the PK of IPH4102 in humans. Hence, parameters for describing TMDD were included in the PK model.

Figure 2:
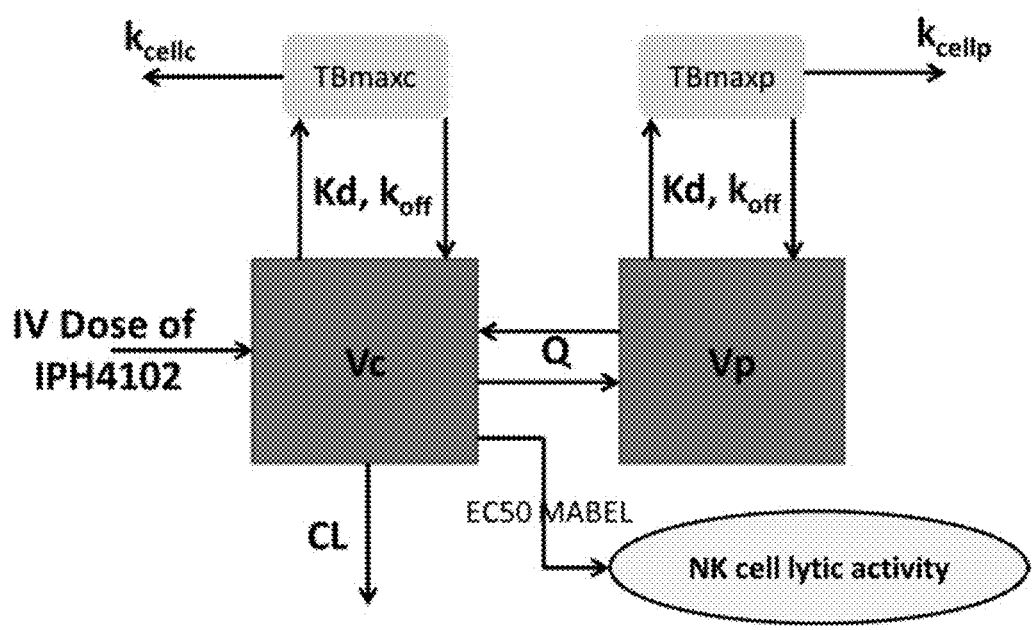
FIG. 2 shows the PK simulation model for IPH4102, a two-compartment model with parallel first order and saturable elimination pathways.

The final PK simulation model was a two-compartment model with parallel first order and saturable elimination pathways, as illustrated in FIG. 2. This TMDD model can be used to describe the anticipated human PK for IPH4102, and includes:

Two-compartment distribution (from blood to periphery), characterized by an inter-compartmental clearance (Q) and distribution volumes for the central and peripheral compartments (respectively Vc and Vp).

First order elimination from the central compartment, characterized by a single clearance parameter, CL.

A central and a peripheral maximum Target Binding capacity (TB$_{maxc}$ and TB$_{maxp}$, respectively), describing the amount of IPH4102 which may be bound by the available KIR3DL2 antigen at full saturation in the central and peripheral compartment, respectively. The dynamics in the system are characterized by a rate constant for association, K$_m$, a rate constant for dissociation, K$_{off}$, and a turnover rate for the KIR3DL2-positive cells, K$_{cell}$. In practice the rate constant for association, K$_{on}$, was determined as K$_{on}$=K$_{off}$/K$_D$, where K$_D$ is the affinity of IPH4102 for binding to KIR3DL2.

The PK model was extended to include a link between the predicted serum concentration of IPH4102 and NK cell lytic capacity in humans, as well as KIR3DL2 saturation prediction.

A standard E max-type relationship with a single potency parameter, EC$_{50}$, was used to describe the link between IPH4102 concentration (Conc) and NK lytic capacity, as measured for instance in $^{51}$Cr release assay, by the percentage of maximal tumor cell lysis obtained (=Tumor cell lysis/Max tumor cell lysis at saturation×100):

% NK lytic capacity=100×Conc/(Conc+EC$_{50}$)

The maximal Target Binding (TB$_{max}$) in a compartment for a therapeutic mAb can be calculated as follows: TB$_{max}$=Rec×C$_{cell}$×V×A$_N$×MW$_{mAb}$×10$^9$ where:
Rec is the receptor density=number of Target Receptors/cell,
$C_{cell}$ is the concentration of target positive cells in the compartment (number/mL),
V is the volume of the compartment,
$A_N$ is Avogadro's number for converting number of entities to moles=$6.023 \times 10^{23}$/mol,
$MW_{mAb}$ is the molecular weight of IPH4102=150,000 g/mol, and
$10^9$ converts from g to ng.

Figure 1B:
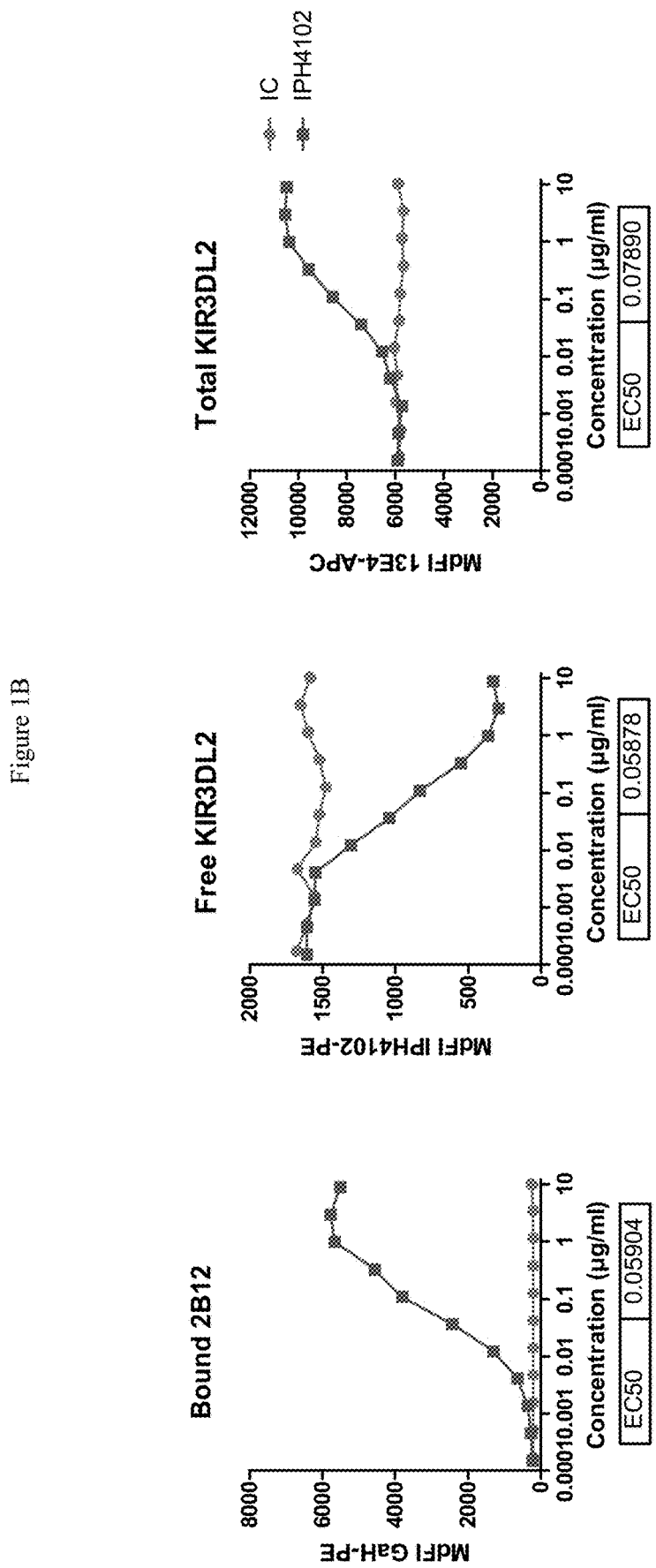
FIG. 1B shows the effect of antibody 2B12 (dark line/squares) and isotype control (light line/circles) of KIR3DL2 levels. It can be seen that free receptors and 2B12-bound KIR3DL2 receptors read-outs were correlated, with similar $EC_{50}$. The rightmost panel shows that a 20 hour incubation with 2B12 increases total KIR3DL2 receptor level at cell surface as detected by non-competing anti-KIR3DL2 (mAb2) linked to APC.
Figure 1C:
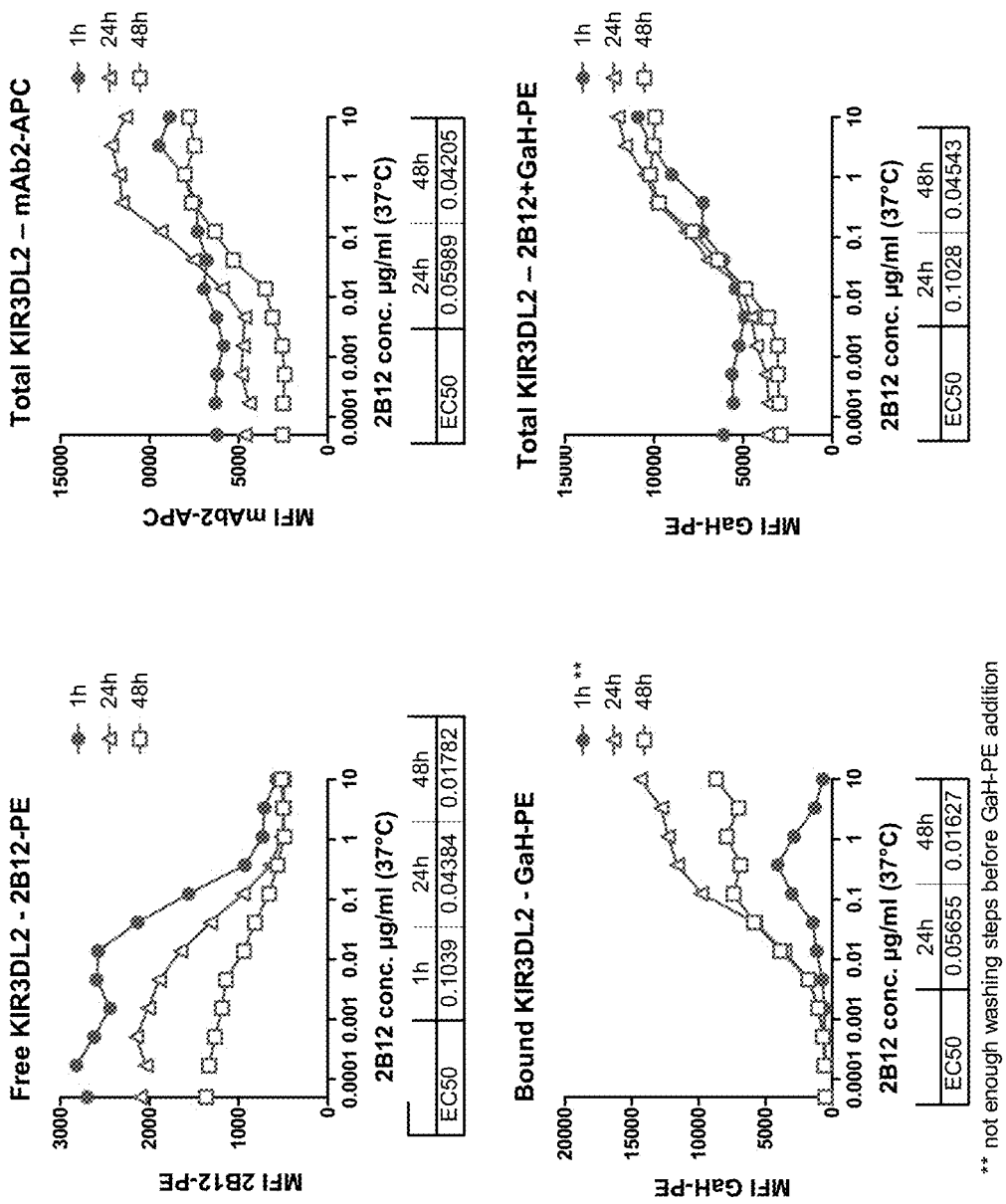
FIG. 1C shows that incubation at 37° C. with antibody 2B12 increases surface expression of KIR3DL2 (as detected by non-competing anti-KIR3DL2 (mAb2) or by 2B12 itself+secondary Ab), in a dose-dependent manner. This increase is already observed after 1 h at 37° C., and seems to reach its maximum after 24 h. Staining is optimal after 24 h (in terms of total staining and of detected Ab-bound receptors).

The structure of PK/PD model is described in FIG. 1. Parameters for each compartment of the model were derived based on in vitro data and literature information, as further described below.

Values for the parameters (CL, Vc, Q, Vp) were identified based on preclinical PK results in both cynomolgus monkeys and mice, showing that IPH4102 is expected to display PK properties similar to other therapeutic mAbs in humans, defining a standard two-compartment model for an IgG in humans.

Target binding capacity to normal immune cells in blood was determined. Briefly, the total number of KIR3DL2 expressing lymphocytes was determined using results from a non-interventional, mono-centric descriptive and prospective open study in healthy volunteers. A total of 40 volunteers were enrolled divided in two cohorts, cohort 1 with 20 volunteers under the age of 60 years old and cohort 2 with 20 volunteers over the age of 61. The number of white blood cells (WBC) given by the blood formula of each donor was used to normalize flow cytometry data. Fresh whole blood samples were processed and analyzed with a panel of fluorochrome-conjugated mAbs (8-colors combinations) to define blood cell subsets. The gating strategy in flow cytometry aimed to express each cell subset as a percentage of WBC. By using these percentages and the WBC number from the blood formula, the different blood cell subsets were defined in cells per μL of blood. The absolute number of KIR3DL2$^+$ immune cells populations among lymphocytes (mean value of 1 to 10 tubes) and the MESF at saturation, using PE-labelled anti-KIR3DL2 mAb (mean value of 1 to 10 tubes) were used to calculate the total number of KIR3DL2 receptors on lymphocytes in humans.

No specific information about the tissue-to-blood ratio for KIR3DL2$^+$ lymphocytes was available initially. Consequently, target binding capacity to normal immune cells in tissues was estimated based on the number of blood lymphocytes that express KIR3DL2, and the assumption that KIR3DL2$^+$ cells had a distribution similar to the general distribution of other lymphocytes, where the number of cells in the tissue is approximately 50 times higher than in the blood. KIR3DL2 receptor density was assumed to be comparable between blood and tissue.

Target binding capacity to leukemic tumor cells in blood, for SS patients was assessed. For evaluation of IPH4102 target binding to blood tumor cells in SS patients, the total number of KIR3DL2$^+$ tumor cells was determined in 9 SS patients based on blood formula counts and % of CD3$^+$CD4$^+$KIR3DL2$^+$ cells among whole blood cells, using PE-labelled anti-KIR3DL2 mAb. The number of KIR3DL2 molecules expressed at the cell surface of primary Sézary tumor cells was determined for each patient. Mean of all measurements of absolute number of KIR3DL2$^+$ tumor cells (CD4$^+$CD3$^+$KIR3DL2$^+$) was calculated. The KIR3DL2 density at the cell surface of SS tumor cells was evaluated.

For target binding capacity to tumor cells in tissues, no specific information about the total number of tumor T cells in skin was initially available for CTCL patients. As total skin resident T cells were evaluated to 20 billion cells, it was postulate that total tumor KIR3DL2$^+$ T cells would not largely exceed this level, and that median KIR3DL2 density on tumor cells, assumed to be similar to circulating tumor cells in SS patients. The result was that TB max resulting for tumor cells in tissues was found in same range as target binding capacity of IPH4102 to KIR3DL2 on circulating tumor cells as observed in SS patients.

Mechanisms for target-mediated disposition were limited to regular turnover of NK and of tumor cells, assumed to be independent of IPH4102 concentration.

In vitro affinity ($K_D$) and off-rate ($K_{off}$). IPH4102 in vitro binding affinity for KIR3DL2 was evaluated with PE-labelled IPH4102 in concentration-response flow cytometry experiments performed on KIR3DL2-transfected cell lines, on KIR3DL2 expressing Sézary Syndrome (SS) tumor cell lines and on SS primary tumors collected from patient blood samples. The concentration-response for IPH4102 binding to KIR3DL2 was confirmed in flow cytometry experiments on whole blood from healthy volunteers, gated on NK cells and in surface plasmon resonance (SPR) experiments using recombinant human KIR3DL2 protein (average bivalent binding affinity on Biacore).

In vitro concentration-response binding experiments with IPH4102 on KIR3DL2$^+$ Sézary cell lines (such as HuT78 or COU-L) and on primary Sézary tumor cells revealed that, regardless of KIR3DL2 expression level, the $EC_{50}$ for IPH4102 binding on cell lines and primary Sézary cells are similar (0.06 μg/mL with HuT78, 0.087 μg/ml for COU-L, 0.07 μg/mL on patients' primary tumor cells). In conclusion, the binding affinity of IPH4102 to tumor and immune cells in blood was set to 70 ng/ml in the PK/PD model. PE-labelling had only small impact on IPH4102 affinity for KIR3DL2, in overnight staining conditions. Importantly, a similar affinity was found in SPR (IPH4102 average bivalent binding affinity to recombinant KIR3DL2 on Biacore, 0.146 nM, corresponding to 21.9 ng/mL, shown in the Table below. The off-rate for dissociation of IPH4102 from recombinant KIR3DL2 was obtained from SPR experiments. The KIR3DL2 antigen binding activity was determined using a two-step experimental set-up. Firstly, IPH4102 samples were injected at a constant concentration over the Protein-A chip (antibody capture step). Secondly, KIR3DL2-His antigen samples were injected at a constant concentration over the captured antibodies (antigen binding step) and allowed to dissociate before injection of a regeneration buffer for baseline correction (blank subtraction). For batch to batch comparison the mean (n=3) reflectance unit (RU) ratio between bound antigen and captured antibody was used as a comparative index (0.4).

The mean of three determinations of the off-rate for bivalent binding was used ($1.4 \times 10^{-4}$ s$^{-1}$, corresponding to 0.504 h$^{-1}$).

TABLE

| KIR3DL2 binding affinity by SPR | | | | |
|---|---|---|---|---|
| | $K_D$ (nM) | | | |
| | N = 1 | N = 2 | N = 3 | Mean $K_D$ |
| $K_D$ (nM) | 0.1616 | 0.1314 | 0.1436 | 1.46E−01 |
| $K_{on}$ (1/Ms) | 9.68E+05 | 9.53E+05 | 9.65E+05 | 9.62E+05 |
| $K_{off}$ (1/s) | 1.56E−04 | 1.25E−04 | 1.39E−04 | 1.40E−04 |

In order to evaluate biological and potential toxic activity of IPH4102 in a physiological setting, the in vitro concentration-response assay of IPH4102 was determined in vitro on 15 human healthy donor PBMCs co-incubated with HuT78 cells and increasing doses of IPH4102 mAb. Three read-outs were studied in parallel: the activation of NK cells through CD137 expression (flow cytometry), the lysis of target cells by PBMCs (classical $^{51}$Cr-release assay) and the secretion of 5 cytokines and chemokines: IFN-γ, TNF-α, IL-6, IL-8, MCP-1. Briefly, PBMCs from healthy donors were incubated with HuT78 target cell line (KIR3DL2$^+$) in the presence of a dose range of IPH4102 mAb. The activation of NK cells among PBMCs after 20 hours of incubation was monitored using the activation marker CD137, using an E:T (Effector:Target) ratio of 2.5:1. Cytokines produced by PBMCs in culture supernatants during the 20 h-incubation (CD137 assay) were quantified with AlphaLISA technology (Perkin Elmer). In parallel, HuT78 cell lysis by PBMCs was monitored in a 4-hour $^{51}$Cr-release assay, using an E:T ratio of 100:1, as described in Example 4.

The parameter the most relevant to IPH4102 safety and pharmacological activity for determination of dosing was selected as HuT78 tumor cell lysis by healthy donors' PBMC in the $^{51}$Cr release assay (NK cell lytic capacity). The median $EC_{10}$ and $EC_{50}$ (±SD) in the $^{51}$Cr release assay were respectively 2 (±2.8) ng/mL and 45 (±40) ng/mL.

Hence, a standard E max-type relationship with a single potency parameter, the $EC_{50}$ of IPH4102 in the $^{51}$Cr release assay, i.e. =45 ng/mL, was used to describe the link between IPH4102 concentration (Conc) and % of maximal ability of NK cells to mediate tumor cells lysis, as measured by % of NK lytic capacity:

% of NK lytic capacity=100×Conc/(Conc+$EC_{50}$)

The final parameters are summarized in the table below.

TABLE

Summary of IPH4102 PK/PD model parameters

| Parameter | Description | Value |
|---|---|---|
| CL | Clearance | 0.12 mL/h/kg |
| Vc | Central volume of distribution | 40 mL/kg |
| Q | Inter compartmental clearance | 1 mL/h/kg |
| Vp | Peripheral Volume of distribution | 40 mL/kg |
| Kcellc | Turnover rate of KIR3DL2-positive cells (lymphocytes and tumor cells) in blood | 0.003/h for HD and MF; 0.02/h for SS |
| Kcellp | Turnover rate of KIR3DL2-positive cells (lymphocytes and tumor cells) in periphery | 0.003/h for HD; 0.02/h for MF and SS |
| $K_{off}$ | Dissociation rate constant | 0.504/h |
| $K_D$ | Binding affinity | 70 ng/mL |
| $TB_{maxc}$ | Target binding capacity in blood | 5 ng/kg for HD and MF; 198 ng/kg for SS |
| $TB_{maxp}$ | Target binding capacity in periphery | 257 for HD; 450 ng/kg for MF and SS |
| $EC_{50}$ | $EC_{50}$ in $^{51}$Cr-release assay HuT 78 tumor lysis by PBMC from healthy volunteers. | 45 ng/mL |

PD/PK simulations were then performed using the software Phoenix WinNonLin version 6.4 and plotting of the results was done in GraphPad Prism 5 version 5.04. The model was implemented in WinNonLin and used to simulate the PK over time following 1 hour i.v. infusion of IPH4102 to humans for a range of dose levels. Based on this, doses for the first-in-human (FIH) trial were identified. The selected pharmacological parameter for MABEL calculation was Hut 78 tumor cell lysis by healthy donor PBMC in a $^{51}$Cr release assay, which was a conservative evaluation of the biological IPH4102-mediated response in SS patients. We determined doses that would result in a low, but discernable effect in the in vitro assay of HuT 78 tumor lysis (see Example 4). A 10% response in this assay was adopted as a low MABEL response ($EC_{10}$=2 ng/mL). Hence, of particular interest was the dose resulting in the pre-defined 10% $^{51}$Cr-release at $C_{max}$. Based on the PK simulations, $C_{max}$, % of NK lytic capacity at $C_{max}$ and max KIR3DL2-occupancy achieved at t=3-6 h, were predicted for different doses in Healthy Donors, MF (no circulating tumor cells) and SS (circulating tumor cells) patients, and helped in identifying the FHD as 0.1 μg/kg.

Simulated $AUC_{0-7\ days}$ after $1^{st}$ and $4^{th}$ doses, $C_{max}$ and accumulation index for multiple dose phase I clinical study are presented in Table below, for MF and SS patients.

TABLE

Cmax and accumulation index for multiple dose phase I

| Dose Level μg/kg | Dose fold increase | $C_{max}$Cycle 1 (6 h) ng/ml | $C_{trough}$Cycle 1 (168 h) ng/ml | $C_{max}$Cycle 4 (510 h) ng/ml | $AUC_{7days}$ Cycle 1 ng*h/mL | $AUC_{7days}$ Cycle 4 ng*h/mL | Accumulation Index |
|---|---|---|---|---|---|---|---|
| MF0.1 | — | 2 | 1 | 4 | 176 | 373 | 2.67 |
| 1 | x10 | 22 | 7 | 37 | 1770 | 3923 | 2.67 |
| 10 | x10 | 216 | 82 | 407 | 18476 | 47084 | 2.68 |
| 50 | x5 | 1081 | 444 | 2138 | 95579 | 254699 | 2.69 |
| 200 | x4 | 4326 | 1824 | 8663 | 386736 | 1039066 | 2.70 |
| 750 | x3.75 | 16226 | 6890 | 32597 | 1455032 | 3916529 | 2.72 |
| 1500 | x2 | 32454 | 13799 | 65235 | 2911884 | 7840478 | 2.74 |
| 3000 | x2 | 64909 | 27617 | 130511 | 5825602 | 15688410 | 2.82 |
| 6000 | x2 | 129820 | 55253 | 261062 | 11653058 | 31384281 | 3.01 |
| 10000 | x1.6 | 216368 | 92101 | 435131 | 19423001 | 52312143 | 3.29 |
| SS0.1 | — | 2 | 1 | 3 | 161 | 318 | 2.35 |
| 1 | x10 | 21 | 7 | 34 | 1639 | 3412 | 2.35 |
| 10 | x10 | 213 | 77 | 394 | 17818 | 44704 | 2.36 |
| 50 | x5 | 1077 | 436 | 2121 | 94584 | 251534 | 2.36 |
| 200 | x4 | 4322 | 1815 | 8645 | 385644 | 1035723 | 2.37 |
| 750 | x3.75 | 16222 | 6881 | 32579 | 1453914 | 3913141 | 2.38 |
| 1500 | x2 | 32449 | 13790 | 65216 | 2910759 | 7837082 | 2.39 |

TABLE-continued

Cmax and accumulation index for multiple dose phase I

| Dose Level µg/kg | Dose fold increase | $C_{max}$Cycle 1 (6 h) ng/ml | $C_{trough}$Cycle 1 (168 h) ng/ml | $C_{max}$Cycle 4 (510 h) ng/ml | $AUC_{7days}$ Cycle 1 ng*h/mL | $AUC_{7days}$ Cycle 4 ng*h/mL | Accumulation Index |
|---|---|---|---|---|---|---|---|
| 3000 | x2 | 64905 | 27607 | 130492 | 5824478 | 15685020 | 2.43 |
| 6000 | x2 | 129815 | 55243 | 261043 | 11651930 | 31380900 | 2.57 |
| 10000 | x1.6 | 216363 | 92091 | 435112 | 19421868 | 52308744 | 2.81 |

At a dose of 0.1 µg/kg, in MF and SS patients, KIR3DL2-occupancy would remain below 3% and the % of NK lytic capacity mediated by IPH4102-stimulated NK cells will remain below 6%. The tables below summarize, for MF and SS patients, respectively, the simulations in terms of the expected values of the % of NK lytic capacity in circulation at $C_{max}$ and $C_{trough}$, for cycle 1 and cycle 4 of repeated weekly administrations in MF patients, for the dose levels up to 1500 µg/kg.

TABLE

MF patients

| Dose Level µg/kg | % of NK lytic capacity at $C_{max}$ cycle 1 (6 h) | % of NK lytic capacity at $C_{trough}$ cycle1 (168 h) | % of NK lytic capacity at $C_{max}$ cycle 4 (510 h) | % of NK lytic capacity at $C_{trough}$ cycle 4 (672 h) |
|---|---|---|---|---|
| 0.1 | 5 | 2 | 7 | 4 |
| 1 | 32 | 14 | 45 | 28 |
| 10 | 83 | 65 | 90 | 84 |
| 50 | 96 | 91 | 98 | 97 |
| 200 | 99 | 98 | 99 | 99 |
| 750 | 100 | 99 | 100 | 100 |
| 1500 | 100 | 100 | 100 | 100 |

TABLE

SS patients

| Dose Level µg/kg | % of NK lytic capacity at $C_{max}$ cycle 1 (6 h) | % of NK lytic capacity at $C_{trough}$ cycle 1 (168 h) | % of NK lytic capacity at $C_{max}$ cycle 4 (510 h) | % of NK lytic capacity at $C_{trough}$ cycle 4 (672 h) |
|---|---|---|---|---|
| 0.1 | 4 | 1 | 7 | 3 |
| 1 | 31 | 13 | 43 | 25 |
| 10 | 83 | 63 | 90 | 83 |
| 50 | 96 | 91 | 98 | 97 |
| 200 | 99 | 98 | 99 | 99 |
| 750 | 100 | 99 | 100 | 100 |
| 1500 | 100 | 100 | 100 | 100 |

Example 6—A Human Phase I Clinical Trial in Relapsed/Refractory CTCL

IPH4102 (humanized IgG1 anti-KIR3DL2 antibody 2B12) is currently being investigated in a first-in-human dose-finding phase 1 study (NCT02593045) evaluating repeated administrations of single-agent IPH4102 in relapsed/refractory CTCL patients.

The primary objective is to assess the safety and tolerability of increasing doses of IPH4102 by characterizing dose-limiting toxicity and adverse events. Secondary objectives include PK, immunogenicity and signals of anti-neoplastic clinical activity. Exploratory biomarkers aim to characterize KIR3DL2-expressing and non-expressing cells in involved tissue/compartments and to monitor their changes with IPH4102 treatment. Measurement of molecular residual disease is performed in the skin, blood and/or lymph nodes. Assessment of ex vivo NK cell-mediated ADCC against autologous tumor cells is also performed pre-dose on SS patients.

The study has two sequential portions, a dose-escalation followed by a cohort expansion portion. The dose-escalation portion has a 3+3 design with accelerated titration and aims to determine the maximal tolerated dose (MTD) or recommended phase 2 dose (RP2D). Doses tested included: 0.0001 mg/kg, 0.001 mg/kg, 0.01 mg/kg, 0.05 mg/kg, 0.2 mg/kg, 0.75 mg/kg, 1.5 mg/kg, 3 mg/kg, 6 mg/kg and 10 mg/kg body weight. In the expansion portion, two CTCL subtype-specific cohorts will be studied, each cohort to include 10 additional patients to further explore the MTD or RP2D. Eligible CTCL patients must have received at least 2 prior lines of anti-neoplastic systemic therapy. Centrally assessed KIR3DL2 expression on malignant cells in skin or blood is required for inclusion.

Patients received weekly IPH4102 administrations until progression or unacceptable toxicity. Intra-patient dose-escalation is allowed, only past the first complete clinical assessment at week 5 and provided the upper next dose-level is declared safe by the safety committee.

Among the 14 patients who were (or are still being) treated, 11 have SS, 2 have MF and 1 has CD4+ CTCL, Not Otherwise Specified (NOS). Clinical assessment was performed according to the published recommended standardized scoring system for assessing tumor burden and defining response in skin, lymph nodes, blood, and viscera, by using a composite global response score and a common definition of clinical end points described in Olsen et al. (2011) American Society of Clinical Oncology 29, 2598-2607. In this system, global complete response (CR) is defined as the complete disappearance of all clinical evidence of disease and can only be achieved if CR is documented in all involved organs, i.e. all TNMB categories. In contrast, any progressive disease (PD) in any TNMB category qualifies for global PD. In intermediate situations, the global scores of partial response (PR) or stable disease (SD) are achieved according to TNMB categories (described in Olsen et al. (2011), supra. Clinical assessment performed included:

full TNMB scoring (may require imaging) performed pre-dose and then at week 5 (W5), W14, W26 and then every 4 weeks until treatment discontinuation;

skin-specific mSWAT measurement is performed pre-dose, at week 5, then every 2 weeks until W26, then every 4 weeks; and assessment of blood involvement (through Sézary cell count or immuno-phenotyping or cytomorphology) is also performed pre-dose, at W5, then every 2 weeks until W26, then every 4 weeks.

The clinical trial is still ongoing. Clinical assessments for the patients remaining in the study are detailed in the table below:

| Patient | Initial dose (mg/kg) | Number doses admin | CTCL subtype | Stage at study entry | Objective best response | Treatment duration (days) |
|---|---|---|---|---|---|---|
| 1 | 0.0001 | 15 | SS | T4N0M0B2 | PR (week 22; 0.05 mg/kg) | >200 |
| 2 | 0.001 | 12 | SS | T4NxM0B2 | SD | 133 |
| 3 | 0.01 | 12 | MF | T2N0M0B0a | PR (week 10; 0.01 mg.kg) | 161 |
| 4 | 0.05 | 11 | Transformed SS | T4NxM0B2 | PR (week 10; 0.05 mg/kg) | 133 |
| 5 | 0.05 | 7 | MF | T2NxM0B0a | SD | 62 |
| 6 | 0.05 | 9 | SS | T2N0M0B2 | SD | 118 |
| 7 | 0.2 | 9 | SS | T4N2aM0B2 | SD | 91 |
| 8 | 0.2 | 7 | SS | T4N2M0B2 | SD | 64 |
| 9 | 0.2 | 7 | CD4 Tcell (NOS) | TxN0M0 | SD | 63 |
| 10 | 0.75 | 5 | SS | T1N0M0B2 | SD | 36 |
| 11 | 0.75 | 4 | SS | T4N0M0B2 | SD | 27 |

The table above also displays the dose-level at which each patient entered the trial, the number of IPH4102 administrations they received, the CTCL subtypes and the TNMB stage at study entry. Three patients experienced global PR, which have lasted respectively for 28, 74 and 70 days and are still ongoing. Timing of occurrence of these responses as well as the dose-level that was received at occurrence are shown in the same column.

Specifically for Sézary Syndrome patients, particular attention was given to clinical response in blood. Among the five SS patients enrolled in the study, two have achieved PR and one has achieved CR in blood, as shown in the table below.

| Patient | Initial dose (mg/kg) | Number doses admin | CTCL subtype | Stage at study entry | Sezary count baseline (cells/µL) | Sezary count nadir (cells/µL) | Best response in blood (1$^{st}$ observation) |
|---|---|---|---|---|---|---|---|
| 1 | 0.0001 | 13 | SS | T4N0M0B2 | 5273 | 507 | PR (week 5) |
| 2 | 0.001 | 11 | SS | T4NxM0B2 | 19219 | 3407 | PR (week 14) |
| 4 | 0.05 | 7 | Transformed SS | T4NxM0B2 | 4644 | 76 | CR (week 10) |
| 6 | 0.05 | 7 | SS | T2N0M0B2 | 128 | 108 | SD |
| 7 | 0.2 | 5 | 88 | T4N2aM0B2 | 9197 | 8636 | SD |

Overall, only grade 1 or 2 related adverse events (AEs) were reported. No patient enrolled in the trial experienced a DLT or any grade 3-5 related AEs. No IPH4102-related skin rashes or infections have been observed up to the dose-level tested.

Ex vivo functional assay results confirmed that SS patients' NK cells are functional and able to kill autologous tumor cells through ADCC.

Figure 3:
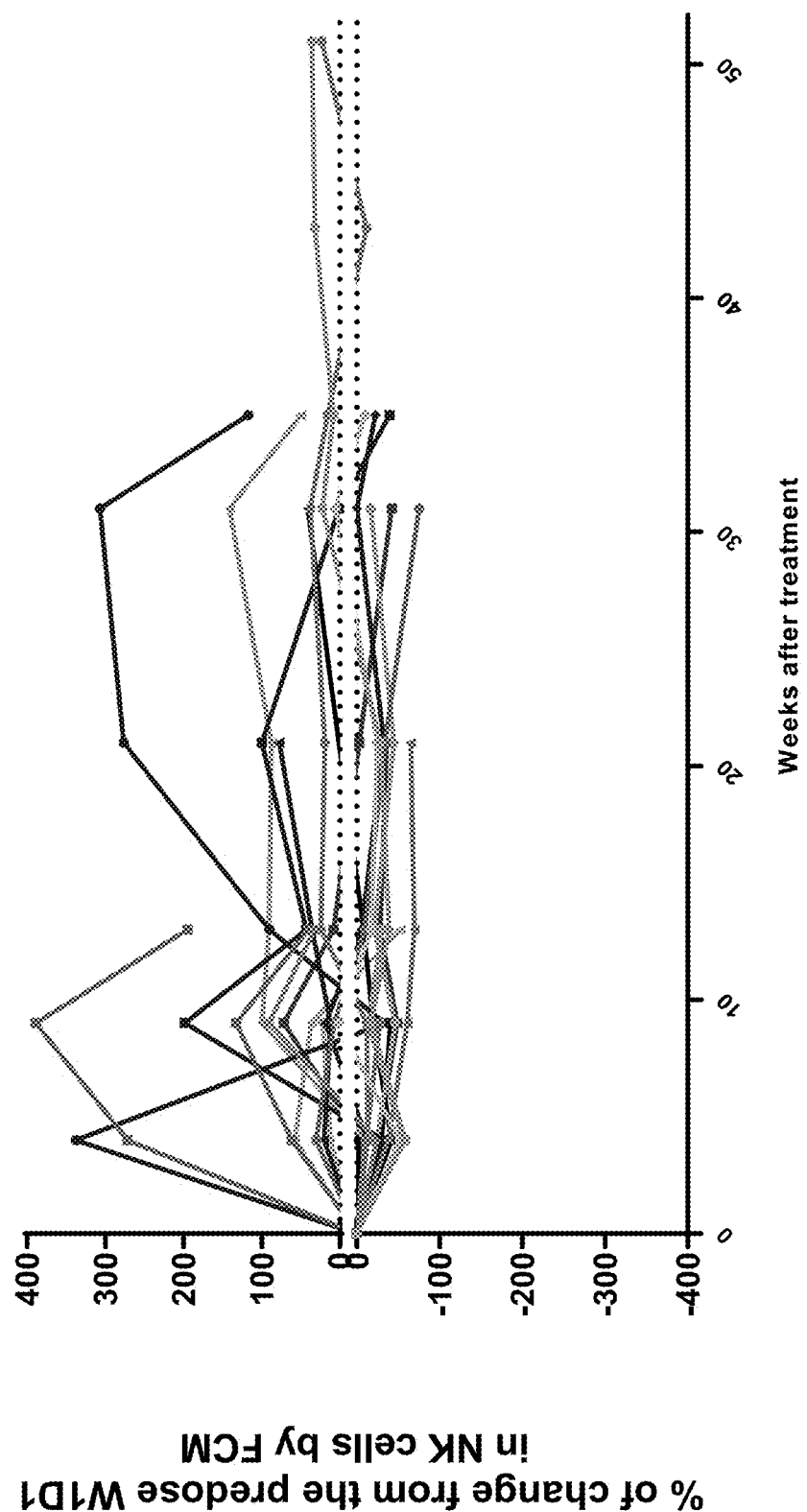
FIG. 3 shows that IPH4102 did not result in depletion of NK cells, as illustrated by the % change from baseline (day 1 of week 1) in patients' NK cells over a period of up to 50 weeks.
Figure 4:
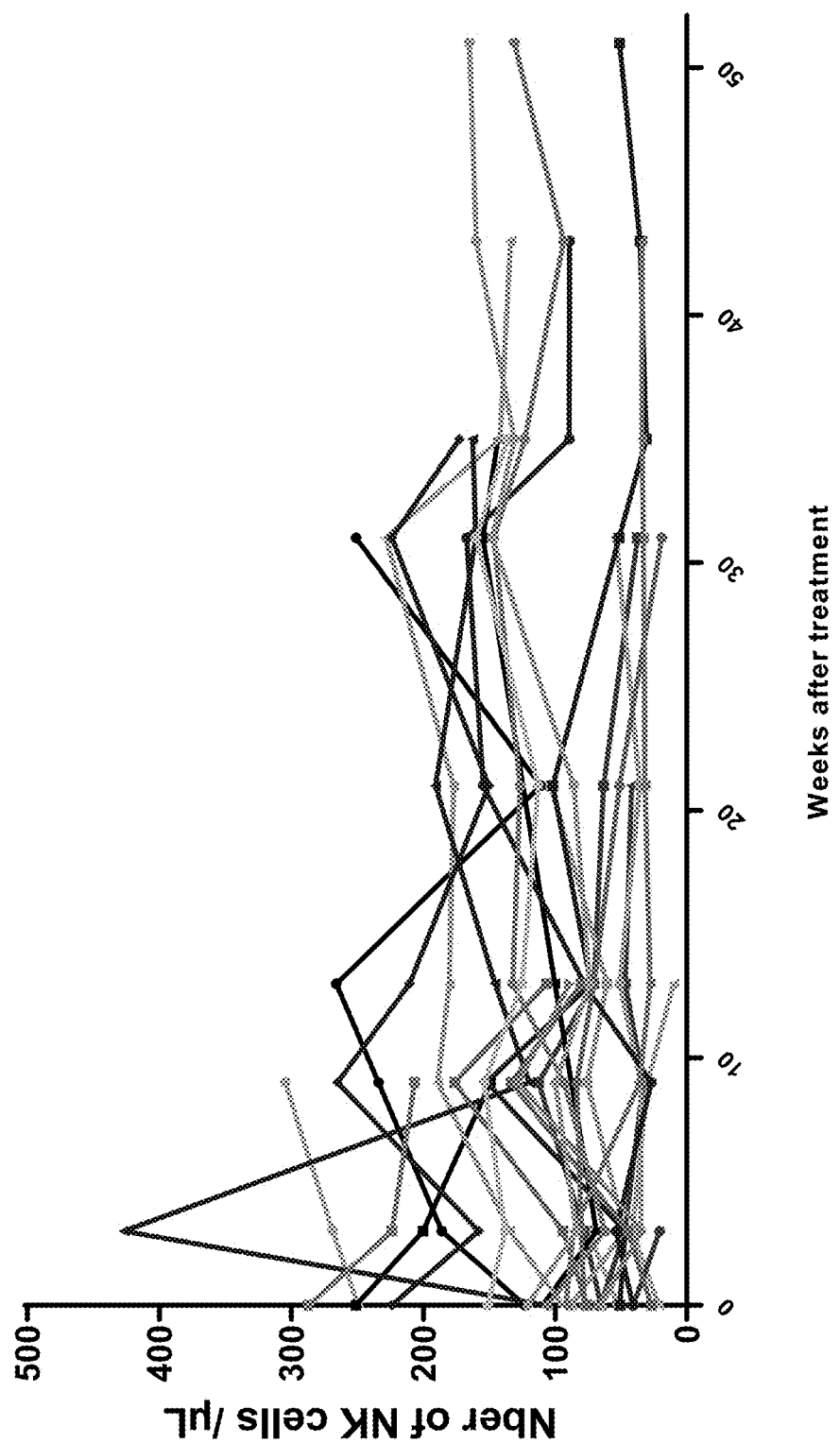
FIG. 4 shows that IPH4102 did not result in depletion of NK cells, as illustrated by the number of patients' NK cells (NK cells per μl) over a period of up to 50 weeks.

IPH4102 did not result in depletion of NK cells. FIG. 3 shows the % change from baseline (day 1 of week 1) in patients' NK cells over a period of up to 50 weeks. FIG. 4 shows the number of patients' NK cells (NK cells per µl) over a period of up to 50 weeks.

Preliminary IHC results were obtained in skin biopsies taken before and after IPH4102 repeated administrations. Signals of IPH4102 pharmacological activity in skin lesions were observed in patients, both with SS and MF, with evidence of marked decrease in KIR3DL2$^+$ cells in some cases. Representative examples include:

Patient 3 has MF and started the trial at the 0.01 mg/kg dose-level. He had 2 biopsies (B1 and B2) taken at screening with respectively 54% and 26% of KIR3DL2+ cells. At week 5, a decrease in KIR3DL2 staining was observed in B1 (0.5%) but not B2 (32%), and at W14, both lesions showed declined KIR3DL2+ cells (1% and 16% respectively). The patient is in global PR since week 10.

Patient 4 has Sézary Syndrome and started the trial at the 0.05 mg/kg dose-level, with 52% of KIR3DL2+ cells in the skin biopsy taken at screening. At week 5, a marked decrease in KIR3DL2 staining was observed, with only 4.4% of cells being KIR3DL2+. The patient is in global PR, with CR in blood, since week 10 in the study.

Patient 6 has SS and started the trial with 0.05 mg/kg. The screening biopsy presented 17.5% KIR3DL2+ cells that decreased to 3% at week 5. Also, histology of this lesion improved from plaque at screening to patch at week 5. However, this patient is still in global SD (with SD in skin and SD in blood).

Patient 7 has SS and started the trial with 0.2 mg/kg. The screening biopsy presented 76% KIR3DL2+ cells that remained stable at week 5 (62%). Histology of the lesion also improved from plaque to patch but this patient remains in global SD (SD in skin and in blood).

In conclusion, intermediate analysis of preliminary signs of clinical activity shows that IPH4102 is able to provide meaningful clinical benefit to advanced CTCL patients at repeated doses; patients with response received doses as low as 0.0001 mg/kg (response on blood involvement) or 0.01 mg/kg (skin disease response). Clinical responses in blood (in SS patients) were observed even in patients with very high blood involvement (such as patient 2, who had more than 19,000 blood Sézary cells/μL blood at study entry. Interestingly, anti-tumor effects were observed at considerable less than full NK lytic activity during the duration of treatment. Furthermore, at the 0.01 mg/kg dose level, IPH4102 is expected to reach at most a very small number of malignant cells in skin.

Also, interestingly, anti-tumor response (in skin) was observed in a patient (patient 3, 0.01 mg/kg) having no blood involvement. This suggests that IPH4102 will be useful for treatment of individuals having indolent or early stage CTCL without significant blood involvement.

Furthermore, the ability to treat skin disease by administering IPH4102 intravenously, moreover at low amounts and furthermore without depletion of NK cells (a significant portion of NK cells express KIR3DL2) whether at lower and higher doses, is advantageous, because a single administration regimen can be used for patients with or without blood involvement, and/or with different tumor burden. Despite a wide range of blood and skin tumor burden in CTCL patient, IPH4102 is promising for use even in high tumor burden at doses below that which would be needed to occupy KIR3DL2 on tumor cells in these high-burden patients, suggesting that high dose treatment need not be used in these patients in order to maintain saturation of KIR3DL2 on malignant cells (e.g. in skin), and additionally that a single non-NK depleting treatment regimen can be used independent of levels of blood or skin tumor burden (achieving full receptor occupancy in tissues is generally believed to require a blood concentration of antibody least 10-fold that required to achieve full occupancy in circulation). Final results from the trial confirmed the good safety profile and promising activity of IPH4102 in this elderly and heavily pre-treated patients population (n=25). At or above the 1.5 mg/kg dose level (1.5, 3, 6 and 10 mg/kg), saturation on blood tumor cells was achieved, whatever injection schedule and in all patients irrespective of their blood tumor burden. The objective response rate in the 20 patients with Sézary syndrome was 50%; the ORR4 (rate of response lasting for at least more than 4 months) was 40%, the disease control rate (DCR), 90%, the median duration of response (DOR), 9.9 months and the median progression free survival (PFS), 10.8 months, respectively. Data showed substantial improvement in pruritis in patients having a global clinical response but also in patients with stable disease.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

We claim:

1. A method of treating a T cell malignancy with tissue manifestation, the method comprising administering to an individual having a T cell malignancy an agent that binds a KIR3DL2 polypeptide and is capable of causing effector cell-mediated lysis of a KIR3DL2-expressing cell, for at least one administration cycle in which the agent is administered at least twice in an amount that maintains a concentration in blood of at least the $EC_{60}$ for NK lytic capacity, between two successive administrations of the agent, wherein the agent is an antibody that binds specifically to a KIR3DL2 polypeptide and is administered in an amount of 10 mg/kg body weight or as a fixed dose equivalent of 750 mg, and wherein the treatment regimen comprises:

an induction period in which said amount of the antibody is administered in a plurality of successive intravenous administrations at a frequency of one administration per week, and a treatment period in which said amount of the antibody is administered in a plurality of successive intravenous administrations at a frequency of one or two administrations per month, and wherein the agent is an antibody comprising: a heavy chain CDR 1, 2 and 3 (HCDR1, HCDR2, HCDR3) comprising SEQ ID NO: 2 (HCDR1), SEQ ID NO: 3 (HCDR2) and SEQ ID NO: 4 (HCDR3) respectively, and a light chain CDR 1, 2 and 3 (LCDR1, LCDR2, LCDR3) comprising SEQ ID NO: 5 (LCDR1), 6 (LCDR2) and 7 (LCDR3) respectively; or a heavy chain CDR 1, 2 and 3 (HCDR1, HCDR2, HCDR3) comprising SEQ ID NO: 18 (HCDR1), SEQ ID NO: 19 (HCDR2) and SEQ ID NO: 20 (HCDR3) respectively, and a light chain CDR 1, 2 and 3 (LCDR1, LCDR2, LCDR3) comprising SEQ ID NO: 21 (LCDR1), 22 (LCDR2) or 23 (LCDR3).

2. The method of claim 1, wherein the treatment is effective in both individuals having high blood tumor burden and in individuals having low blood tumor burden.

3. The method of claim 1, wherein the individual has not received bone marrow transplantation or hematopoietic stem cell transplantation.

4. The method of claim 1, wherein the agent is administered intravenously.

5. The method of claim 1, wherein the T cell malignancy with tissue manifestation is a CTCL.

6. The method of claim 5, wherein the CTCL is an indolent CTCL.

7. The method of claim 1, wherein the treatment or method is used for the treatment or prevention of T cell proliferative disease in individuals substantially lacking detectable KIR3DL2-expressing malignant cells in circulation.

8. The method of claim 1, wherein the treatment or method is used for the treatment of T cell proliferative disease in individuals having high blood tumor burden.

9. The method of claim 1, wherein the same administration regimen is used for the treatment or prevention of T cell proliferative disease in individuals having stage 2 or 3 Mycosis fungoides.

10. The method of claim 1, wherein the agent is an antibody that binds specifically to a KIR3DL2 polypeptide and comprises an Fc domain of human IgG isotype that binds to a human CD16 polypeptide.

11. The method of claim 1, wherein the agent is an antibody that binds specifically to a KIR3DL2 polypeptide and is capable of causing an increase of cell surface KIR3DL2 polypeptide available for binding by an anti-KIR3DL2 antibody.

12. The method of claim 1, wherein the agent is an antibody that binds specifically to a KIR3DL2 polypeptide, comprising an Fc region derived from a human IgG1 isotype, characterized by an $EC_{50}$ in a $^{51}$Cr-release assay for HuT78 tumor lysis by PBMC from healthy volunteers, that is (a) less than or within 1-log of the $EC_{50}$ of an antibody comprising a heavy chain variable region comprising SEQ ID NO: 31, a light chain variable region comprising SEQ ID NO: 25 or 26, and an Fc region of human IgG1 isotype, and/or (b) less than 100 ng/ml, optionally between 1 and 100 ng/ml.

13. The method of claim 1, wherein the agent is an antibody that binds specifically to a KIR3DL2 polypeptide is administered in an amount of 10 mg/kg body weight, and wherein the treatment regimen comprises:

an induction period (or cycle) in which said amount of the antibody is administered in a plurality of successive intravenous administrations at a frequency of one administration per week, and a treatment period in which said amount of the antibody is administered in a plurality of successive intravenous administrations at a frequency of two administrations per month.

14. The method of claim 1, wherein the agent is administered in an amount of 10 mg/kg body weight, and wherein the treatment regimen comprises:

an induction period (or cycle) in which said amount of the antibody is administered in a plurality of successive intravenous administrations at a frequency of one administration per week, and a treatment period in which said amount of the antibody is administered in a plurality of successive intravenous administrations at a frequency of one administration per month.

15. The method of claim 1, wherein the individual presents pathogenic cells that express KIR3DL2 in skin.

16. The method of claim 1, wherein the disease is a Sezary Syndrome, Mycosis fungoides or NK/T lymphoma.

17. The method of claim 1, characterized by the absence of a step of detecting KIR3DL2-expressing malignant cells in blood prior to treatment with the agent.

18. The method of claim 1, wherein the agent is an antibody selected from the group consisting of:

(a) an antibody comprising a heavy chain variable region comprising SEQ ID NO: 31; and a light chain variable region comprising SEQ ID NO: 25; and (b) an antibody comprising a heavy chain variable region comprising SEQ ID NO: 31; and a light chain variable region comprising SEQ ID NO: 26.

19. The method of claim 18, wherein the antibody is a full length antibody comprising a heavy chain variable region (VH) fused to a human gamma 1 constant region and a light chain variable region (VL) fused to a human kappa constant region.

* * * * *

SEQUENCE LISTING

```
<160> NUMBER OF SEQ ID NOS: 109

<210> SEQ ID NO 1
<211> LENGTH: 434
<212> TYPE: PRT
<213> ORGANISM: homo sapiens

<400> SEQUENCE: 1

Leu Met Gly Gly Gln Asp Lys Pro Phe Leu Ser Ala Arg Pro Ser Thr
1               5                   10                  15

Val Val Pro Arg Gly Gly His Val Ala Leu Gln Cys His Tyr Arg Arg
            20                  25                  30

Gly Phe Asn Asn Phe Met Leu Tyr Lys Glu Asp Arg Ser His Val Pro
        35                  40                  45

Ile Phe His Gly Arg Ile Phe Gln Glu Ser Phe Ile Met Gly Pro Val
    50                  55                  60

Thr Pro Ala His Ala Gly Thr Tyr Arg Cys Arg Gly Ser Arg Pro His
65                  70                  75                  80

Ser Leu Thr Gly Trp Ser Ala Pro Ser Asn Pro Leu Val Ile Met Val
```

```
                     85                  90                  95
Thr Gly Asn His Arg Lys Pro Ser Leu Leu Ala His Pro Gly Pro Leu
                100                 105                 110

Leu Lys Ser Gly Glu Thr Val Ile Leu Gln Cys Trp Ser Asp Val Met
            115                 120                 125

Phe Glu His Phe Phe Leu His Arg Asp Gly Ile Ser Glu Asp Pro Ser
        130                 135                 140

Arg Leu Val Gly Gln Ile His Asp Gly Val Ser Lys Ala Asn Phe Ser
145                 150                 155                 160

Ile Gly Pro Leu Met Pro Val Leu Ala Gly Thr Tyr Arg Cys Tyr Gly
                165                 170                 175

Ser Val Pro His Ser Pro Tyr Gln Leu Ser Ala Pro Ser Asp Pro Leu
                180                 185                 190

Asp Ile Val Ile Thr Gly Leu Tyr Glu Lys Pro Ser Leu Ser Ala Gln
                195                 200                 205

Pro Gly Pro Thr Val Gln Ala Gly Glu Asn Val Thr Leu Ser Cys Ser
                210                 215                 220

Ser Trp Ser Ser Tyr Asp Ile Tyr His Leu Ser Arg Glu Gly Glu Ala
225                 230                 235                 240

His Glu Arg Arg Leu Arg Ala Val Pro Lys Val Asn Arg Thr Phe Gln
                245                 250                 255

Ala Asp Phe Pro Leu Gly Pro Ala Thr His Gly Gly Thr Tyr Arg Cys
                260                 265                 270

Phe Gly Ser Phe Arg Ala Leu Pro Cys Val Trp Ser Asn Ser Ser Asp
                275                 280                 285

Pro Leu Leu Val Ser Val Thr Gly Asn Pro Ser Ser Ser Trp Pro Ser
                290                 295                 300

Pro Thr Glu Pro Ser Ser Lys Ser Gly Ile Cys Arg His Leu His Val
305                 310                 315                 320

Leu Ile Gly Thr Ser Val Val Ile Phe Leu Phe Ile Leu Leu Leu Phe
                325                 330                 335

Phe Leu Leu Tyr Arg Trp Cys Ser Asn Lys Lys Asn Ala Ala Val Met
                340                 345                 350

Asp Gln Glu Pro Ala Gly Asp Arg Thr Val Asn Arg Gln Asp Ser Asp
                355                 360                 365

Glu Gln Asp Pro Gln Glu Val Thr Tyr Ala Gln Leu Asp His Cys Val
                370                 375                 380

Phe Ile Gln Arg Lys Ile Ser Arg Pro Ser Gln Arg Pro Lys Thr Pro
385                 390                 395                 400

Leu Thr Asp Thr Ser Val Tyr Thr Glu Leu Pro Asn Ala Glu Pro Arg
                405                 410                 415

Ser Lys Val Val Ser Cys Pro Arg Ala Pro Gln Ser Gly Leu Glu Gly
                420                 425                 430

Val Phe

<210> SEQ ID NO 2
<211> LENGTH: 5
<212> TYPE: PRT
<213> ORGANISM: Mus musculus

<400> SEQUENCE: 2

Ser Tyr Thr Met His
1               5
```

```
<210> SEQ ID NO 3
<211> LENGTH: 15
<212> TYPE: PRT
<213> ORGANISM: Mus musculus

<400> SEQUENCE: 3

Tyr Ile Asn Pro Ser Ser Gly Tyr Thr Glu Asn Asn Arg Lys Phe
1               5                   10                  15

<210> SEQ ID NO 4
<211> LENGTH: 12
<212> TYPE: PRT
<213> ORGANISM: Mus musculus

<400> SEQUENCE: 4

Arg Leu Gly Lys Gly Leu Leu Pro Pro Phe Asp Tyr
1               5                   10

<210> SEQ ID NO 5
<211> LENGTH: 11
<212> TYPE: PRT
<213> ORGANISM: Mus musculus

<400> SEQUENCE: 5

Arg Ala Ser Glu Asn Ile Tyr Ser Asn Leu Ala
1               5                   10

<210> SEQ ID NO 6
<211> LENGTH: 7
<212> TYPE: PRT
<213> ORGANISM: Mus musculus

<400> SEQUENCE: 6

Ala Ala Thr Asn Leu Ala Asp
1               5

<210> SEQ ID NO 7
<211> LENGTH: 9
<212> TYPE: PRT
<213> ORGANISM: Mus musculus

<400> SEQUENCE: 7

Gln His Phe Trp Gly Thr Pro Tyr Thr
1               5

<210> SEQ ID NO 8
<211> LENGTH: 107
<212> TYPE: PRT
<213> ORGANISM: artificial
<220> FEATURE:
<223> OTHER INFORMATION: Chimeric

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Lys Leu Leu Leu
        35                  40                  45

Tyr Ala Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80
```

Glu Asp Phe Ala Thr Tyr Tyr Cys Gln His Phe Trp Gly Thr Pro Tyr
                85                  90                  95

Thr Phe Gly Gln Gly Thr Lys Leu Glu Ile Lys
            100                 105

<210> SEQ ID NO 9
<211> LENGTH: 107
<212> TYPE: PRT
<213> ORGANISM: artificial
<220> FEATURE:
<223> OTHER INFORMATION: Chimeric

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Gly Thr Pro Tyr
                85                  90                  95

Thr Phe Gly Gly Gly Thr Lys Leu Glu Ile Lys
            100                 105

<210> SEQ ID NO 10
<211> LENGTH: 107
<212> TYPE: PRT
<213> ORGANISM: artificial
<220> FEATURE:
<223> OTHER INFORMATION: chimeric

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Asn
            20                  25                  30

Leu Ala Trp Tyr Gln Gln Lys Pro Gly Lys Ala Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gly Tyr Thr Leu Thr Ile Ser Ser Leu Gln Pro
65                  70                  75                  80

Glu Asp Phe Ala Thr Tyr Tyr Cys Gln His Phe Trp Gly Thr Pro Tyr
                85                  90                  95

Thr Phe Gly Gly Gly Thr Lys Leu Glu Ile Lys
            100                 105

<210> SEQ ID NO 11
<211> LENGTH: 107
<212> TYPE: PRT
<213> ORGANISM: Artificial
<220> FEATURE:
<223> OTHER INFORMATION: Chimeric

<400> SEQUENCE: 11

Asp Ile Gln Met Thr Gln Ser Pro Ser Ser Leu Ser Ala Ser Val Gly

```
                1               5                   10                  15
            Asp Arg Val Thr Ile Thr Cys Arg Ala Ser Glu Asn Ile Tyr Ser Asn
                                20                  25                  30

Leu Ala Trp Tyr Gln Gln Lys Gln Gly Lys Ala Pro Gln Leu Leu Val
                    35                  40                  45

Tyr Ala Ala Thr Asn Leu Ala Asp Gly Val Pro Ser Arg Phe Ser Gly
                50                  55                  60

Ser Gly Ser Gly Thr Gln Tyr Thr Leu Thr Ile Asn Ser Leu Gln Pro
            65                  70                  75                  80

Glu Asp Phe Ala Thr Tyr Tyr Cys Gln His Phe Trp Gly Thr Pro Tyr
                            85                  90                  95

Thr Phe Gly Gly Gly Thr Lys Leu Glu Ile Lys
                            100                 105

<210> SEQ ID NO 12
<211> LENGTH: 107
<212> TYPE: PRT
<213> ORGANISM: artificial
<220> FEATURE:
<223> OTHER INFORMATION: chimeric

<400> SEQUENCE: 12

Asp Ile Gln Met Thr Gln Ser Pro Ser Ser Leu Ser Ala Ser Val Gly
            1               5                   10                  15

Glu Thr Val Thr Ile Thr Cys Arg Ala Ser Glu Asn Ile Tyr Ser Asn
                                20                  25                  30

Leu Ala Trp Tyr Gln Gln Lys Gln Gly Lys Ala Pro Gln Leu Leu Val
                            35                  40                  45

Tyr Ala Ala Thr Asn Leu Ala Asp Gly Val Pro Ser Arg Phe Ser Gly
                50                  55                  60

Ser Gly Ser Gly Thr Gln Tyr Thr Leu Thr Ile Asn Ser Leu Gln Pro
            65                  70                  75                  80

Glu Asp Phe Ala Thr Tyr Tyr Cys Gln His Phe Trp Gly Thr Pro Tyr
                            85                  90                  95

Thr Phe Gly Gly Gly Thr Lys Leu Glu Ile Lys
                            100                 105

<210> SEQ ID NO 13
<211> LENGTH: 120
<212> TYPE: PRT
<213> ORGANISM: artificial
<220> FEATURE:
<223> OTHER INFORMATION: chimeric

<400> SEQUENCE: 13

Gln Val Gln Leu Val Gln Ser Gly Ala Glu Val Lys Lys Pro Gly Ala
            1               5                   10                  15

Ser Val Lys Val Ser Cys Lys Ala Ser Gly Tyr Thr Phe Thr Ser Tyr
                                20                  25                  30

Thr Met His Trp Val Arg Gln Ala Pro Gly Gln Gly Leu Glu Trp Met
                            35                  40                  45

Gly Tyr Ile Asn Pro Ser Ser Gly Tyr Thr Glu Asn Asn Arg Lys Phe
                50                  55                  60

Lys Asp Arg Val Thr Met Thr Arg Asp Thr Ser Thr Ser Thr Val Tyr
            65                  70                  75                  80

Met Glu Leu Ser Ser Leu Arg Ser Glu Asp Thr Ala Val Tyr Tyr Cys
                            85                  90                  95
```

```
Ala Arg Leu Gly Lys Gly Leu Leu Pro Pro Phe Asp Tyr Trp Gly Gln
            100                 105                 110

Gly Thr Thr Val Thr Val Ser Ser
        115                 120

<210> SEQ ID NO 14
<211> LENGTH: 120
<212> TYPE: PRT
<213> ORGANISM: artificial
<220> FEATURE:
<223> OTHER INFORMATION: chimeric

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Ile
            35                  40                  45

Gly Tyr Ile Asn Pro Ser Ser Gly Tyr Thr Glu Asn Asn Arg Lys Phe
        50                  55                  60

Lys Asp Lys Thr Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly Lys Gly Leu Leu Pro Pro Phe Asp Tyr Trp Gly Gln
            100                 105                 110

Gly Thr Thr Val Thr Val Ser Ser
        115                 120

<210> SEQ ID NO 15
<211> LENGTH: 120
<212> TYPE: PRT
<213> ORGANISM: artificial
<220> FEATURE:
<223> OTHER INFORMATION: chimeric

<400> SEQUENCE: 15

Gln Val Gln Leu Gln Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Ile
            35                  40                  45

Gly Tyr Ile Asn Pro Ser Ser Gly Tyr Thr Glu Asn Asn Arg Lys Phe
        50                  55                  60

Lys Asp Lys Thr Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly Lys Gly Leu Leu Pro Pro Phe Asp Tyr Trp Gly Gln
            100                 105                 110

Gly Thr Thr Leu Thr Val Ser Ser
        115                 120

<210> SEQ ID NO 16
<211> LENGTH: 120
<212> TYPE: PRT
<213> ORGANISM: artificial
```

```
<220> FEATURE:
<223> OTHER INFORMATION: chimeric

<400> SEQUENCE: 16

Gln Val Gln Leu Val Gln Ser Gly Ala Glu Leu Ala Arg Pro Gly Ala
1               5                   10                  15

Ser Val Lys Val Ser Cys Lys Ala Ser Gly Tyr Thr Phe Thr Ser Tyr
            20                  25                  30

Thr Met His Trp Val Arg Gln Ala Pro Gly Gln Gly Leu Glu Trp Ile
        35                  40                  45

Gly Tyr Ile Asn Pro Ser Ser Gly Tyr Thr Glu Asn Asn Arg Lys Phe
    50                  55                  60

Lys Asp Lys Thr Thr Leu Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly Lys Gly Leu Leu Pro Pro Phe Asp Tyr Trp Gly Gln
            100                 105                 110

Gly Thr Thr Val Thr Val Ser Ser
        115                 120

<210> SEQ ID NO 17
<211> LENGTH: 120
<212> TYPE: PRT
<213> ORGANISM: artificial
<220> FEATURE:
<223> OTHER INFORMATION: chimeric

<400> SEQUENCE: 17

Gln Val Gln Leu Gln Gln Ser Gly Ala Glu Val Lys Lys Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Glu Asn Asn Arg Lys Phe
    50                  55                  60

Lys Asp Lys Thr Thr Leu Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Gly Lys Gly Leu Leu Pro Pro Phe Asp Tyr Trp Gly Gln
            100                 105                 110

Gly Thr Thr Leu Thr Val Ser Ser
        115                 120

<210> SEQ ID NO 18
<211> LENGTH: 5
<212> TYPE: PRT
<213> ORGANISM: Mus musculus

<400> SEQUENCE: 18

Thr Ala Gly Met Gln
1               5

<210> SEQ ID NO 19
<211> LENGTH: 16
<212> TYPE: PRT
<213> ORGANISM: Mus musculus
```

```
<400> SEQUENCE: 19

Trp Ile Asn Ser His Ser Gly Val Pro Lys Tyr Ala Glu Asp Phe Lys
1               5                   10                  15

<210> SEQ ID NO 20
<211> LENGTH: 9
<212> TYPE: PRT
<213> ORGANISM: Mus musculus

<400> SEQUENCE: 20

Gly Gly Asp Glu Gly Val Met Asp Tyr
1               5

<210> SEQ ID NO 21
<211> LENGTH: 11
<212> TYPE: PRT
<213> ORGANISM: Mus musculus

<400> SEQUENCE: 21

Lys Ala Ser Gln Asp Val Ser Thr Ala Val Ala
1               5                   10

<210> SEQ ID NO 22
<211> LENGTH: 7
<212> TYPE: PRT
<213> ORGANISM: Mus musculus

<400> SEQUENCE: 22

Trp Thr Ser Thr Arg His Thr
1               5

<210> SEQ ID NO 23
<211> LENGTH: 9
<212> TYPE: PRT
<213> ORGANISM: Mus musculus

<400> SEQUENCE: 23

Gln Gln His Tyr Ser Thr Pro Trp Thr
1               5

<210> SEQ ID NO 24
<211> LENGTH: 107
<212> TYPE: PRT
<213> ORGANISM: Artificial
<220> FEATURE:
<223> OTHER INFORMATION: chimeric

<400> SEQUENCE: 24

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Trp Thr Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His Tyr Ser Thr Pro Trp
                85                  90                  95

Thr Phe Gly Gly Gly Thr Lys Val Glu Ile Lys
```

<210> SEQ ID NO 25
<211> LENGTH: 107
<212> TYPE: PRT
<213> ORGANISM: Artificial
<220> FEATURE:
<223> OTHER INFORMATION: chimeric

<400> SEQUENCE: 25

Asp Ile Gln Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Trp Thr Ser Thr Arg His Thr Gly Val Pro Asp Arg Phe Ser Gly
    50                  55                  60

Ser Gly Ser Gly Thr Asp Tyr Thr Leu Thr Ile Ser Ser Leu Gln Ala
65                  70                  75                  80

Glu Asp Val Ala Val Tyr Tyr Cys Gln Gln His Tyr Ser Thr Pro Trp
                85                  90                  95

Thr Phe Gly Gly Gly Thr Lys Val Glu Ile Lys
            100                 105

<210> SEQ ID NO 26
<211> LENGTH: 107
<212> TYPE: PRT
<213> ORGANISM: Artificial
<220> FEATURE:
<223> OTHER INFORMATION: chimeric

<400> SEQUENCE: 26

Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Trp Thr Ser Thr Arg His Thr Gly Val Pro Asp Arg Phe Ser Gly
    50                  55                  60

Ser Gly Ser Gly Thr Asp Tyr Thr Leu Thr Ile Ser Ser Val Gln Ala
65                  70                  75                  80

Glu Asp Val Ala Val Tyr Tyr Cys Gln Gln His Tyr Ser Thr Pro Trp
                85                  90                  95

Thr Phe Gly Gly Gly Thr Lys Val Glu Ile Lys
            100                 105

<210> SEQ ID NO 27
<211> LENGTH: 107
<212> TYPE: PRT
<213> ORGANISM: Artificial
<220> FEATURE:
<223> OTHER INFORMATION: chimeric

<400> SEQUENCE: 27

Asp Ile Val Met Thr Gln Ser Pro Ser Phe Leu Ser Ala Ser Val Gly
1               5                   10                  15

Asp Arg Val Thr Phe Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
            35                  40                  45

Tyr Trp Thr Ser Thr Arg His Thr Gly Val Pro Asp Arg Phe Ser Gly
    50                  55                  60

Ser Gly Ser Gly Thr Asp Tyr Thr Leu Thr Ile Ser Ser Val Gln Ala
65                  70                  75                  80

Glu Asp Val Ala Val Tyr Tyr Cys Gln Gln His Tyr Ser Thr Pro Trp
                85                  90                  95

Thr Phe Gly Gly Gly Thr Lys Val Glu Ile Lys
            100                 105

<210> SEQ ID NO 28
<211> LENGTH: 107
<212> TYPE: PRT
<213> ORGANISM: Artificial
<220> FEATURE:
<223> OTHER INFORMATION: Chimeric

<400> SEQUENCE: 28

Asp Ile Val Met Thr Gln Ser His Lys Phe Leu Ser Ala Ser Val Gly
1               5                   10                  15

Asp Arg Val Thr Phe Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
            35                  40                  45

Tyr Trp Thr Ser Thr Arg His Thr Gly Val Pro Asp Arg Phe Ser Gly
    50                  55                  60

Ser Gly Ser Gly Thr Asp Tyr Thr Leu Thr Ile Ser Ser Val Gln Ala
65                  70                  75                  80

Glu Asp Val Ala Val Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 29
<211> LENGTH: 118
<212> TYPE: PRT
<213> ORGANISM: Artificial
<220> FEATURE:
<223> OTHER INFORMATION: Chimeric

<400> SEQUENCE: 29

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Ala
            20                  25                  30

Gly Met Gln Trp Val Arg Gln Ala Pro Gly Gln Gly Leu Glu Trp Met
            35                  40                  45

Gly Trp Ile Asn Ser His Ser Gly Val Pro Lys Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Gly Gly Asp Glu Gly Val Met Asp Tyr Trp Gly Gln Gly Thr
            100                 105                 110

Thr Val Thr Val Ser Ser

<210> SEQ ID NO 30
<211> LENGTH: 118
<212> TYPE: PRT
<213> ORGANISM: Artificial
<220> FEATURE:
<223> OTHER INFORMATION: chimeric

<400> SEQUENCE: 30

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Ala
            20                  25                  30

Gly Met Gln Trp Val Gln Lys Ser Pro Gly Gln Gly Leu Glu Trp Met
        35                  40                  45

Gly Trp Ile Asn Ser His Ser Gly Val Pro Lys Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Gly Gly Asp Glu Gly Val Met Asp Tyr Trp Gly Gln Gly Thr
            100                 105                 110

Thr Val Thr Val Ser Ser
        115

<210> SEQ ID NO 31
<211> LENGTH: 118
<212> TYPE: PRT
<213> ORGANISM: Artificial
<220> FEATURE:
<223> OTHER INFORMATION: chimeric

<400> SEQUENCE: 31

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Ala
            20                  25                  30

Gly Met Gln Trp Val Arg Gln Ala Pro Gly Gln Gly Leu Glu Trp Ile
        35                  40                  45

Gly Trp Ile Asn Ser His Ser Gly Val Pro Lys Tyr Ala Glu Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Gly Gly Asp Glu Gly Val Met Asp Tyr Trp Gly Gln Gly Thr
            100                 105                 110

Thr Val Thr Val Ser Ser
        115

<210> SEQ ID NO 32
<211> LENGTH: 118
<212> TYPE: PRT
<213> ORGANISM: Artificial
<220> FEATURE:
<223> OTHER INFORMATION: Chimeric

<400> SEQUENCE: 32

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Ala
            20                  25                  30

Gly Met Gln Trp Val Gln Lys Ser Pro Gly Gln Gly Leu Glu Trp Ile
        35                  40                  45

Gly Trp Ile Asn Ser His Ser Gly Val Pro Lys Tyr Ala Glu Asp Phe
50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Gly Gly Asp Glu Gly Val Met Asp Tyr Trp Gly Gln Gly Thr
            100                 105                 110

Thr Val Thr Val Ser Ser
            115

<210> SEQ ID NO 33
<211> LENGTH: 118
<212> TYPE: PRT
<213> ORGANISM: Artificial
<220> FEATURE:
<223> OTHER INFORMATION: Chimeric

<400> SEQUENCE: 33

Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Thr Ala
            20                  25                  30

Gly Met Gln Trp Val Gln Lys Thr Pro Gly Lys Gly Leu Glu Trp Ile
        35                  40                  45

Gly Trp Ile Asn Ser His Ser Gly Val Pro Lys Tyr Ala Glu Asp Phe
50                  55                  60

Lys Gly Arg Phe Ala Phe Ser Leu Asp Thr Ser Ala Ser Thr Ala Tyr
65                  70                  75                  80

Leu Gln Ile Ser Ser Leu Lys Ala Glu Asp Thr Ala Val Tyr Phe Cys
                85                  90                  95

Ala Arg Gly Gly Asp Glu Gly Val Met Asp Tyr Trp Gly Gln Gly Thr
            100                 105                 110

Ser Val Thr Val Ser Ser
            115

<210> SEQ ID NO 34
<211> LENGTH: 117
<212> TYPE: PRT
<213> ORGANISM: Mus musculus

<400> SEQUENCE: 34

Gln Ile Gln Leu Val Gln Ser Gly Pro Glu Leu Lys Lys Pro Gly Glu
1               5                   10                  15

Thr Val Arg Ile Ser Cys Lys Ala Ser Gly Tyr Thr Phe Thr Ile Ala
            20                  25                  30

Gly Met Gln Trp Val Gln Lys Met Pro Gly Lys Gly Leu Lys Trp Ile
        35                  40                  45

Gly Trp Ile Asn Thr His Ser Gly Val Pro Lys Tyr Ala Glu Asp Phe
50                  55                  60

```
Lys Gly Arg Phe Ala Phe Ser Leu Glu Thr Ser Ala Asn Ile Ala Tyr
 65                  70                  75                  80

Leu Gln Ile Ser Asn Leu Lys Asn Glu Asp Thr Ala Thr Tyr Phe Cys
                 85                  90                  95

Ala Arg Gly Gly Asp Glu Gly Val Met Asp Tyr Trp Gly Gln Gly Thr
            100                 105                 110

Ser Val Thr Val Ser
            115

<210> SEQ ID NO 35
<211> LENGTH: 107
<212> TYPE: PRT
<213> ORGANISM: Mus musculus

<400> SEQUENCE: 35

Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Ser Thr Ala
             20                  25                  30

Val Ala Trp Tyr His Gln Lys Pro Gly Gln Ser Pro Lys Leu Leu Ile
         35                  40                  45

Tyr Trp Ala Ser Thr Arg His Thr Gly Val Pro Asp Arg Phe Ser Gly
 50                  55                  60

Ser Gly Ser Gly Thr Asp Tyr Thr Leu Thr Ile Ser Ala Leu Gln Ala
 65                  70                  75                  80

Glu Asp Leu Ala Leu Tyr Tyr Cys Gln Gln His Tyr Asn Thr Pro Trp
                 85                  90                  95

Thr Phe Gly Gly Gly Thr Lys Leu Glu Ile Lys
            100                 105

<210> SEQ ID NO 36
<211> LENGTH: 117
<212> TYPE: PRT
<213> ORGANISM: Mus musculus

<400> SEQUENCE: 36

Gln Ile Gln Leu Val Gln Ser Gly Pro Glu Leu Lys Lys Pro Gly Glu
 1               5                  10                  15

Thr Val Arg Ile Ser Cys Lys Ala Ser Gly Tyr Thr Phe Thr Thr Ala
             20                  25                  30

Gly Met Gln Trp Val Gln Lys Thr Pro Gly Lys Gly Leu Lys Trp Ile
         35                  40                  45

Gly Trp Ile Asn Ser His Ser Gly Val Pro Lys Tyr Ala Glu Asp Phe
 50                  55                  60

Lys Gly Arg Phe Ala Phe Ser Leu Glu Thr Ser Ala Ser Thr Ala Tyr
 65                  70                  75                  80

Leu Gln Ile Ser Thr Leu Lys Asn Glu Asp Thr Ala Thr Tyr Phe Cys
                 85                  90                  95

Ala Arg Gly Gly Asp Glu Gly Val Met Asp Tyr Trp Gly Gln Gly Thr
            100                 105                 110

Ser Val Thr Val Ser
            115

<210> SEQ ID NO 37
<211> LENGTH: 107
<212> TYPE: PRT
<213> ORGANISM: mus musculus
```

<400> SEQUENCE: 37

Asp Ile Val Met Thr Gln Ser His Lys Phe Met Ser Thr Ser Leu Gly
1               5                   10                  15

Asp Arg Val Ser Phe Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Trp Thr Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Ser Thr Pro Trp
                85                  90                  95

Thr Phe Gly Gly Gly Thr Lys Leu Glu Ile Lys
            100                 105

<210> SEQ ID NO 38
<211> LENGTH: 139
<212> TYPE: PRT
<213> ORGANISM: Mus musculus

<400> SEQUENCE: 38

Gln Val Gln Leu Gln Gln Ser Ala Ala Glu Leu Ala Arg Pro Gly Ala
1               5                   10                  15

Ser Val Lys Met Ser Cys Lys Ala Ser Gly Tyr Thr Phe Thr Ser Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Glu Asn Asn Arg Lys Phe
    50                  55                  60

Lys Asp Lys Thr Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Leu Gly Lys Gly Leu Leu Pro Pro Phe Asp Tyr Trp Gly Gln
            100                 105                 110

Gly Thr Thr Leu Thr Val Ser Ser Ala Lys Thr Thr Pro Pro Ser Val
        115                 120                 125

Tyr Pro Leu Ala Pro Gly Ser Ala Ala Gln Thr
    130                 135

<210> SEQ ID NO 39
<211> LENGTH: 107
<212> TYPE: PRT
<213> ORGANISM: Mus musculus

<400> SEQUENCE: 39

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser

```
                65                  70                  75                  80
Glu Asp Phe Gly Ser Tyr Tyr Cys Gln His Phe Trp Gly Thr Pro Tyr
                    85                  90                  95

Thr Phe Gly Gly Gly Thr Lys Leu Glu Ile Lys
                100                 105
```

<210> SEQ ID NO 40
<211> LENGTH: 119
<212> TYPE: PRT
<213> ORGANISM: Mus musculus

<400> SEQUENCE: 40

```
Glu Val Gln Leu Gln Gln Ser Gly Pro Glu Leu Val Lys Pro Gly Ala
1               5                   10                  15

Ser Met Lys Ile Ser Cys Lys Ala Ser His Tyr Ser Phe Ile Gly Tyr
                20                  25                  30

Thr Met Asn Trp Val Lys Gln Arg His Gly Lys Asn Leu Glu Trp Ile
            35                  40                  45

Gly Leu Ile Asn Pro Tyr Asn Gly Asp Thr Thr Tyr Asn Gln Lys Phe
        50                  55                  60

Lys Gly Lys Ala Ser Leu Thr Val Asp Lys Ser Ser Ser Thr Ala Tyr
65                  70                  75                  80

Met Glu Ile Leu Ser Leu Thr Ser Glu Asp Ser Ala Val Tyr Tyr Cys
                85                  90                  95

Ala Arg Glu Asn Trp Gly Tyr Pro Tyr Ala Met Asp Tyr Trp Gly Gln
                100                 105                 110

Gly Thr Ser Val Thr Val Ser
        115
```

<210> SEQ ID NO 41
<211> LENGTH: 111
<212> TYPE: PRT
<213> ORGANISM: Mus musculus

<400> SEQUENCE: 41

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Phe
                20                  25                  30

Gly Ile Ser Phe Met Asn Trp Phe Gln Gln Lys Pro Gly Gln Pro Pro
            35                  40                  45

Lys Leu Leu Ile Tyr Ala Ala Ser Asn Gln Gly Ser Gly Val Pro Ala
        50                  55                  60

Arg Phe Ser Gly Ser Arg Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Tyr Thr Phe Gly Gly Gly Thr Lys Leu Glu Ile Lys
                100                 105                 110
```

<210> SEQ ID NO 42
<211> LENGTH: 117
<212> TYPE: PRT
<213> ORGANISM: Mus musculus

<400> SEQUENCE: 42

```
Gln Val Gln Leu Gln Gln Ser Gly Ala Glu Leu Val Arg Pro Gly Val
1               5                   10                  15
```

```
Ser Val Lys Ile Ser Cys Lys Gly Ser Gly Tyr Thr Phe Thr Asp Tyr
                20                  25                  30

Ala Met Asn Trp Val Lys Gln Ser His Ala Lys Ser Leu Glu Trp Ile
            35                  40                  45

Gly Val Ile Ser Thr Tyr Gly Asp Ala Asn Tyr Asn Gln Lys Phe
50                      55                  60

Lys Gly Lys Ala Thr Met Thr Val Asp Lys Ser Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Leu Ile Tyr Tyr Asp Tyr Asp Gly Ser Tyr Trp Gly Gln Gly Thr
                100                 105                 110

Thr Leu Thr Val Ser
            115

<210> SEQ ID NO 43
<211> LENGTH: 113
<212> TYPE: PRT
<213> ORGANISM: Mus musculus

<400> SEQUENCE: 43

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Tyr Thr Phe Gly Gly Gly Thr Lys Leu Glu Ile
                100                 105                 110

Lys

<210> SEQ ID NO 44
<211> LENGTH: 120
<212> TYPE: PRT
<213> ORGANISM: Mus musculus

<400> SEQUENCE: 44

Gln Val Gln Leu Gln Gln Ser Ala Ala Glu Leu Ala Arg Pro Gly Ala
1               5                   10                  15

Ser Val Lys Met Ser Cys Lys Ala Ser Gly Tyr Thr Phe Thr Ser Tyr
                20                  25                  30

Thr Met His Trp Val Lys Gln Arg Pro Gly Gln Gly Leu Glu Trp Ile
            35                  40                  45

Gly Tyr Ile Asn Pro Ser Ser Gly Tyr Thr Asp Tyr Asn Gln Lys Phe
        50                  55                  60

Lys Asp Lys Thr Thr Leu Thr Ala Asp Arg Ser Ser Ser Thr Ala Tyr
65                  70                  75                  80

Met Gln Leu Ser Ser Leu Thr Ser Glu Asp Ser Ala Val Tyr Tyr Cys
                85                  90                  95
```

```
Ala Arg Leu Gly Lys Gly Leu Leu Pro Pro Phe Asp Tyr Trp Gly Gln
            100                 105                 110

Gly Ser Thr Leu Thr Val Ser Ser
        115                 120

<210> SEQ ID NO 45
<211> LENGTH: 113
<212> TYPE: PRT
<213> ORGANISM: Mus musculus

<400> SEQUENCE: 45

Glu Ile Val Leu Thr Gln Ser Ile Pro Ser Leu Thr Val Ser Ala Gly
1               5                   10                  15

Glu Arg Val Thr Ile Ser Cys Lys Ser Asn Gln Asn Leu Leu Trp Ser
            20                  25                  30

Gly Asn Gln Arg Tyr Cys Leu Val Trp His Gln Trp Lys Pro Gly Gln
        35                  40                  45

Thr Pro Thr Pro Leu Ile Thr Trp Thr Ser Asp Arg Tyr Ser Gly Val
    50                  55                  60

Pro Asp Arg Phe Ile Gly Ser Gly Ser Val Thr Asp Phe Thr Leu Thr
65                  70                  75                  80

Ile Ser Ser Val Gln Ala Glu Asp Val Ala Val Tyr Phe Cys Gln Gln
                85                  90                  95

His Leu His Ile Pro Tyr Thr Phe Gly Gly Gly Thr Lys Leu Glu Ile
            100                 105                 110

Lys

<210> SEQ ID NO 46
<211> LENGTH: 107
<212> TYPE: PRT
<213> ORGANISM: Mus musculus

<400> SEQUENCE: 46

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Tyr
                85                  90                  95

Thr Phe Gly Gly Gly Thr Lys Leu Glu Ile Lys
            100                 105

<210> SEQ ID NO 47
<211> LENGTH: 118
<212> TYPE: PRT
<213> ORGANISM: Mus musculus

<400> SEQUENCE: 47

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30
```

Trp Met Gln Trp Val Lys Gln Arg Pro Gly Gln Gly Leu Glu Trp Ile
            35                  40                  45

Gly Ala Ile Tyr Pro Gly Asp Gly Asp Thr Arg Tyr Thr Gln Lys Phe
        50                  55                  60

Lys Gly Lys Ala Thr Leu Thr Ala Asp Lys Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Arg Tyr Asp Gly Tyr Tyr His Phe Asp Tyr Trp Gly Gln Gly
                    100                 105                 110

Thr Thr Leu Thr Val Ser
            115

<210> SEQ ID NO 48
<211> LENGTH: 115
<212> TYPE: PRT
<213> ORGANISM: Mus musculus

<400> SEQUENCE: 48

Asp Ile Val Met Thr Gln Ser Pro Ser Ser Leu Ala Val Thr Ala Gly
1               5                   10                  15

Glu Lys Val Thr Met Ser Cys Lys Ser Ser Gln Ser Leu Leu Trp Ser
                20                  25                  30

Val Asn Gln Lys Asn Tyr Leu Ser Trp Tyr Gln Gln Lys Gln Arg Gln
            35                  40                  45

Pro Pro Lys Leu Leu Ile Tyr Gly Ala Ser Ile Arg Glu Ser Trp Val
        50                  55                  60

Pro Asp Arg Phe Thr Gly Ser Gly Ser Gly Thr Asp Phe Thr Leu Thr
65                  70                  75                  80

Ile Ser Asn Val His Ala Glu Asp Leu Ala Val Tyr Tyr Cys Gln His
                85                  90                  95

Asn His Gly Ser Phe Leu Pro Leu Thr Phe Gly Ser Gly Thr Lys Leu
                100                 105                 110

Glu Ile Lys
        115

<210> SEQ ID NO 49
<211> LENGTH: 120
<212> TYPE: PRT
<213> ORGANISM: Mus musculus

<400> SEQUENCE: 49

Gln Val Gln Leu Gln Gln Ser Gly Ala Glu Val Ala Arg Pro Gly Ala
1               5                   10                  15

Ser Val Lys Leu Ser Cys Lys Ser Ser Gly Phe Thr Phe Thr Thr Tyr
                20                  25                  30

Trp Met Gln Trp Val Lys Gln Arg Pro Gly Gln Gly Leu Glu Trp Ile
            35                  40                  45

Gly Ala Ile Tyr Pro Gly Asp Gly Asp Thr Arg Tyr Thr Gln Lys Phe
        50                  55                  60

Lys Gly Lys Ala Thr Leu Thr Asp Lys Ser Ser Ile Thr Ala Tyr
65                  70                  75                  80

Met Gln Leu Ser Ser Leu Ala Ser Glu Asp Ser Ala Val Tyr Tyr Cys
                85                  90                  95

Ala Arg Arg Gly Asp Tyr Gly Asn Tyr Gly Met Asp Tyr Trp Gly Gln
                    100                 105                 110

```
Gly Thr Ser Val Thr Val Ser Ser
        115                 120

<210> SEQ ID NO 50
<211> LENGTH: 112
<212> TYPE: PRT
<213> ORGANISM: Mus musculus

<400> SEQUENCE: 50

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn His Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 51
<211> LENGTH: 5
<212> TYPE: PRT
<213> ORGANISM: Mus musculus

<400> SEQUENCE: 51

Ile Ala Gly Met Gln
1               5

<210> SEQ ID NO 52
<211> LENGTH: 6
<212> TYPE: PRT
<213> ORGANISM: Mus musculus

<400> SEQUENCE: 52

Gly Tyr Thr Phe Thr Ile
1               5

<210> SEQ ID NO 53
<211> LENGTH: 10
<212> TYPE: PRT
<213> ORGANISM: Mus musculus

<400> SEQUENCE: 53

Gly Tyr Thr Phe Thr Ile Ala Gly Met Gln
1               5                   10

<210> SEQ ID NO 54
<211> LENGTH: 17
<212> TYPE: PRT
<213> ORGANISM: Mus musculus

<400> SEQUENCE: 54

Trp Ile Asn Thr His Ser Gly Val Pro Lys Tyr Ala Glu Asp Phe Lys
1               5                   10                  15

Gly
```

<210> SEQ ID NO 55
<211> LENGTH: 10
<212> TYPE: PRT
<213> ORGANISM: Mus musculus

<400> SEQUENCE: 55

Trp Ile Asn Thr His Ser Gly Val Pro Lys
1               5                   10

<210> SEQ ID NO 56
<211> LENGTH: 6
<212> TYPE: PRT
<213> ORGANISM: Mus musculus

<400> SEQUENCE: 56

Gly Tyr Thr Phe Thr Thr
1               5

<210> SEQ ID NO 57
<211> LENGTH: 10
<212> TYPE: PRT
<213> ORGANISM: Mus musculus

<400> SEQUENCE: 57

Gly Tyr Thr Phe Thr Thr Ala Gly Met Gln
1               5                   10

<210> SEQ ID NO 58
<211> LENGTH: 9
<212> TYPE: PRT
<213> ORGANISM: Mus musculus

<400> SEQUENCE: 58

Trp Ile Asn Ser His Ser Gly Val Pro
1               5

<210> SEQ ID NO 59
<211> LENGTH: 10
<212> TYPE: PRT
<213> ORGANISM: Mus musculus

<400> SEQUENCE: 59

Gly Gly Asp Glu Gly Val Met Asp Tyr Trp
1               5                   10

<210> SEQ ID NO 60
<211> LENGTH: 6
<212> TYPE: PRT
<213> ORGANISM: Mus musculus

<400> SEQUENCE: 60

Gly Tyr Thr Phe Thr Ser
1               5

<210> SEQ ID NO 61
<211> LENGTH: 10
<212> TYPE: PRT
<213> ORGANISM: Mus musculus

<400> SEQUENCE: 61

Gly Tyr Thr Phe Thr Ser Tyr Thr Met His
1               5                   10

<210> SEQ ID NO 62

```
<211> LENGTH: 8
<212> TYPE: PRT
<213> ORGANISM: Mus musculus

<400> SEQUENCE: 62

Tyr Ile Asn Pro Ser Ser Gly Tyr
1               5

<210> SEQ ID NO 63
<211> LENGTH: 12
<212> TYPE: PRT
<213> ORGANISM: Mus musculus

<400> SEQUENCE: 63

Arg Leu Gly Lys Gly Leu Leu Pro Pro Phe Asp Tyr
1               5                   10

<210> SEQ ID NO 64
<211> LENGTH: 5
<212> TYPE: PRT
<213> ORGANISM: Mus musculus

<400> SEQUENCE: 64

Gly Tyr Thr Met Asn
1               5

<210> SEQ ID NO 65
<211> LENGTH: 6
<212> TYPE: PRT
<213> ORGANISM: Mus musculus

<400> SEQUENCE: 65

His Tyr Ser Phe Ile Gly
1               5

<210> SEQ ID NO 66
<211> LENGTH: 10
<212> TYPE: PRT
<213> ORGANISM: Mus musculus

<400> SEQUENCE: 66

His Tyr Ser Phe Ile Gly Tyr Thr Met Asn
1               5                   10

<210> SEQ ID NO 67
<211> LENGTH: 17
<212> TYPE: PRT
<213> ORGANISM: Mus musculus

<400> SEQUENCE: 67

Leu Ile Asn Pro Tyr Asn Gly Asp Thr Thr Tyr Asn Gln Lys Phe Lys
1               5                   10                  15

Gly

<210> SEQ ID NO 68
<211> LENGTH: 10
<212> TYPE: PRT
<213> ORGANISM: Mus musculus

<400> SEQUENCE: 68

Leu Ile Asn Pro Tyr Asn Gly Asp Thr Thr
1               5                   10

<210> SEQ ID NO 69
```

```
<211> LENGTH: 11
<212> TYPE: PRT
<213> ORGANISM: Mus musculus

<400> SEQUENCE: 69

Glu Asn Trp Gly Tyr Pro Tyr Ala Met Asp Tyr
1               5                   10

<210> SEQ ID NO 70
<211> LENGTH: 5
<212> TYPE: PRT
<213> ORGANISM: Mus musculus

<400> SEQUENCE: 70

Asp Tyr Ala Met Asn
1               5

<210> SEQ ID NO 71
<211> LENGTH: 6
<212> TYPE: PRT
<213> ORGANISM: Mus musculus

<400> SEQUENCE: 71

Gly Tyr Thr Phe Thr Asp
1               5

<210> SEQ ID NO 72
<211> LENGTH: 10
<212> TYPE: PRT
<213> ORGANISM: Mus musculus

<400> SEQUENCE: 72

Gly Tyr Thr Phe Thr Asp Tyr Ala Met Asn
1               5                   10

<210> SEQ ID NO 73
<211> LENGTH: 17
<212> TYPE: PRT
<213> ORGANISM: Mus musculus

<400> SEQUENCE: 73

Val Ile Ser Thr Tyr Tyr Gly Asp Ala Asn Tyr Asn Gln Lys Phe Lys
1               5                   10                  15

Gly

<210> SEQ ID NO 74
<211> LENGTH: 10
<212> TYPE: PRT
<213> ORGANISM: Mus musculus

<400> SEQUENCE: 74

Val Ile Ser Thr Tyr Tyr Gly Asp Ala Asn
1               5                   10

<210> SEQ ID NO 75
<211> LENGTH: 9
<212> TYPE: PRT
<213> ORGANISM: Mus musculus

<400> SEQUENCE: 75

Ile Tyr Tyr Asp Tyr Asp Gly Ser Tyr
1               5

<210> SEQ ID NO 76
```

```
<211> LENGTH: 5
<212> TYPE: PRT
<213> ORGANISM: Mus musculus

<400> SEQUENCE: 76

Ser Tyr Thr Met His
1               5

<210> SEQ ID NO 77
<211> LENGTH: 6
<212> TYPE: PRT
<213> ORGANISM: Mus musculus

<400> SEQUENCE: 77

Gly Tyr Thr Phe Thr Ser
1               5

<210> SEQ ID NO 78
<211> LENGTH: 10
<212> TYPE: PRT
<213> ORGANISM: Mus musculus

<400> SEQUENCE: 78

Gly Tyr Thr Phe Thr Ser Tyr Thr Met His
1               5                   10

<210> SEQ ID NO 79
<211> LENGTH: 17
<212> TYPE: PRT
<213> ORGANISM: Mus musculus

<400> SEQUENCE: 79

Tyr Ile Asn Pro Ser Ser Gly Tyr Thr Asp Tyr Asn Gln Lys Phe Lys
1               5                   10                  15

Asp

<210> SEQ ID NO 80
<211> LENGTH: 10
<212> TYPE: PRT
<213> ORGANISM: Mus musculus

<400> SEQUENCE: 80

Tyr Ile Asn Pro Ser Ser Gly Tyr Thr Asp
1               5                   10

<210> SEQ ID NO 81
<211> LENGTH: 11
<212> TYPE: PRT
<213> ORGANISM: Mus musculus

<400> SEQUENCE: 81

Leu Gly Lys Gly Leu Leu Pro Pro Phe Asp Tyr
1               5                   10

<210> SEQ ID NO 82
<211> LENGTH: 5
<212> TYPE: PRT
<213> ORGANISM: Mus musculus

<400> SEQUENCE: 82

Ser Tyr Trp Met Gln
1               5

<210> SEQ ID NO 83
```

```
<211> LENGTH: 6
<212> TYPE: PRT
<213> ORGANISM: Mus musculus

<400> SEQUENCE: 83

Gly Tyr Thr Phe Thr Ser
1               5

<210> SEQ ID NO 84
<211> LENGTH: 10
<212> TYPE: PRT
<213> ORGANISM: Mus musculus

<400> SEQUENCE: 84

Gly Tyr Thr Phe Thr Ser Tyr Trp Met Gln
1               5                   10

<210> SEQ ID NO 85
<211> LENGTH: 17
<212> TYPE: PRT
<213> ORGANISM: Mus musculus

<400> SEQUENCE: 85

Ala Ile Tyr Pro Gly Asp Gly Asp Thr Arg Tyr Thr Gln Lys Phe Lys
1               5                   10                  15
Gly

<210> SEQ ID NO 86
<211> LENGTH: 10
<212> TYPE: PRT
<213> ORGANISM: Mus musculus

<400> SEQUENCE: 86

Ala Ile Tyr Pro Gly Asp Gly Asp Thr Arg
1               5                   10

<210> SEQ ID NO 87
<211> LENGTH: 10
<212> TYPE: PRT
<213> ORGANISM: Mus musculus

<400> SEQUENCE: 87

Arg Tyr Asp Gly Tyr Tyr His Phe Asp Tyr
1               5                   10

<210> SEQ ID NO 88
<211> LENGTH: 5
<212> TYPE: PRT
<213> ORGANISM: Mus musculus

<400> SEQUENCE: 88

Thr Tyr Trp Met Gln
1               5

<210> SEQ ID NO 89
<211> LENGTH: 6
<212> TYPE: PRT
<213> ORGANISM: Mus musculus

<400> SEQUENCE: 89

Gly Phe Thr Phe Thr Thr
1               5

<210> SEQ ID NO 90
```

-continued

```
<211> LENGTH: 10
<212> TYPE: PRT
<213> ORGANISM: Mus musculus

<400> SEQUENCE: 90

Gly Phe Thr Phe Thr Thr Tyr Trp Met Gln
1               5                   10

<210> SEQ ID NO 91
<211> LENGTH: 17
<212> TYPE: PRT
<213> ORGANISM: Mus musculus

<400> SEQUENCE: 91

Ala Ile Tyr Pro Gly Asp Gly Asp Thr Arg Tyr Thr Gln Lys Phe Lys
1               5                   10                  15

Gly

<210> SEQ ID NO 92
<211> LENGTH: 10
<212> TYPE: PRT
<213> ORGANISM: Mus musculus

<400> SEQUENCE: 92

Ala Ile Tyr Pro Gly Asp Gly Asp Thr Arg
1               5                   10

<210> SEQ ID NO 93
<211> LENGTH: 11
<212> TYPE: PRT
<213> ORGANISM: Mus musculus

<400> SEQUENCE: 93

Arg Gly Asp Tyr Gly Asn Tyr Gly Met Asp Tyr
1               5                   10

<210> SEQ ID NO 94
<211> LENGTH: 9
<212> TYPE: PRT
<213> ORGANISM: Mus musculus

<400> SEQUENCE: 94

Gln Gln His Tyr Asn Thr Pro Trp Thr
1               5

<210> SEQ ID NO 95
<211> LENGTH: 15
<212> TYPE: PRT
<213> ORGANISM: Mus musculus

<400> SEQUENCE: 95

Arg Ala Ser Glu Ser Val Asp Asn Phe Gly Ile Ser Phe Met Asn
1               5                   10                  15

<210> SEQ ID NO 96
<211> LENGTH: 7
<212> TYPE: PRT
<213> ORGANISM: Mus musculus

<400> SEQUENCE: 96

Ala Ala Ser Asn Gln Gly Ser
1               5

<210> SEQ ID NO 97
```

```
<211> LENGTH: 9
<212> TYPE: PRT
<213> ORGANISM: Mus musculus

<400> SEQUENCE: 97

Gln Gln Ser Lys Glu Val Pro Tyr Thr
1               5

<210> SEQ ID NO 98
<211> LENGTH: 16
<212> TYPE: PRT
<213> ORGANISM: Mus musculus

<400> SEQUENCE: 98

Arg Ser Ser Gln Ser Leu Val His Ser Asn Gly Asn Thr Tyr Leu His
1               5                   10                  15

<210> SEQ ID NO 99
<211> LENGTH: 7
<212> TYPE: PRT
<213> ORGANISM: Mus musculus

<400> SEQUENCE: 99

Lys Val Ser Asn Arg Phe Ser
1               5

<210> SEQ ID NO 100
<211> LENGTH: 10
<212> TYPE: PRT
<213> ORGANISM: Mus musculus

<400> SEQUENCE: 100

Ser Gln Ser Thr His Val Pro Pro Tyr Thr
1               5                   10

<210> SEQ ID NO 101
<211> LENGTH: 17
<212> TYPE: PRT
<213> ORGANISM: Mus musculus

<400> SEQUENCE: 101

Lys Ser Asn Gln Asn Leu Leu Trp Ser Gly Asn Gln Arg Tyr Cys Leu
1               5                   10                  15

Val

<210> SEQ ID NO 102
<211> LENGTH: 7
<212> TYPE: PRT
<213> ORGANISM: Mus musculus

<400> SEQUENCE: 102

Trp Thr Ser Asp Arg Tyr Ser
1               5

<210> SEQ ID NO 103
<211> LENGTH: 9
<212> TYPE: PRT
<213> ORGANISM: Mus musculus

<400> SEQUENCE: 103

Gln Gln His Leu His Ile Pro Tyr Thr
1               5

<210> SEQ ID NO 104
```

```
<211> LENGTH: 17
<212> TYPE: PRT
<213> ORGANISM: Mus musculus

<400> SEQUENCE: 104

Lys Ser Ser Gln Ser Leu Leu Trp Ser Val Asn Gln Lys Asn Tyr Leu
1               5                   10                  15

Ser

<210> SEQ ID NO 105
<211> LENGTH: 7
<212> TYPE: PRT
<213> ORGANISM: Mus musculus

<400> SEQUENCE: 105

Gly Ala Ser Ile Arg Glu Ser
1               5

<210> SEQ ID NO 106
<211> LENGTH: 11
<212> TYPE: PRT
<213> ORGANISM: Mus musculus

<400> SEQUENCE: 106

Gln His Asn His Gly Ser Phe Leu Pro Leu Thr
1               5                   10

<210> SEQ ID NO 107
<211> LENGTH: 16
<212> TYPE: PRT
<213> ORGANISM: Mus musculus

<400> SEQUENCE: 107

Arg Ser Ser Gln Ser Ile Val His Ser Asn Gly Asn Thr Tyr Leu Glu
1               5                   10                  15

<210> SEQ ID NO 108
<211> LENGTH: 7
<212> TYPE: PRT
<213> ORGANISM: Mus musculus

<400> SEQUENCE: 108

Lys Val Ser Asn His Phe Ser
1               5

<210> SEQ ID NO 109
<211> LENGTH: 9
<212> TYPE: PRT
<213> ORGANISM: Mus musculus

<400> SEQUENCE: 109

Phe Gln Gly Ser His Val Pro Pro Thr
1               5
```